(12) United States Patent
Gray et al.

(10) Patent No.: US 10,975,058 B2
(45) Date of Patent: *Apr. 13, 2021

(54) IMIDAZOLYL KINASE INHIBITORS AND USES THEREOF

(71) Applicant: Dana-Farber Cancer Institute, Inc., Boston, MA (US)

(72) Inventors: Nathanael S. Gray, Boston, MA (US); Hwan Geun Choi, Chestnut Hill, MA (US); Yanke Liang, Belmont, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/410,371

(22) Filed: May 13, 2019

(65) Prior Publication Data

US 2019/0367487 A1 Dec. 5, 2019

Related U.S. Application Data

(63) Continuation of application No. 15/327,705, filed as application No. PCT/US2015/041348 on Jul. 21, 2015, now Pat. No. 10,287,268.

(60) Provisional application No. 62/027,122, filed on Jul. 21, 2014.

(51) Int. Cl.
*C07D 403/04* (2006.01)
*C07D 403/14* (2006.01)

(52) U.S. Cl.
CPC .......... *C07D 403/04* (2013.01); *C07D 403/14* (2013.01)

(58) Field of Classification Search
CPC ... C07D 498/04; C07D 487/04; C07D 401/14
USPC ........................................................ 514/252
See application file for complete search history.

(56) References Cited

U.S. PATENT DOCUMENTS

| | | | |
|---|---|---|---|
| 6,150,373 A | 11/2000 | Harris et al. | |
| 6,217,875 B1 | 4/2001 | Murai et al. | |
| 7,084,270 B2 | 8/2006 | Chen et al. | |
| 7,112,676 B2 | 9/2006 | Dermatakis et al. | |
| 7,312,225 B2 | 12/2007 | Luecking et al. | |
| 8,921,336 B2 | 12/2014 | Gray et al. | |
| 9,586,936 B2 | 3/2017 | Sim et al. | |
| 9,663,524 B2 | 5/2017 | Barrague et al. | |
| 9,670,165 B2 | 6/2017 | Cohen et al. | |
| 9,783,504 B2 | 10/2017 | Gray et al. | |
| 9,925,188 B2* | 3/2018 | Charifson | A61K 31/5377 |
| 10,233,157 B2 | 3/2019 | Cohen et al. | |
| 10,265,321 B2 | 4/2019 | Shamji et al. | |
| 10,287,268 B2* | 5/2019 | Gray | C07D 403/14 |
| 10,457,691 B2 | 10/2019 | Gray et al. | |
| 2004/0204427 A1 | 10/2004 | Chen et al. | |
| 2005/0026914 A1 | 2/2005 | Buchanan et al. | |
| 2005/0202001 A1 | 9/2005 | Shen et al. | |
| 2006/0258687 A1 | 11/2006 | Boehm et al. | |
| 2007/0225286 A1 | 9/2007 | Ren et al. | |
| 2008/0249079 A1 | 10/2008 | Chen et al. | |
| 2009/0137804 A1 | 5/2009 | Ding et al. | |
| 2010/0056524 A1 | 3/2010 | McIver et al. | |
| 2011/0086858 A1 | 4/2011 | Wang et al. | |
| 2011/0207711 A1 | 8/2011 | Katz et al. | |
| 2017/0204082 A1 | 7/2017 | Gray et al. | |
| 2017/0204116 A1 | 7/2017 | Gray et al. | |
| 2017/0224700 A1 | 8/2017 | Shamji et al. | |
| 2017/0342036 A1 | 11/2017 | Cohen et al. | |
| 2018/0221379 A1 | 8/2018 | Shamji et al. | |

(Continued)

FOREIGN PATENT DOCUMENTS

EP 2 746 283 A1 6/2014
WO WO 2000/024744 A1 5/2000

(Continued)

OTHER PUBLICATIONS

Extended European Search Report for EP 15824907.8, dated Jan. 2, 2018.

(Continued)

*Primary Examiner* — Tracy Vivlemore
*Assistant Examiner* — Ebenezer O Sackey
(74) *Attorney, Agent, or Firm* — Wolf, Greenfield & Sacks, P.C.

(57) ABSTRACT

The present disclosure provides imidazolyl compounds of Formula (I) and methods of preparing the compounds. The provided compounds are able to bind protein kinases and may be useful in modulating (e.g., inhibiting) the activity of a protein kinase in a subject or cell and/or in treating or preventing a disease (e.g., proliferative disease, genetic disease, hematological disease, neurological disease, painful condition, psychiatric disorder, or metabolic disorder) in a subject in need thereof. Also provided are pharmaceutical compositions, kits, methods, and uses that include or involve a compound described herein.

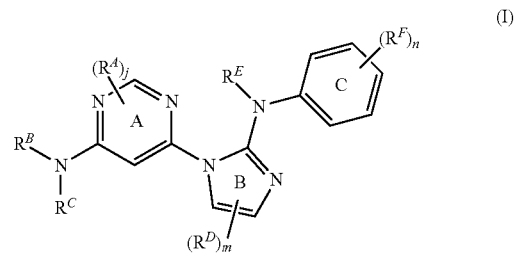

32 Claims, No Drawings

(56) References Cited

U.S. PATENT DOCUMENTS

| | | | |
|---|---|---|---|
| 2019/0315752 A1 | 10/2019 | Gray et al. | |
| 2019/0343842 A1 | 11/2019 | Shamji et al. | |
| 2020/0179387 A1 | 6/2020 | Wein et al. | |
| 2020/0253981 A1 | 8/2020 | Fisher et al. | |

FOREIGN PATENT DOCUMENTS

| | | |
|---|---|---|
| WO | WO 2004/041821 A1 | 5/2004 |
| WO | WO 2004/041822 A1 | 5/2004 |
| WO | WO 2004/048343 A1 | 6/2004 |
| WO | WO 2005/009443 A1 | 2/2005 |
| WO | WO 2005/009978 A1 | 2/2005 |
| WO | WO 2005/011597 A2 | 2/2005 |
| WO | WO 2005/123719 A1 | 12/2005 |
| WO | WO 2006/000420 A1 | 1/2006 |
| WO | WO 2006/024545 A1 | 3/2006 |
| WO | WO 2007/071752 A2 | 6/2007 |
| WO | WO 2007/136465 A2 | 11/2007 |
| WO | WO 2008/060248 A1 | 5/2008 |
| WO | WO 2009/073153 A2 | 6/2009 |
| WO | WO 2009/122180 A1 | 10/2009 |
| WO | WO 2009/152027 A1 | 12/2009 |
| WO | WO 2013/045653 A1 | 4/2013 |
| WO | WO 2013/074986 A1 | 5/2013 |
| WO | WO 2013/136070 A1 | 9/2013 |
| WO | WO 2014/093383 A1 | 6/2014 |
| WO | WO 2014/140313 A1 | 9/2014 |
| WO | WO 2014/144737 A1 | 9/2014 |
| WO | WO 2015/006492 A1 | 1/2015 |
| WO | WO 2016/014542 A1 | 1/2016 |
| WO | WO 2016/014551 A1 | 1/2016 |
| WO | WO 2016/023014 A2 | 2/2016 |

OTHER PUBLICATIONS

Invitation to Pay Additional Fees for PCT/US2015/041360 mailed Sep. 24, 2015.
International Search Report and Written Opinion for PCT/US2015/041360 dated Dec. 15, 2015.
International Preliminary Report on Patentability for PCT/US2015/041360 dated Feb. 2, 2017.
Extended European Search Report for EP 15824975.5, dated Nov. 27, 2017.
International Search Report and Written Opinion for PCT/US2015/41348 dated Oct. 28, 2015.
International Preliminary Report on Patentability for PCT/US2015/41348 dated Feb. 2, 2017.
Partial Supplementary European Search Report for EP 15829427.2, dated Feb. 8, 2018.
Extended European Search Report for EP 15829427.2, dated May 15, 2018.
Invitation to Pay Additional Fees for PCT/US2015/044387, mailed Jan. 28, 2016.
International Search Report and Written Opinion for PCT/US2015/044387, dated Mar. 25, 2016.
International Preliminary Report on Patentability for PCT/US2015/044387, dated Feb. 23, 2017.
International Preliminary Report on Patentability for PCT/GB2013/050618, dated Sep. 25, 2014.
International Search Report and Written Opinion for PCT/GB2013/050618, dated May 17, 2013.
Invitation to Pay Additional Fees for PCT/US2017/040722, mailed Oct. 18, 2017.
International Search Report and Written Opinion for PCT/US2017/040722, dated Dec. 12, 2017.
International Preliminary Report on Patentability for PCT/US2017/040722, dated Jan. 17, 2019.
International Search Report and Written Opinion for PCT/US2018/020335, dated May 17, 2018.
Extended European Search Report for EP 19164054.9, dated Jul. 31, 2019.
International Preliminary Report on Patentability for PCT/US2018/020335, dated Sep. 12, 2019.
International Search Report and Written Opinion for PCT/US2017/051937, dated Dec. 28, 2017.
International Preliminary Report on Patentability for PCT/US2017/051937, dated Mar. 28, 2019.
Altarejos et al., CREB and the CRTC co-activators: sensors for hormonal and metabolic signals. Nat Rev Mol Cell Biol. Mar. 2011;12(3):141-51. doi: 10.1038/nrm3072.
Antiga et al., Serum levels of the regulatory cytokines transforming growth factor-β and interleukin-10 are reduced in patients with discoid lupus erythematosus. Lupus. May 2011;20(6):556-60. doi: 10.1177/0961203310392424. Epub Mar. 3, 2011.
Bain et al., The selectivity of protein kinase inhibitors: a further update. Biochem J. Dec. 15, 2007;408(3):297-315.
Bettencourt-Dias et al., Genome-wide survey of protein kinases required for cell cycle progression. Nature. Dec. 23, 2004;432(7020):980-7.
Eyers et al., Conversion of SB 203580-insensitive MAP kinase family members to drug-sensitive forms by a single amino-acid substitution. Chem Biol. Jun. 1998;5(6):321-8.
Garcia-Gomez et al., Dasatinib as a bone-modifying agent:anabolic and anti-resorptive effects. PLoS One. 2012;7(4):e34914. doi:10.1371/journal.pone.0034914. Epub Apr. 23, 2012.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Jansson et al., Glucose controls CREB activity in islet cells via regulated phosphorylation of TORC2. Proc Natl Acad Sci U S A. Jul. 22, 2008;105(29):10161-6. doi: 10.1073/pnas.0800796105. Epub Jul. 14, 2008.
Liu et al., Engineering Src family protein kinases with unnatural nucleotide specificity. Chem Biol. Feb. 1998;5(2):91-101.
Maier et al., Development of N-4,6-pyrimidine-N-alkyl-N'-phenyl ureas as orally active inhibitors of lymphocyte specific tyrosine kinase. Bioorg Med Chem Lett. Jul. 15, 2006;16(14):3646-50. Epub May 8, 2006.
Mair et al., Lifespan extension induced by AMPK and calcineurin is mediated by CRTC-1 and CREB. Nature. Feb. 17, 2011;470(7334):404-8. doi: 10.1038/nature09706.
Mallison et al., Macrocycles in new drug discovery. Future Med Chem. Jul. 2012;4(11):1409-38. doi: 10.4155/fmc.12.93.
Manthey et al., JNJ-28312141, a novel orally active colony-stimulating factor-1 receptor/FMS-related receptor tyrosine kinase-3 receptor tyrosine kinase inhibitor with potential utility in solid tumors, bone metastases, and acute myeloid leukemia. Mol Cancer Ther. Nov. 2009;8(11):3151-61. doi:10.1158/1535-7163.MCT-09-0255. Epub Nov. 3, 2009.
McWhirter et al., IFN-regulatory factor 3-dependent gene expression is defective in Tbk1-deficient mouse embryonic fibroblasts. Proc Natl Acad Sci U S A. Jan. 6, 2004;101(1):233-8. Epub Dec. 16, 2003.
Pethe et al., A chemical genetic screen in Mycobacterium tuberculosis identifies carbon-source-dependent growth inhibitors devoid of in vivo efficacy. Nature Communications 2010;1:57. doi:10.1038/ncomms1060.
Tella et al., Prevention and treatment of postmenopausal osteoporosis. J Steroid Biochem Mol Biol. Jul. 2014;142:155-70. doi:10.1016/j.jsbmb.2013.09.008. Epub Oct. 29, 2013.
Walkinshaw et al., The tumor suppressor kinase LKB1 activates the downstream kinases SIK2 and SIK3 to stimulate nuclear export of class IIa histone deacetylases. J Biol Chem. Mar. 29, 2013;288(13):9345-62. doi: 10.1074/jbc.M113.456996. Epub Feb. 7, 2013.
Wu et al., Exploring the selectivity of PI3Kα and mTOR inhibitors by 3D-QSAR, molecular dynamics simulations and MM/GBSA binding free energy decomposition. Med. Chem. Commun., 2013;4:1482-1496. DOI: 10.1039/C3MD00157A.
CAPLUS Accession No. 2015:690395. 2 pages. Reynolds et al., N-Aryl-heteroarylamines as FGFR4 inhibitors and their Preparation.

(56) References Cited

OTHER PUBLICATIONS

CAPLUS Accession No. 2015:453874. 12 pages. Ding et al., Pyrimido-heterocyclic compounds as EGFR protease inhibitors and their preparation, pharmaceutical compositions and use in the treatment of cancer.
CAPLUS Accession No. 2015:76117. 2 pages. Gray et al., Preparation of functionalized pyrimidine compounds as kinase inhibitors for the treatment of proliferative diseases.
CAPLUS Accession No. 2014:1815213. 3 pages. Tan et al., Development of covalent inhibitors that can overcome resistance to first-generation FGFR kinase inhibitors.
CAPLUS Accession No. 2014:1753550. 1 page. Huang et al., DFG-out Mode of Inhibition by an Irreversible Type-1 Inhibitor Capable of Overcoming Gate-Keeper Mutations.
CAPLUS Accession No. 2014:1558688. 10 pages. D'Agostino et al., Preparation of heteroaryl compounds as inhibitors of protein kinases.
CAPLUS Accession No. 2013:1609048. 10 pages. Xu et al., Design, Synthesis, and Biological Evaluation of 2-Oxo-3,4-dihydropyrimido[4,5 d]pyrimidinyl Derivatives as New Irreversible Epidermal Growth Factor Receptor Inhibitors with Improved Pharmacokinetic Properties.
CAPLUS Accession No. 2013:82305. 2 pages. Zender et al., Pharmaceutical compositions comprising sorafenib in combination with MAPK14 inhibitors for the treatment and prevention of liver cancer.
CAPLUS Accession No. 2013:51064. 2 pages. Zender et al., Pharmaceutical compositions comprising sorafenib in combination with MAPK14 inhibitors for the treatment and prevention of liver cancer.
CAPLUS Accession No. 2012:1832180. 2 pages. Ding et al., Pyrimidopyrimidone derivatives as EGFR inhibitors and their preparation, pharmaceutical compositions and use in the treatment of cancers.
CAPLUS Accession No. 2012:1816780. 5 pages. Ding et al., Pyrimidopyrimidone derivatives as EGFR inhibitors and their preparation, pharmaceutical compositions and use in the treatment of cancers.
CAPLUS Accession No. 2012:1191791. 1 page. Wan et al., Discovery of novel Bruton's tyrosine kinase inhibitors using a hybrid protocol of virtual screening approaches based on SVM model, pharmacophore and molecular docking.
CAPULS Accession No. 2012:235081. 3 pages. Chang et al., Design, Synthesis, and Biological Evaluation of Novel Conformationally Constrained Inhibitors Targeting Epidermal Growth Factor Receptor Threonine790 ® Methionine790 Mutant.
CAPLUS Accession No. 2011:391484. 1 page. Kuglstatter et al., Insights into the conformational flexibility of Bruton's tyrosine kinase from multiple ligand complex structures.
CAPLUS Accession No. 2007:1363959. 4 page. Ren et al., Preparation of pyrimidopyrimidinones and analogs as FGF receptor kinases inhibitors.
CAPLUS Accession No. 2006:333232. 17 pages. Engh et al., Preparation of amide derivatives of 3-phenyl-dihydropyrimido[4,5-d]pyrimidinones as antitumor agents.
CAPLUS Accession No. 2005:120672. 22 pages. Sim et al., Preparation of pyrimidopyrimidines as protein kinase inhibitors.
CAPLUS Accession No. 2004:412945. 5 pages. Luk et al., Preparation of pyrimido Src tyrosine kinase inhibitors as anti-proliferative agents for the treatment of cancer.
CAPLUS Accession No. 2000:291041. 11 pages. Harris et al., Preparation of pyrimidopyrimidinones as T-cell tyrosine kinase inhibitors.
CAPLUS Accession No. 1999:764041. 5 pages. Dobrusin et al., Preparation of oxopyrido- and -pyrimidopyrimidines as cellular proliferation inhibitors.
U.S. Appl. No. 15/327,690, filed Jan. 20, 2017, Gray et al.
U.S. Appl. No. 15/327,705, filed Jan. 20, 2017, Gray et al.
U.S. Appl. No. 15/502,287, filed Feb. 7, 2017, Shamji et al.
U.S. Appl. No. 15/847,856, filed Dec. 19, 2017, Shamji et al.
U.S. Appl. No. 14/385,077, filed Sep. 12, 2014, Cohen et al.
U.S. Appl. No. 15/606,970, filed May 26, 2017, Cohen et al.
U.S. Appl. No. 16/489,462, filed Aug. 28, 2019, Fisher et al.
U.S. Appl. No. 16/333,546, filed Mar. 14, 2019, Wein et al.
PCT/GB2013/050618, May 17, 2013, International Search Report and Written Opinion.
PCT/GB2013/050618, Sep. 25, 2014, International Preliminary Report on Patentability.
PCT/US2015/041360, Sep. 24, 2015, Invitation to Pay Additional Fees.
PCT/US2015/41348, Oct. 28, 2015, International Search Report and Written Opinion.
PCT/US2015/041360, Dec. 15, 2015, International Search Report and Written Opinion.
PCT/US2015/04438, Jan. 28, 2016, Invitation to Pay Additional Fees.
PCT/US2015/04438, Mar. 25, 2016, International Search Report and Written Opinion.
PCT/US2015/041360, Feb. 2, 2017, International Preliminary Report on Patentability.
PCT/US2015/41348, Feb. 2, 2017, International Preliminary Report on Patentability.
PCT/US2015/04438, Feb. 23, 2017, International Preliminary Report on Patentability.
PCT/US2017/040722, Oct. 18, 2017, Invitation to Pay Additional Fees.
EP 15824975.5, Nov. 27, 2017, Extended European Search Report.
PCT/US2017/040722, Dec. 12, 2017, International Search Report and Written Opinion.
PCT/US2017/051937, Dec. 28, 2017, International Search Report and Written Opinion.
EP 15824907.8, Jan. 2, 2018, Extended European Search Report.
EP 15829427.2, Feb. 8, 2018, Partial Supplementary European Search Report.
EP 15829427.2, May 14, 2018, Extended European Search Report.
PCT/US2018/020335, May 17, 2018, International Search Report and Written Opinion.
PCT/US2017/040722, Jan. 17, 2019, International Preliminary Report on Patentability.
PCT/US2017/051937, Mar. 28, 2019, International Preliminary Report on Patentability.
EP 19164054.9, Jul. 31, 2019, Extended European Search Report.
PCT/US2018/020335, Sep. 12, 2019, International Preliminary Report on Patentability.

\* cited by examiner

IMIDAZOLYL KINASE INHIBITORS AND USES THEREOF

RELATED APPLICATIONS

The present application is a continuation of and claims priority under 35 U.S.C. § 120 to U.S. application Ser. No. 15/327,705, filed Jan. 20, 2017, now U.S. Pat. No. 10,287,268, which is a national stage filing under 35 U.S.C. § 371 of international PCT application, PCT/US2015/041348, filed Jul. 21, 2015, which claims priority under 35 U.S.C. § 119(e) to U.S. provisional patent application, U.S. Ser. No. 62/027,122, filed Jul. 21, 2014, the entire contents of each of which are incorporated herein by reference.

BACKGROUND OF THE INVENTION

A protein kinase inhibitor is an enzyme inhibitor that blocks the action of a protein kinase. A protein kinase is an enzyme that adds a phosphate group to a protein or other organic molecule. Phosphorylation is involved in a wide range of diseases, such as diseases associated with aberrant activity (e.g., increased activity) of a protein kinase. Such diseases include, but are not limited to, proliferative diseases (e.g., cancers, benign neoplasms, pathological angiogenesis, inflammatory diseases, and autoimmune diseases). Inhibiting protein kinases, and therefore the phosphorylation of a substrate protein, has been shown to be useful in treating these diseases. For example, afatinib, an ErbB inhibitor, is useful in treating non-small cell lung cancer; axitinib, a VEGFR, PDGFR, and c-KIT inhibitor, is useful in treating renal cell carcinoma; bosutinib, a Bcr-Abl inhibitor, is useful in treating chronic myelogenous leukemia; cabozantinib, a c-Met and VEGFR2 inhibitor, is useful in treating thyroid cancer; crizotinib, an ALK, HGFR, and c-MET inhibitor, is useful in treating non-small cell lung cancer; dasatinib, a Bcr-Abl, Src, and c-KIT inhibitor, is useful in treating chronic myelogenous leukemia; erlotinib, an EGFR inhibitor, is useful in treating non-small cell lung cancer and pancreatic cancer; gefitinib, an EGFR inhibitor, is useful in treating non-small cell lung cancer; imatinib, a Bcr-Abl inhibitor, is useful in treating chronic myelogenous leukemia; lapatinib, a HER2 inhibitor, is useful in treating breast cancer; nilotinib, a Bcr-Abl inhibitor, is useful in treating chronic myelogenous leukemia; pazopanib, a VEGFR, PDGFR, and c-KIT inhibitor, is useful in treating renal cell carcinoma and soft tissue sarcoma; ponatinib, a Bcr-Abl, BEGFR, PDGFR, FGFR, EPH, SRC, c-KIT, RET, TIE2, and FLT3 inhibitor, is useful in treating chronic myelogenous leukemia and acute lymphoblastic leukemia; regorafenib, a RET, VEGFR, and PDGFR inhibitor, is useful in treating colorectal cancer and gastrointestinal stromal tumor; ruxolitinib, a JAK inhibitor, is useful in treating myelofibrosis; sorafenib, a VEGFR, PDGFR, BRAF, and c-KIT inhibitor, is useful in treating renal cell carcinoma and hepatocellular carcinoma; sunitinib, a VEGFR and PDGFR inhibitor, is useful in treating renal cell carcinoma, gastrointestinal stromal tumor, and pancreatic neuroendocrine tumor; tofacitinib, a JAK inhibitor, is useful in treating rheumatoid arthritis; vandetanib, a VEGFR, EGFR, RET and BRK inhibitor, is useful in treating thyroid cancer; and vemurafenib, a BRAF inhibitor, is useful in treating malignant melanoma. There remains a need for protein kinase inhibitors for improved treatment of diseases associated with aberrant activity of protein kinases.

SUMMARY OF THE INVENTION

Described herein are imidazolyl compounds of Formula (I). The compounds described herein bind protein kinases and therefore may be useful in modulating (e.g., inhibiting) the activity of a protein kinase in a subject or cell. The compounds may be useful in treating and/or preventing a disease or condition associated with aberrant kinase activity, e.g., in treating and/or preventing a proliferative disease, genetic disease, hematological disease, neurological disease, painful condition, psychiatric disorder, or metabolic disorder, in a subject in need thereof. Also provided are pharmaceutical compositions and kits including a compound described herein.

In one aspect, the present disclosure provides compounds of Formula (I):

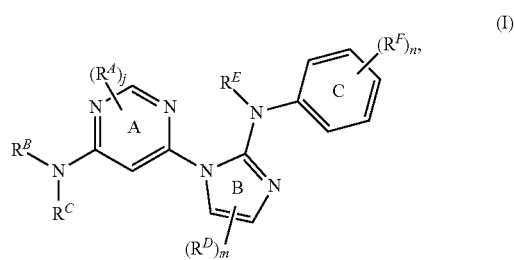

and pharmaceutically acceptable salts, solvates, hydrates, polymorphs, co-crystals, tautomers, stereoisomers, isotopically labeled derivatives, and prodrugs thereof.

In certain embodiments, the compound of Formula (I) is of Formula (I-A):

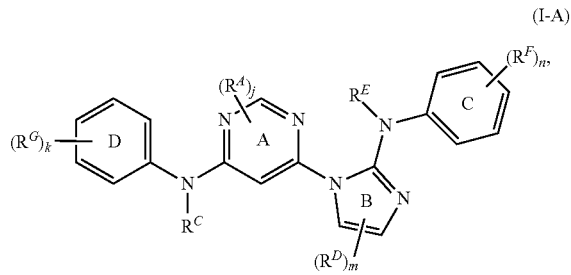

or a pharmaceutically acceptable salt, solvate, hydrate, polymorph, co-crystal, or tautomer thereof.

In certain embodiments, the compound of Formula (I) is of Formula (I-B):

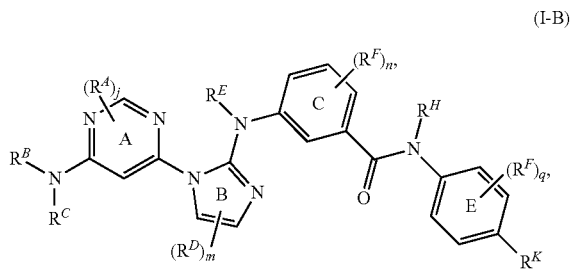

or a pharmaceutically acceptable salt, solvate, hydrate, polymorph, co-crystal, or tautomer thereof.

Exemplary compounds of Formula (I) include, but are not limited to:

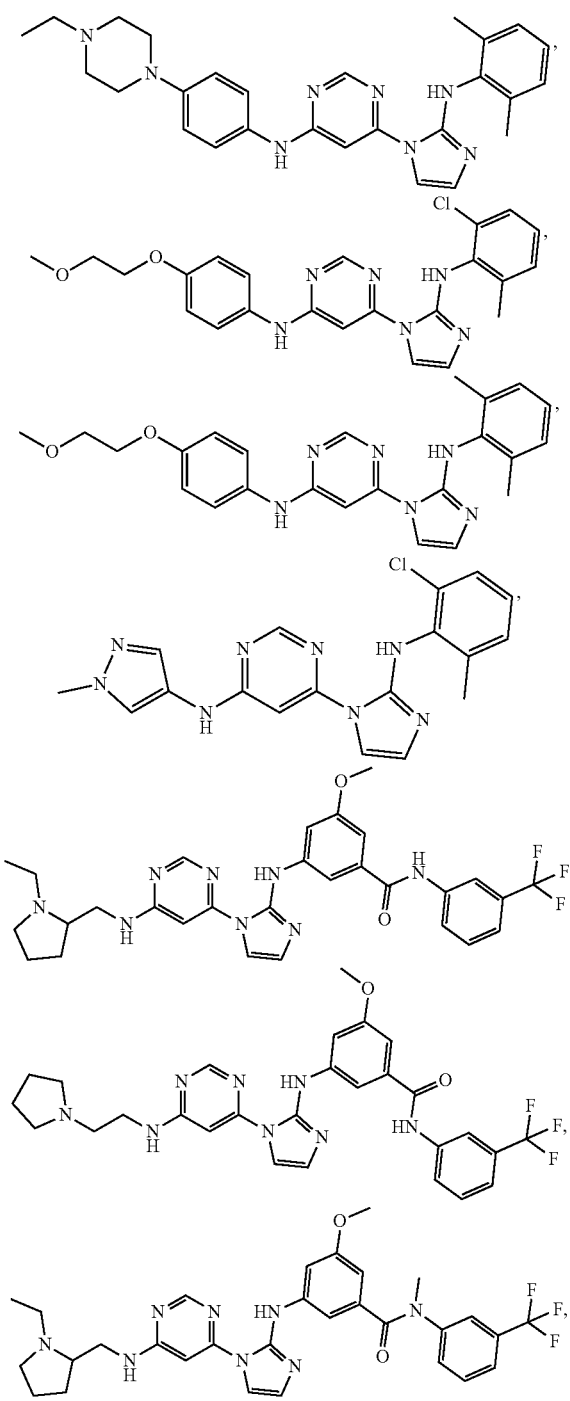
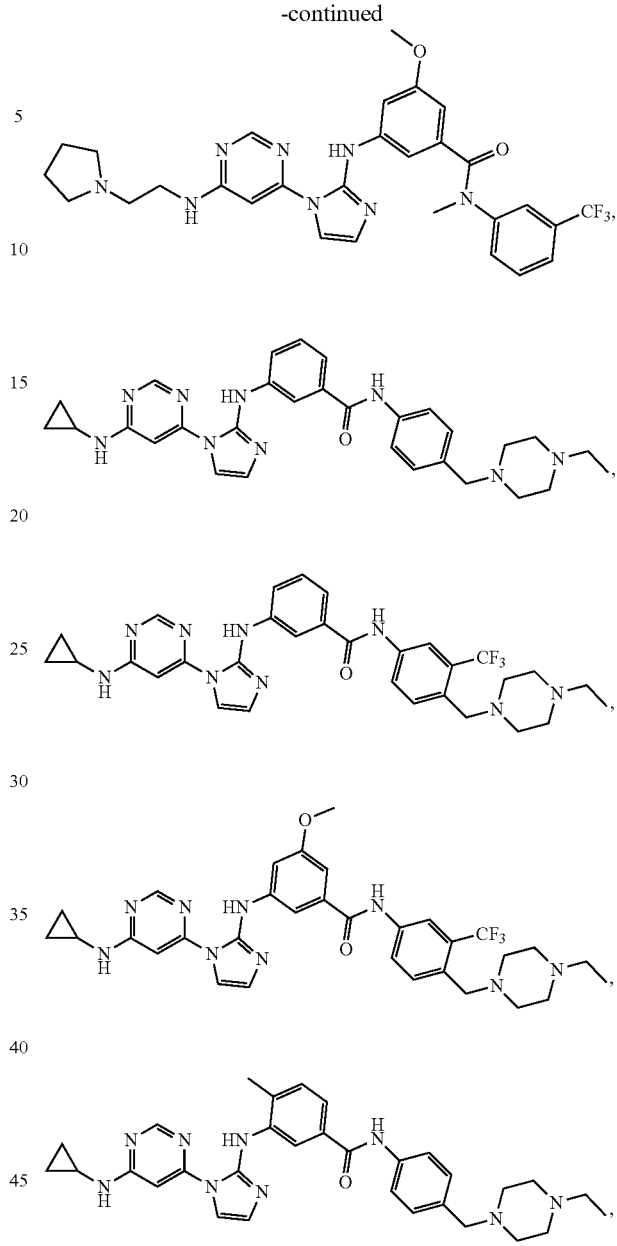
and pharmaceutically acceptable salts, solvates, hydrates, polymorphs, co-crystals, tautomers, stereoisomers, isotopically labeled derivatives, and prodrugs thereof.
In certain embodiments, the compound of Formula (I) is not of the formula:
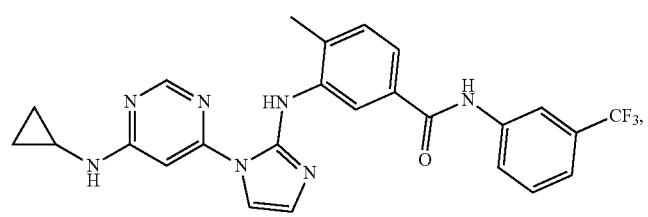

-continued
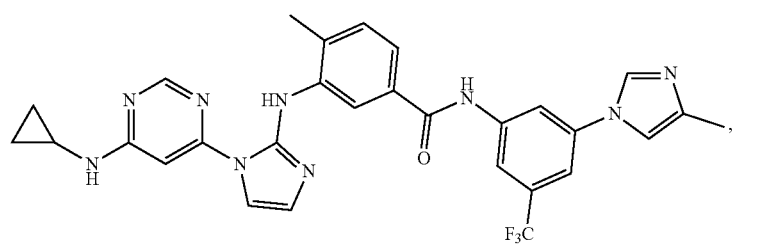
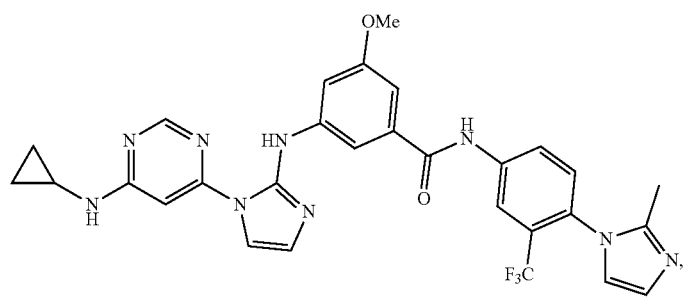
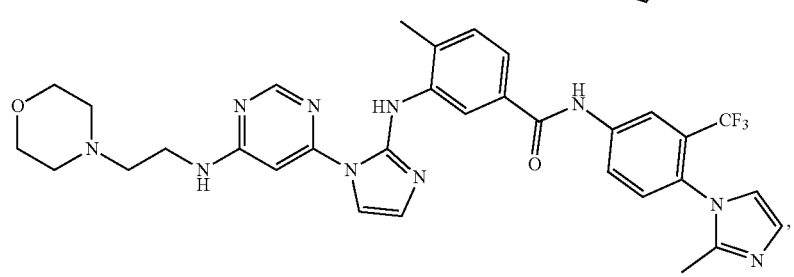
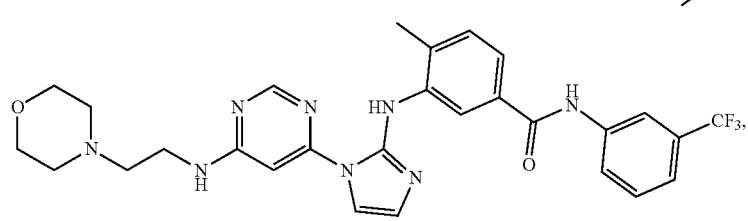
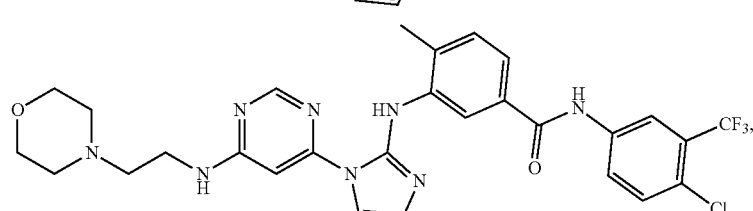
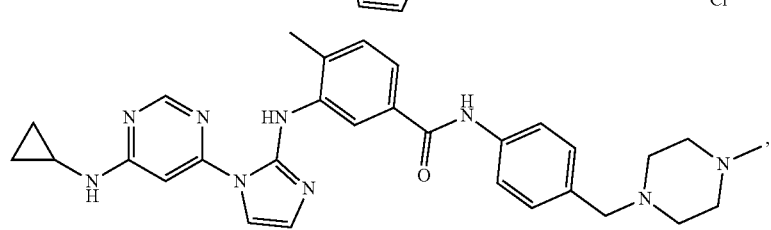
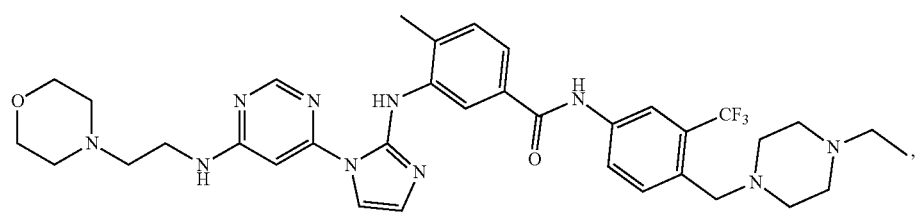

-continued

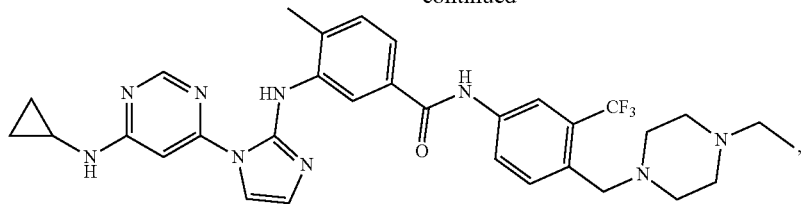

or a pharmaceutically acceptable salt, solvate, hydrate, polymorph, co-crystal, or tautomer thereof.

In another aspect, provided are methods for preparing the compounds described herein, the methods including aminating a compound of Formula (A), or a salt thereof, with an amine of Formula (B), or a salt thereof:

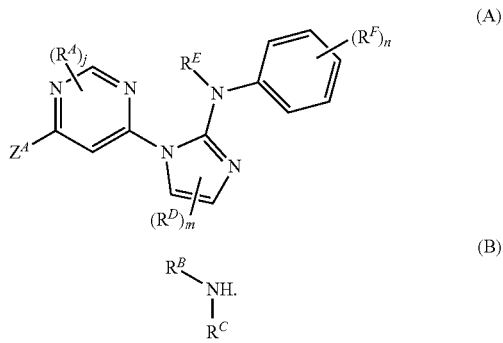

The methods of preparing the compounds described herein may further including aminating a pyrimidine derivative of Formula (C), or a salt thereof, with an imidazole derivative of Formula (D), or a salt thereof, to provide the compound of Formula (A), or salt thereof:

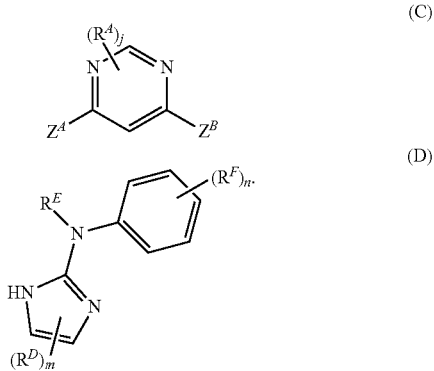

In another aspect, described herein are pharmaceutical compositions including a compound described herein, and optionally a pharmaceutically acceptable excipient. In certain embodiments, a pharmaceutical composition described herein includes a therapeutically or prophylactically effective amount of a compound described herein. The pharmaceutical compositions may be useful in modulating (e.g., inhibiting) the activity of a protein kinase in a subject or cell, in treating a disease (e.g., a proliferative disease) in a subject in need thereof, or in preventing a disease in a subject in need thereof.

In certain embodiments, the disease is a disease or condition associated with aberrant (e.g., increased) kinase activity. In certain embodiments, the disease is a proliferative disease (e.g., cancer, benign neoplasm, pathological angiogenesis, inflammatory disease, or autoimmune disease), genetic disease, hematological disease, neurological disease, painful condition, psychiatric disorder, or metabolic disorder.

In certain embodiments, the subject is a human. In certain embodiments, the subject is a non-human animal. In certain embodiments, the cell is in vitro. In certain embodiments, the cell is in vivo.

In still another aspect, described herein are kits including a container with a compound or pharmaceutical composition described herein. A kit described herein may include a single dose or multiple doses of the compound or pharmaceutical composition. The described kits may be useful in inhibiting the activity of a protein kinase in a subject or cell, in treating a disease or condition associated with aberrant kinase activity in a subject in need thereof, in preventing a disease or condition associated with aberrant kinase activity in a subject in need thereof, in treating a disease (e.g., proliferative disease, genetic disease, hematological disease, neurological disease, painful condition, psychiatric disorder, or metabolic disorder) in a subject in need thereof, and/or in preventing a disease (e.g., proliferative disease, genetic disease, hematological disease, neurological disease, painful condition, psychiatric disorder, or metabolic disorder) in a subject in need thereof. In certain embodiments, a kit described herein further includes instructions for using the kit.

In another aspect, the present disclosure provides methods of modulating (e.g., inhibiting) the activity of a protein kinase in a subject or cell. In certain embodiments, the activity of a protein kinase is aberrant or unwanted activity (e.g., an increased activity) of the protein kinase.

In certain embodiments, the compound being administered or used selectively inhibits the activity of a particular protein kinase.

Another aspect of the present disclosure relates to methods of treating a disease in a subject in need thereof.

In another aspect, the present disclosure provides methods of preventing a disease in a subject in need thereof.

The methods of the present disclosure include administering to the subject or contacting a cell with an effective amount of a compound or pharmaceutical composition described herein. In certain embodiments, the effective amount is a therapeutically effective amount. In certain embodiments, the effective amount is a prophylactically effective amount.

Another aspect of the disclosure relates to methods of screening a library of compounds to identify a compound that is useful in a method of the disclosure.

In yet another aspect, the present disclosure provides compounds and pharmaceutical compositions described herein for use in a method of the disclosure (e.g., a method of inhibiting a protein kinase, a method of treating a disease (e.g., a proliferative disease), or a method of preventing a disease (e.g., a proliferative disease)).

The present application refers to various issued patent, published patent applications, journal articles, and other publications, all of which are incorporated herein by reference. The details of one or more embodiments of the invention are set forth herein. Other features, objects, and advantages of the invention will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The disclosure additionally encompasses compounds as individual isomers substantially free of other isomers, and alternatively, as mixtures of various isomers.

In a formula, --- is absent or a single bond, and === or ≡≡≡ is a single or double bond.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is unspecified (e.g., —CH=CHCH$_3$ or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_5$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)($R^{aa}$)$_2$, —P(=O)(O$R^{cc}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3^+X^-$, —N(O$R^{ee}$)$R^{ff}$, —SH, —S$R^{ee}$, —SS$R^{ee}$, —C(=O)$R^{ee}$, —CO$_2$H, —CO$_2R^{ee}$, —OC(=O)$R^{ee}$, —OCO$_2R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2R^{ee}$, —SO$_2$N($R^{ff}$)$_2$, —SO$_2R^{ee}$, —SO$_2$O$R^{ee}$, —OSO$_2R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)(O$R^{ee}$)$_2$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-}$alkyl)$_2^+X^-$, —NH$_2$($C_{1-6}$ alkyl)$^+X^-$, —NH$_3^+X^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2C_{1-6}$ alkyl, —SO$_2$O$C_{1-6}$ alkyl, —OSO$_2C_{1-6}$alkyl, —SO$C_{1-6}$ alkyl, —Si($C_{1-6}$ alkyl)$_3$, —OSi($C_{1-6}$ alkyl)$_3$ —C(=S)N($C_{1-6}$ alkyl)$_2$, C(=S)NH($C_{1-6}$ alkyl), C(=S) NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —O$R^{aa}$, —ON($R^{bb}$)$_2$, —OC(=O) S$R^{aa}$, —OC(=O)$R^{aa}$, —OCO$_2R^{aa}$, —OC(=O)N($R^{bb}$)$_2$, —OC(=N$R^{bb}$)$R^{aa}$, —OC(=N$R^{bb}$)O$R^{aa}$, —OC(=N$R^{bb}$)N ($R^{bb}$)$_2$, —OS(=O)$R^{aa}$, —OSO$_2R^{aa}$, —OSi($R^{aa}$)$_3$, —OP ($R^{cc}$)$_2$, —OP($R^{cc}$)$_3^+X^-$, —OP(O$R^{cc}$)$_2$, —OP(O$R^{cc}$)$_3^+X^-$, —OP(=O)($R^{aa}$)$_2$, —OP(=O)(O$R^{cc}$)$_2$, and —OP(=O)(N ($R^{bb}$))$_2$, wherein $X^-$, $R^{aa}$, $R^{bb}$, and $R^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —S$R^{aa}$, —S=S$R^{cc}$, —SC(=S)S$R^{aa}$, —SC(=O)S$R^{aa}$, —SC(=O)O$R^{aa}$, and —SC(=O)$R^{aa}$, wherein $R^{aa}$ and $R^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2R^{aa}$, —NHC(=O)N($R^{bb}$)$_2$, —NHC(=N$R^{bb}$)N($R^{bb}$)$_2$, —NHSO$_2R^{aa}$, —NHP(=O)(O$R^{cc}$)$_2$, and —NHP(=O)(N($R^{bb}$)$_2$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —N$R^{bb}$C(=O)$R^{aa}$, —N$R^{bb}$CO$_2R^{aa}$, —N$R^{bb}$C(=O)N($R^{bb}$)$_2$, —N$R^{bb}$C(=N$R^{bb}$)N($R^{bb}$)$_2$, —N$R^{bb}$SO$_2R^{aa}$, —N$R^{bb}$P(=O)(O$R^{cc}$)$_2$, and —N$R^{bb}$P(=O)(N($R^{bb}$)$_2$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+$X$^-$, wherein $R^{bb}$ and X$^-$ are as defined herein.

The term "sulfonyl" refers to a group selected from —SO$_2$N($R^{bb}$)$_2$, —SO$_2R^{aa}$, and —SO$_2$O$R^{aa}$, wherein $R^{aa}$ and $R^{bb}$ are as defined herein.

The term "sulfinyl" refers to the group —S(=O)$R^{aa}$, wherein $R^{aa}$ is as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)$R^{aa}$), carboxylic acids (—CO$_2$H), aldehydes (—CHO), esters (—CO$_2R^{aa}$, —C(=O)S$R^{aa}$, —C(=S)S$R^{aa}$), amides (—C(=O)N($R^{bb}$)$_2$, —C(=O)N$R^{bb}$SO$_2R^{aa}$, —C(=S)N($R^{bb}$)$_2$), and imines (—C(=N$R^{bb}$)$R^{aa}$, —C(=N$R^{bb}$)O$R^{aa}$, —C(=N$R^{bb}$)N($R^{bb}$)$_2$), wherein $R^{aa}$ and $R^{bb}$ are as defined herein.

The term "silyl" refers to the group —Si($R^{aa}$)$_3$, wherein $R^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl- 2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{cc}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. In certain embodiments, the leaving group is an activated substituted hydroxyl group (e.g., —$OC(=O)SR^{aa}$, —$OC(=O)R^{aa}$, —$OCO_2R^{aa}$, —$OC(=O)N(R^{bb})_2$, —$OC(=NR^{bb})R^{aa}$, —$OC(=NR^{bb})OR^{aa}$, $OC(=NR^{bb})N(R^{bb})_2$, —$OS(=O)R^{aa}$, —$OSO_2R^{aa}$, —$OP(R^{cc})_2$, —$OP(R^{cc})_3$, —$OP(=O)_2R^{aa}$, —$OP(=O)(R^{aa})_2$, —$OP(=O)(OR^{cc})_2$, —$OP(=O)_2N(R^{bb})_2$, or —$OP(=O)(NR^{bb})_2$, wherein $R^{cc}$, $R^{bb}$, and $R^{cc}$ are as defined herein).

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

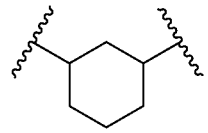 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

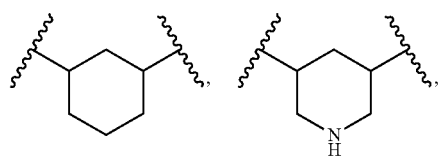

-continued

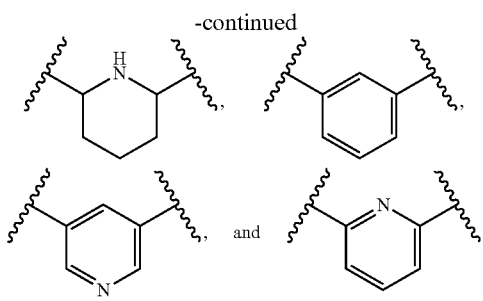

are all examples of a hydrocarbon chain. In contrast, in certain embodiments,

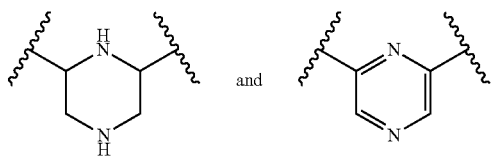 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

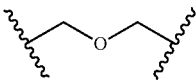

is a $C_3$ hydrocarbon chain wherein one chain atom is replaced with an oxygen atom.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs, pp.* 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The "molecular weight" of a monovalent moiety —R is calculated by subtracting 1 from the molecular weight of the compound R—H. The "molecular weight" of a divalent moiety -L- is calculated by subtracting 2 from the molecular weight of the compound H-L-H.

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is a fish or reptile. A "patient" refers to a human subject in need of treatment of a disease.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. These exemplary human protein kinases include, but are not limited to, AAK1, ABL, ACK, ACTR2, ACTR2B, AKT1, AKT2, AKT3, ALK, ALK1, ALK2, ALK4, ALK7, AMPKa1, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLIK1, CLIK1L, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRK1A, DYRK1B, DYRK2, DYRK3, DYRK4, EGFR, EphA1, EphA10, EphA2, EphA3, EphA4, EphA5, EphA6, EphA7, EphA8, EphB, EphB2, EphB3, EphB4, EphB6, Erk1, Erk2, Erk3, Erk3ps1, Erk3ps2, Erk3ps3, Erk3ps4, Erk4, Erk5, Erk7, FAK, FER, FERps, FES, FGFR1, FGFR2, FGFR3, FGFR4, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obscn, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAFlps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgKO50ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, WeeIB, WeeIBps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, and ZC4/NRK.

The term "inhibition", "inhibiting", "inhibit," or "inhibitor" refer to the ability of a compound to reduce, slow, halt, and/or prevent activity of a particular biological process (e.g., kinase activity) in a cell relative to vehicle.

When a compound, pharmaceutical composition, method, use, or kit is referred to as "selectively" or "specifically" modulating (e.g., increasing or inhibiting) the activity of a first protein kinase, the compound, pharmaceutical composition, method, use, or kit modulates the activity of the first protein kinase to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least a second protein kinase that is different from the first protein kinase.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomalleukemia, peripheral T-cell lymphoma (PTCL) (e.g., cutaneous T-cell lymphoma (CTCL) (e.g., mycosis fungoides, Sezary syndrome), angio-immunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemial-lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, rheumatoid arthritis, glomerulonephritis, Goodpasture's syndrome, necrotizing vasculitis, lymphadenitis, peri-arteritis nodosa, systemic lupus erythematosis, psoriatic arthritis, systemic lupus erythematosis, psoriasis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Reiter's syndrome, ankylosing spondylitis, Lyme disease, Guillain-Barré syndrome, Hashimoto's thyroiditis, and cardiomyopathy.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina *bifida*, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawl symptoms from drug addiction, joint pain, arthritic pain (e.g., pain associated with crystalline arthritis, osteoarthritis, psoriatic arthritis, gouty arthritis, reactive arthritis, or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the Diagnostic and Statistical Manual of Mental Disorders—Fourth Edition (DSM-IV), published by the American Psychiatric Association, Washington D.C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., type 1 diabetes, type 2 diabetes, gestational diabetes), hyperglycemia, hyperinsulinemia, insulin resistance, and obesity.

DETAILED DESCRIPTION OF CERTAIN EMBODIMENTS OF THE INVENTION

Described herein are imidazolyl compounds of Formula (I), and pharmaceutically acceptable salts, solvates, hydrates, polymorphs, co-crystals, tautomers, stereoisomers, isotopically labeled derivatives, and prodrugs thereof. Certain compounds described herein bind protein kinases and may be useful in modulating (e.g., inhibiting) the activity of a protein kinase in a subject or cell, in treating or preventing a disease (e.g., proliferative disease, genetic disease, hematological disease, neurological disease, painful condition, psychiatric disorder, or metabolic disorder) in a subject in need thereof, and/or in treating or preventing a disease or condition associated with aberrant kinase activity in a subject in need thereof. Also provided are pharmaceutical compositions and kits including a compound described herein.

Compounds

In one aspect, the present disclosure provides biheteroaryl compounds of Formula (I):

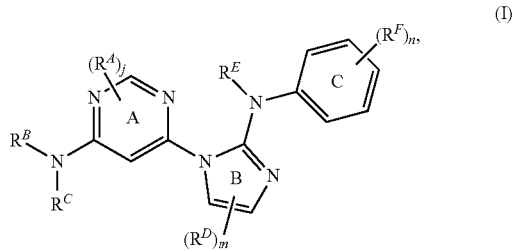

and pharmaceutically acceptable salts, solvates, hydrates, polymorphs, co-crystals, tautomers, stereoisomers, isotopically labeled derivatives, and prodrugs thereof, wherein:

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A1}$, $-N(R^{A1})_2$, $-SR^{A1}$, $-CN$, $-SCN$, $-C(=NR^{A1})R^{A1}$, $-C(=NR^{A1})OR^{A1}$, $-C(=NR^{A1})N(R^{A1})_2$, $-C(=O)R^{A1}$, $-C(=O)OR^{A1}$, $-C(=O)N(R^{A1})_2$, $-NO_2$, $-NR^{A1}C(=O)R^{A1}$, $-NR^{A1}C(=O)OR^{A1}$, $-NR^{A1}C(=O)N(R^{A1})_2$, $-OC(=O)R^{A1}$, $-OC(=O)OR^{A1}$, or $-OC(=O)N(R^{A1})_2$, wherein each instance of $R^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1}$ are joined to form a substituted or unsubstituted heterocyclic or substituted or unsubstituted heteroaryl ring;

j is 0, 1, or 2;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^C$ is hydrogen, substituted or unsubstituted acyl, substituted or unsubstituted $C_{1-6}$ alkyl, or a nitrogen protecting group;

each instance of $R^D$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{D1}$, $-N(R^{D1})_2$, $-SR^{D1}$, $-CN$, $-SCN$, $-C(=NR^{D1})R^{D1}$, $-C(=NR^{D1})OR^{D1}$, $-C(=NR^{D1})N(R^{D1})_2$, $-C(=O)R^{D1}$, $-C(=O)OR^{D1}$, $-C(=O)N(R^{D1})_2$, $-NO_2$, $-NR^{D1}C(=O)R^{D1}$, $-NR^{D1}C(=O)OR^{D1}$, $-NR^{D1}C(=O)N(R^{D1})_2$, $-OC(=O)R^{D1}$, $-OC(=O)OR^{D1}$, or $-OC(=O)N(R^{D1})_2$, wherein each instance of $R^{D1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{D1}$ are joined to form a substituted or unsubstituted heterocyclic or substituted or unsubstituted heteroaryl ring;

m is 0, 1, or 2;

$R^E$ is hydrogen, substituted or unsubstituted acyl, substituted or unsubstituted $C_{1-6}$ alkyl, or a nitrogen protecting group;

each instance of $R^F$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{F1}$, $-N(R^{F1})_2$, $-SR^{F1}$, $-CN$, $-SCN$, $-C(=NR^{F1})R^{F1}$, $-C(=NR^{F1})OR^{F1}$, $-C(=NR^{F1})N(R^{F1})_2$, $-C(=O)R^{F1}$, $-C(=O)OR^{F1}$, $-C(=O)N(R^{F1})_2$, $-NO_2$, $-NR^{F1}C(=O)R^{F1}$, $-NR^{F1}C(=O)OR^{F1}$, $-NR^{F1}C(=O)N(R^{F1})_2$, $-OC(=O)R^{F1}$, $-OC(=O)OR^{F1}$, or $-OC(=O)N(R^{F1})_2$, wherein each instance of $R^{F1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{F1}$ are joined to form a substituted or unsubstituted heterocyclic or substituted or unsubstituted heteroaryl ring; and n is 0, 1, 2, 3, 4, or 5.

Formula (I) includes as Ring A a pyrimidinyl ring that is unsubstituted (e.g., when j is 0) or substituted with one or two substituents $R^4$ (e.g., when j is 1 or 2). In certain embodiments, the two instances of $R^4$ are different. In certain embodiments, both instances of $R^4$ are the same. In certain embodiments, at least one instance of $R^4$ is halogen. In certain embodiments, at least one instance of $R^4$ is F. In certain embodiments, at least one instance of $R^4$ is Cl. In certain embodiments, at least one instance of $R^4$ is Br. In certain embodiments, at least one instance of $R^4$ is I (iodine). In certain embodiments, at least one instance of $R^4$ is substituted alkyl. In certain embodiments, at least one instance of $R^4$ is unsubstituted alkyl. In certain embodiments, at least one instance of $R^4$ is unsubstituted $C_{1-6}$ alkyl. In certain embodiments, both instances of $R^4$ are unsubstituted $C_{1-6}$ alkyl. In certain embodiments, at least one instance of $R^4$ is substituted $C_{1-6}$ alkyl. In certain embodiments, at least one instance of $R^4$ is $C_{1-6}$ alkyl substituted with at least one halogen. In certain embodiments, at least one instance of $R^4$ is —$CH_3$. In certain embodiments, at least one instance of $R^4$ is substituted methyl. In certain embodiments, at least one instance of $R^4$ is —$CH_2F$. In certain embodiments, at least one instance of $R^4$ is —$CHF_2$. In certain embodiments, at least one instance of $R^4$ is —$CF_3$. In certain embodiments, at least one instance of $R^4$ is ethyl. In certain embodiments, at least one instance of $R^4$ is propyl. In certain embodiments, at least one instance of $R^4$ is butyl. In certain embodiments, at least one instance of $R^4$ is pentyl. In certain embodiments, at least one instance of $R^4$ is hexyl. In certain embodiments, at least one instance of $R^4$ is halogen or substituted or unsubstituted $C_{1-6}$ alkyl. In certain embodiments, at least one instance of $R^4$ is substituted alkenyl. In certain embodiments, at least one instance of $R^4$ is unsubstituted alkenyl. In certain embodiments, at least one instance of $R^4$ is substituted alkynyl. In certain embodiments, at least one instance of $R^4$ is unsubstituted alkynyl. In certain embodiments, at least one instance of $R^4$ is substituted carbocyclyl. In certain embodiments, at least one instance of $R^4$ is unsubstituted carbocyclyl. In certain embodiments, at least one instance of $R^4$ is saturated carbocyclyl. In certain embodiments, at least one instance of $R^4$ is unsaturated carbocyclyl. In certain embodiments, at least one instance of $R^4$ is monocyclic carbocyclyl. In certain embodiments, at least one instance of $R^4$ is 3- to 7-membered, monocyclic carbocyclyl. In certain embodiments, at least one instance of $R^4$ is substituted heterocyclyl. In certain embodiments, at least one instance of $R^4$ is unsubstituted heterocyclyl. In certain embodiments, at least one instance of $R^4$ is saturated heterocyclyl. In certain embodiments, at least one instance of $R^4$ is unsaturated heterocyclyl. In certain embodiments, at least one instance of $R^4$ is heterocyclyl, wherein one, two, or three atoms of the heterocyclic ring system are independently selected from the group consisting of nitrogen, oxygen, and sulfur. In certain embodiments, at least one instance of $R^4$ is monocyclic heterocyclyl. In certain embodiments, at least one instance of $R^4$ is 3- to 7-membered, monocyclic heterocyclyl. In certain embodiments, at least one instance of $R^4$ is substituted aryl. In certain embodiments, at least one instance of $R^4$ is unsubstituted aryl. In certain embodiments, at least one instance of $R^4$ is 6- to 10-membered aryl. In certain embodiments, at least one instance of $R^4$ is substituted phenyl. In certain embodiments, at least one instance of $R^4$ is unsubstituted phenyl. In certain embodiments, at least one instance of $R^4$ is substituted heteroaryl. In certain embodiments, at least one instance of $R^4$ is unsubstituted heteroaryl. In certain embodiments, at least one instance of $R^4$ is heteroaryl, wherein one, two, three, or four atoms of the heteroaryl ring system are independently selected from the group consisting of nitrogen, oxygen, and sulfur. In certain embodiments, at least one instance of $R^4$ is monocyclic heteroaryl. In certain embodiments, at least one instance of $R^4$ is 5-membered, monocyclic heteroaryl. In certain embodiments, at least one instance of $R^4$ is 6-membered, monocyclic heteroaryl. In certain embodiments, at least one instance of $R^4$ is bicyclic heteroaryl, wherein the point of attachment may be on any atom of the bicyclic heteroaryl ring system, as valency permits. In certain embodiments, at least one instance of $R^4$ is 9- or 10-membered, bicyclic heteroaryl. In certain embodiments, at least one instance of $R^4$ is —$OR^{41}$. In certain embodiments, at least one instance of $R^4$ is —OH. In certain embodiments, at least one instance of $R^4$ is —O(substituted or unsubstituted $C_{1-6}$ alkyl). In certain embodiments, at least one instance of $R^4$ is —OMe. In certain embodiments, at least one instance of $R^4$ is —OEt. In certain embodiments, at least one instance of $R^4$ is —OPr. In certain embodiments, at least one instance of $R^4$ is —OBu. In certain embodiments, at least one instance of $R^4$ is —OBn. In certain embodiments, at least one instance of $R^4$ is —OPh. In certain embodiments, at least one instance of $R^4$ is —$SR^{41}$. In certain embodiments, at least one instance of $R^4$ is —SH. In certain embodiments, at least one instance of $R^4$ is —SMe. In certain embodiments, at least one instance of $R^4$ is —$N(R^{41})_2$. In certain embodiments, at least one instance of $R^4$ is —$NH_2$. In certain embodiments, at least one instance of $R^4$ is —NHMe. In certain embodiments, at least one instance of $R^4$ is —$NMe_2$. In certain embodiments, at least one instance of $R^4$ is —CN. In certain embodiments, at least one instance of $R^4$ is —SCN. In certain embodiments, at least one instance of $R^4$ is —$C(=NR^{41})R^{41}$, —$C(=NR^{41})OR^{41}$, or —$C(=NR^{41})N(R^{41})_2$. In certain embodiments, at least one instance of $R^4$ is —$C(=O)R^{41}$ or —$C(=O)OR^{41}$. In certain embodiments, at least one instance of $R^4$ is —$C(=O)N(R^{41})_2$. In certain embodiments, at least one instance of $R^4$ is —$C(=O)NMe_2$, —$C(=O)NHMe$, or —$C(=O)NH_2$. In certain embodiments, at least one instance of $R^4$ is —$NO_2$. In certain embodiments, at least one instance of $R^4$ is —$NR^{41}C(=O)R^{41}$, —$NR^{41}C(=O)OR^{41}$, or —$NR^{41}C(=O)N(R^{41})_2$. In certain embodiments, at least one instance of $R^4$ is —$OC(=O)R^{41}$, —$OC(=O)OR^{41}$, or —$OC(=O)N(R^{41})_2$.

In certain embodiments, at least one instance of $R^{41}$ is H. In certain embodiments, at least one instance of $R^{41}$ is substituted acyl. In certain embodiments, at least one instance of $R^{41}$ is unsubstituted acyl. In certain embodiments, at least one instance of $R^{41}$ is acetyl. In certain embodiments, at least one instance of $R^{41}$ is substituted alkyl. In certain embodiments, at least one instance of $R^{41}$ is unsubstituted alkyl. In certain embodiments, at least one instance of $R^{41}$ is unsubstituted $C_{1-6}$ alkyl. In certain embodiments, at least one instance of $R^{41}$ is methyl. In certain embodiments, at least one instance of $R^{41}$ is ethyl. In certain embodiments, at least one instance of $R^{41}$ is propyl. In certain embodiments, at least one instance of $R^{41}$ is butyl. In certain embodiments, at least one instance of $R^{41}$ is pentyl. In certain embodiments, at least one instance of $R^{41}$ is hexyl. In certain embodiments, at least one instance of $R^{41}$ is substituted alkenyl. In certain embodiments, at least one instance of $R^{A1}$ is unsubstituted alkenyl. In certain embodiments, at least one instance of $R^{A1}$ is substituted alkynyl. In certain embodiments, at least one instance of $R^{A1}$ is unsubstituted alkynyl. In certain embodiments, at least one instance of $R^{A1}$ is substituted or unsubstituted carbocyclyl. In certain embodiments, at least one instance of $R^{A1}$ is saturated carbocyclyl. In certain embodiments, at least one instance of $R^{A1}$ is unsaturated carbocyclyl. In certain embodiments, at least one instance of $R^{A1}$ is 3- to 7-membered, monocyclic carbocyclyl. In certain embodiments, at least one instance of $R^{A1}$ is substituted or unsubstituted heterocyclyl. In certain embodiments, at least one instance of $R^{A1}$ is saturated heterocyclyl. In certain embodiments, at least one instance of $R^{A1}$ is unsaturated heterocyclyl. In certain embodiments, at least one instance of $R^{A1}$ is heterocyclyl, wherein one, two, or three atoms of the heterocyclic ring system are independently selected from the group consisting of nitrogen, oxygen, and sulfur. In certain embodiments, at least one instance of $R^{A1}$ is 3- to 7-membered, monocyclic heterocyclyl. In certain embodiments, at least one instance of $R^{A1}$ is substituted or unsubstituted aryl. In certain embodiments, at least one instance of $R^{A1}$ is 6- to 10-membered aryl. In certain embodiments, at least one instance of $R^{A1}$ is monocyclic aryl. In certain embodiments, at least one instance of $R^{A1}$ is substituted phenyl. In certain embodiments, at least one instance of $R^{A1}$ is unsubstituted phenyl. In certain embodiments, at least one instance of $R^{A1}$ is bicyclic aryl. In certain embodiments, at least one instance of $R^{A1}$ is substituted or unsubstituted heteroaryl. In certain embodiments, at least one instance of $R^{A1}$ is heteroaryl, wherein one, two, three, or four atoms of the heteroaryl ring system are independently selected from the group consisting of nitrogen, oxygen, and sulfur. In certain embodiments, at least one instance of $R^{A1}$ is monocyclic heteroaryl. In certain embodiments, at least one instance of $R^{A1}$ is 5- or 6-membered, monocyclic heteroaryl. In certain embodiments, at least one instance of $R^{A1}$ is bicyclic heteroaryl, wherein the point of attachment may be on any atom of the bicyclic heteroaryl ring system, as valency permits. In certain embodiments, at least one instance of $R^{A1}$ is a nitrogen protecting group when attached to a nitrogen atom. In certain embodiments, at least one instance of $R^{A1}$ is Bn, Boc, Cbz, Fmoc, trifluoroacetyl, triphenylmethyl, acetyl, or Ts when attached to a nitrogen atom. In certain embodiments, $R^{A1}$ is an oxygen protecting group when attached to an oxygen atom. In certain embodiments, $R^{A1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{A1}$ is a sulfur protecting group when attached to a sulfur atom. In certain embodiments, $R^{A1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{A1}$ are joined to form a substituted or unsubstituted heterocyclic ring. In certain embodiments, two instances of $R^{A1}$ are joined to form a saturated or unsaturated heterocyclic ring. In certain embodiments, two instances of $R^{A1}$ are joined to form a heterocyclic ring, wherein one, two, or three atoms of the heterocyclic ring system are independently selected from the group consisting of nitrogen, oxygen, and sulfur. In certain embodiments, two instances of $R^{A1}$ are joined to form a 3- to 7-membered, monocyclic heterocyclic ring. In certain embodiments, two instances of $R^{A1}$ are joined to form a substituted or unsubstituted heteroaryl ring. In certain embodiments, two instances of $R^{A1}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

In certain embodiments, j is 0. In certain embodiments, j is 1. In certain embodiments, j is 2.

Formula (I) includes substituent $R^B$ on a nitrogen atom. In certain embodiments, $R^B$ is H. In certain embodiments, $R^B$ is substituted acyl. In certain embodiments, $R^B$ is unsubstituted acyl. In certain embodiments, $R^B$ is acetyl. In certain embodiments, $R^B$ is substituted alkyl. In certain embodiments, $R^B$ is unsubstituted alkyl. In certain embodiments, $R^B$ is unsubstituted $C_{1-6}$ alkyl. In certain embodiments, $R^B$ is substituted $C_{1-6}$ alkyl. In certain embodiments, $R^B$ is $C_{1-6}$ alkyl substituted with at least one halogen. In certain embodiments, $R^B$ is —$CH_3$. In certain embodiments, $R^B$ is substituted methyl. In certain embodiments, $R^B$ is —$CH_2F$. In certain embodiments, $R^B$ is —$CHF_2$. In certain embodiments, $R^B$ is —$CF_3$. In certain embodiments, $R^B$ is ethyl. In certain embodiments, $R^B$ is propyl. In certain embodiments, $R^B$ is butyl. In certain embodiments, $R^B$ is pentyl. In certain embodiments, $R^B$ is hexyl. In certain embodiments, $R^B$ is —$(CH_2)_{1-4}$-(Ring F), wherein Ring F is a substituted or unsubstituted, 3- to 7-membered, monocyclic heterocyclic ring. In certain embodiments, $R^B$ is —$(CH_2)_{1-4}$-(substituted or unsubstituted pyrrolidinyl). In certain embodiments, $R^B$ is of the formula:

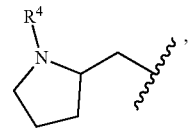

wherein $R^4$ is H, substituted or unsubstituted $C_{1-6}$ alkyl, or a nitrogen protecting group. In certain embodiments, $R^B$ is of the formula:

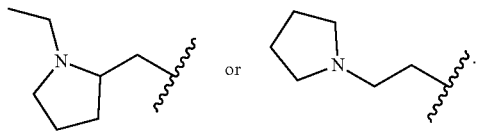

In certain embodiments, $R^B$ is —$(CH_2)_{1-4}$-(Ring F), wherein Ring F is a substituted or unsubstituted oxetanyl, substituted or unsubstituted azetidinyl, substituted or unsubstituted tetrahydrofuranyl, substituted or unsubstituted tetrahydropyranyl, substituted or unsubstituted piperidinyl, substituted or unsubstituted piperazinyl, or substituted or unsubstituted morpholinyl ring. In certain embodiments, $R^B$ is substituted alkenyl. In certain embodiments, $R^B$ is unsubstituted alkenyl. In certain embodiments, $R^B$ is substituted alkynyl. In certain embodiments, $R^B$ is unsubstituted alkynyl. In certain embodiments, $R^B$ is substituted carbocyclyl. In certain embodiments, $R^B$ is unsubstituted carbocyclyl. In certain embodiments, $R^B$ is saturated carbocyclyl. In certain embodiments, $R^B$ is unsaturated carbocyclyl. In certain embodiments, $R^B$ is monocyclic carbocyclyl. In certain embodiments, $R^B$ is 3- to 7-membered, monocyclic carbocyclyl. In certain embodiments, $R^B$ is unsubstituted cyclopropyl. In certain embodiments, $R^B$ is substituted cyclopropyl. In certain embodiments, $R^B$ is substituted heterocyclyl. In certain embodiments, $R^B$ is unsubstituted heterocyclyl. In certain embodiments, $R^B$ is saturated heterocyclyl. In certain embodiments, $R^B$ is unsaturated heterocyclyl. In certain embodiments, $R^B$ is heterocyclyl, wherein one, two, or three atoms of the heterocyclic ring system are independently selected from the group consisting of nitrogen, oxygen, and sulfur. In certain embodiments, $R^B$ is monocyclic heterocyclyl. In certain embodiments, $R^B$ is 3- to 7-membered, monocyclic heterocyclyl. In certain embodiments, $R^B$ is substituted aryl. In certain embodiments, $R^B$ is unsubstituted aryl. In certain embodiments, $R^B$ is 6- to 10-membered aryl. In certain embodiments, $R^B$ is substituted phenyl. In certain embodiments, $R^B$ is unsubstituted phenyl. In certain embodiments, $R^B$ is substituted or unsubstituted, 5- to 6-membered, monocyclic heteroaryl, wherein one, two, three, or four atoms of the heteroaryl ring system are independently nitrogen, oxygen, or sulfur. In certain embodiments, $R^B$ is substituted or unsubstituted pyrazolyl. In certain embodiments, $R^B$ is of the formula:

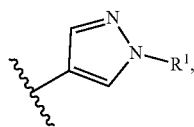

wherein $R^1$ is H, substituted or unsubstituted $C_{1-6}$ alkyl, or a nitrogen protecting group. In certain embodiments, $R^B$ is of the formula:

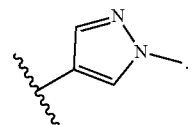 [SMILES: *c1cnn(C)c1]

In certain embodiments, $R^B$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, $R^B$ is substituted or unsubstituted pyridyl, substituted or unsubstituted pyrazinyl, substituted or unsubstituted pyrimidinyl, or substituted or unsubstituted pyridazinyl. In certain embodiments, $R^B$ is substituted or unsubstituted, 9- to 10-membered, bicyclic heteroaryl, wherein one, two, three, or four atoms of the heteroaryl ring system are independently nitrogen, oxygen, or sulfur. In certain embodiments, $R^B$ is a nitrogen protecting group. In certain embodiments, $R^B$ is Bn, Boc, Cbz, Fmoc, trifluoroacetyl, triphenylmethyl, acetyl, or Ts.

Formula (I) includes substituent $R^C$ on a nitrogen atom. In certain embodiments, $R^C$ is H. In certain embodiments, $R^C$ is substituted acyl. In certain embodiments, $R^C$ is unsubstituted acyl. In certain embodiments, $R^C$ is acetyl. In certain embodiments, $R^C$ is unsubstituted $C_{1-6}$ alkyl. In certain embodiments, $R^C$ is substituted $C_{1-6}$ alkyl. In certain embodiments, $R^C$ is $C_{1-6}$ alkyl substituted with at least one halogen. In certain embodiments, $R^C$ is unsubstituted methyl. In certain embodiments, $R^C$ is substituted methyl. In certain embodiments, $R^C$ is —$CH_2F$. In certain embodiments, $R^C$ is —$CHF_2$. In certain embodiments, $R^C$ is —$CF_3$. In certain embodiments, $R^C$ is ethyl. In certain embodiments, $R^C$ is propyl. In certain embodiments, $R^C$ is butyl. In certain embodiments, $R^C$ is pentyl. In certain embodiments, $R^C$ is hexyl. In certain embodiments, $R^C$ is a nitrogen protecting group. In certain embodiments, $R^C$ is Bn, Boc, Cbz, Fmoc, trifluoroacetyl, triphenylmethyl, acetyl, or Ts.

In certain embodiments, $R^B$ is substituted or unsubstituted $C_{1-6}$ alkyl, and $R^C$ is H. In certain embodiments, $R^B$ is —$(CH_2)_{1-4}$-(Ring F), wherein Ring F is a substituted or unsubstituted, 3- to 7-membered, monocyclic heterocyclic ring; and $R^C$ is H. In certain embodiments, $R^B$ is substituted or unsubstituted phenyl (e.g., para-substituted phenyl), and $R^C$ is H. In certain embodiments, $R^B$ is substituted or unsubstituted, 5- to 6-membered, monocyclic heteroaryl, wherein one, two, three, or four atoms of the heteroaryl ring system are independently nitrogen, oxygen, or sulfur; and $R^C$ is H. In certain embodiments, $R^B$ is substituted or unsubstituted pyrazolyl, and $R^C$ is H. In certain embodiments, $R^B$ is substituted or unsubstituted, 3- to 7-membered, monocyclic carbocyclyl; and $R^C$ is H. In certain embodiments, $R^B$ is substituted or unsubstituted cyclopropyl, and $R^C$ is H.

Formula (I) includes as Ring B an imidazolyl ring that is unsubstituted (e.g., when m is 0) or substituted with one or two substituents $R^D$ (e.g., when m is 1 or 2). In certain embodiments, Ring B does not include substituents $R^D$, that is, m is 0. In certain embodiments, the two instances of $R^D$ are different. In certain embodiments, both instances of $R^D$ are the same. In certain embodiments, at least one instance of $R^D$ is halogen. In certain embodiments, at least one instance of $R^D$ is F. In certain embodiments, at least one instance of $R^D$ is Cl. In certain embodiments, at least one instance of $R^D$ is Br. In certain embodiments, at least one instance of $R^D$ is I (iodine). In certain embodiments, at least one instance of $R^D$ is substituted alkyl. In certain embodiments, at least one instance of $R^D$ is unsubstituted alkyl. In certain embodiments, at least one instance of $R^D$ is unsubstituted $C_{1-6}$ alkyl. In certain embodiments, both instances of $R^D$ are unsubstituted $C_{1-6}$ alkyl. In certain embodiments, at least one instance of $R^D$ is substituted $C_{1-6}$ alkyl. In certain embodiments, at least one instance of $R^D$ is $C_{1-6}$ alkyl substituted with at least one halogen. In certain embodiments, at least one instance of $R^D$ is —$CH_3$. In certain embodiments, at least one instance of $R^D$ is substituted methyl. In certain embodiments, at least one instance of $R^D$ is —$CH_2F$. In certain embodiments, at least one instance of $R^D$ is —$CHF_2$. In certain embodiments, at least one instance of $R^D$ is —$CF_3$. In certain embodiments, at least one instance of $R^D$ is ethyl. In certain embodiments, at least one instance of $R^D$ is propyl. In certain embodiments, at least one instance of $R^D$ is butyl. In certain embodiments, at least one instance of $R^D$ is pentyl. In certain embodiments, at least one instance of $R^D$ is hexyl. In certain embodiments, at least one instance of $R^D$ is halogen or substituted or unsubstituted $C_{1-6}$ alkyl. In certain embodiments, at least one instance of $R^D$ is substituted alkenyl. In certain embodiments, at least one instance of $R^D$ is unsubstituted alkenyl. In certain embodiments, at least one instance of $R^D$ is substituted alkynyl. In certain embodiments, at least one instance of $R^D$ is unsubstituted alkynyl. In certain embodiments, at least one instance of $R^D$ is substituted carbocyclyl. In certain embodiments, at least one instance of $R^D$ is unsubstituted carbocyclyl. In certain embodiments, at least one instance of $R^D$ is saturated carbocyclyl. In certain embodiments, at least one instance of $R^D$ is unsaturated carbocyclyl. In certain embodiments, at least one instance of $R^D$ is monocyclic carbocyclyl. In certain embodiments, at least one instance of $R^D$ is 3- to 7-membered, monocyclic carbocyclyl. In certain embodiments, at least one instance of $R^D$ is substituted heterocyclyl. In certain embodiments, at least one instance of $R^D$ is unsubstituted heterocyclyl. In certain embodiments, at least one instance of $R^D$ is saturated heterocyclyl. In certain embodiments, at least one instance of $R^D$ is unsaturated heterocyclyl. In certain embodiments, at least one instance of $R^D$ is heterocyclyl, wherein one, two, or three atoms of the heterocyclic ring system are independently selected from the group consisting of nitrogen, oxygen, and sulfur. In certain embodiments, at least one instance of $R^D$ is monocyclic heterocyclyl. In certain embodiments, at least one instance of $R^D$ is 3- to 7-membered, monocyclic heterocyclyl. In certain embodiments, at least one instance of $R^D$ is substituted aryl. In certain embodiments, at least one instance of $R^D$ is unsubstituted aryl. In certain embodiments, at least one instance of $R^D$ is 6- to 10-membered aryl. In certain embodiments, at least one instance of $R^D$ is substituted phenyl. In certain embodiments, at least one instance of $R^D$ is unsubstituted phenyl. In certain embodiments, at least one instance of $R^D$ is substituted heteroaryl. In certain embodiments, at least one instance of $R^D$ is unsubstituted heteroaryl. In certain embodiments, at least one instance of $R^D$ is heteroaryl, wherein one, two, three, or four atoms of the heteroaryl ring system are independently selected from the group consisting of nitrogen, oxygen, and sulfur. In certain embodiments, at least one instance of $R^D$ is monocyclic heteroaryl. In certain embodiments, at least one instance of $R^D$ is 5-membered, monocyclic heteroaryl. In certain embodiments, at least one instance of $R^D$ is 6-membered, monocyclic heteroaryl. In certain embodiments, at least one instance of $R^D$ is bicyclic heteroaryl, wherein the point of attachment may be on any atom of the bicyclic heteroaryl ring system, as valency permits. In certain embodiments, at least one instance of $R^D$ is 9- or 10-membered, bicyclic heteroaryl. In certain embodiments, at least one instance of $R^D$ is —$OR^{D1}$. In certain embodiments, at least one instance of $R^D$ is —OH. In certain embodiments, at least one instance of $R^D$ is —O(substituted or unsubstituted $C_{1-6}$ alkyl). In certain embodiments, at least one instance of $R^D$ is —OMe. In certain embodiments, at least one instance of $R^D$ is —OEt. In certain embodiments, at least one instance of $R^D$ is —OPr. In certain embodiments, at least one instance of $R^D$ is —OBu. In certain embodiments, at least one instance of $R^D$ is —OBn. In certain embodiments, at least one instance of $R^D$ is —OPh. In certain embodiments, at least one instance of $R^D$ is —$SR^{D1}$. In certain embodiments, at least one instance of $R^D$ is —SH. In certain embodiments, at least one instance of $R^D$ is —SMe. In certain embodiments, at least one instance of $R^D$ is —$N(R^{D1})_2$. In certain embodiments, at least one instance of $R^D$ is —$NH_2$. In certain embodiments, at least one instance of $R^D$ is —NHMe. In certain embodiments, at least one instance of $R^D$ is —$NMe_2$. In certain embodiments, at least one instance of $R^D$ is —CN. In certain embodiments, at least one instance of $R^D$ is —SCN. In certain embodiments, at least one instance of $R^D$ is —C(=$NR^{D1}$)$R^{D1}$, —C(=$NR^{D1}$)$OR^{D1}$, or —C(=$NR^{D1}$)$N(R^{D1})_2$. In certain embodiments, at least one instance of $R^D$ is —C(=O)$R^{D1}$ or —C(=O)$OR^{D1}$. In certain embodiments, at least one instance of $R^D$ is —C(=O)$N(R^{D1})_2$. In certain embodiments, at least one instance of $R^D$ is —C(=O)$NMe_2$, —C(=O)NHMe, or —C(=O)$NH_2$. In certain embodiments, at least one instance of $R^D$ is —$NO_2$. In certain embodiments, at least one instance of $R^D$ is —$NR^{D1}$C(=O)$R^{D1}$, —$NR^{D1}$C(=O)$OR^{D1}$, or —$NR^{D1}$C(=O)$N(R^{D1})_2$. In certain embodiments, at least one instance of $R^D$ is —OC(=O)$R^{D1}$, —OC(=O)$OR^{D1}$, or —OC(=O)$N(R^{D1})_2$.

In certain embodiments, at least one instance of $R^{D1}$ is H. In certain embodiments, at least one instance of $R^{D1}$ is substituted acyl. In certain embodiments, at least one instance of $R^{D1}$ is unsubstituted acyl. In certain embodiments, at least one instance of $R^{D1}$ is acetyl. In certain embodiments, at least one instance of $R^{D1}$ is substituted alkyl. In certain embodiments, at least one instance of $R^{D1}$ is unsubstituted alkyl. In certain embodiments, at least one instance of $R^{D1}$ is unsubstituted $C_{1-6}$ alkyl. In certain embodiments, at least one instance of $R^{D1}$ is methyl. In certain embodiments, at least one instance of $R^{D1}$ is ethyl. In certain embodiments, at least one instance of $R^{D1}$ is propyl. In certain embodiments, at least one instance of $R^{D1}$ is butyl. In certain embodiments, at least one instance of $R^{D1}$ is pentyl. In certain embodiments, at least one instance of $R^{D1}$ is hexyl. In certain embodiments, at least one instance of $R^{D1}$ is substituted alkenyl. In certain embodiments, at least one instance of $R^{D1}$ is unsubstituted alkenyl. In certain embodiments, at least one instance of $R^{D1}$ is substituted alkynyl. In certain embodiments, at least one instance of $R^{D1}$ is unsubstituted alkynyl. In certain embodiments, at least one instance of $R^{D1}$ is substituted or unsubstituted carbocyclyl. In certain embodiments, at least one instance of $R^{D1}$ is saturated carbocyclyl. In certain embodiments, at least one instance of $R^{D1}$ is unsaturated carbocyclyl. In certain embodiments, at least one instance of $R^{D1}$ is 3- to 7-membered, monocyclic carbocyclyl. In certain embodiments, at least one instance of $R^{D1}$ is substituted or unsubstituted heterocyclyl. In certain embodiments, at least one instance of $R^{D1}$ is saturated heterocyclyl. In certain embodiments, at least one instance of $R^{D1}$ is unsaturated heterocyclyl. In certain embodiments, at least one instance of $R^{D1}$ is heterocyclyl, wherein one, two, or three atoms of the heterocyclic ring system are independently selected from the group consisting of nitrogen, oxygen, and sulfur. In certain embodiments, at least one instance of $R^{D1}$ is 3- to 7-membered, monocyclic heterocyclyl. In certain embodiments, at least one instance of $R^{D1}$ is substituted or unsubstituted aryl. In certain embodiments, at least one instance of $R^{D1}$ is 6- to 10-membered aryl. In certain embodiments, at least one instance of $R^{D1}$ is monocyclic aryl. In certain embodiments, at least one instance of $R^{D1}$ is substituted phenyl. In certain embodiments, at least one instance of $R^{D1}$ is unsubstituted phenyl. In certain embodiments, at least one instance of $R^{D1}$ is bicyclic aryl. In certain embodiments, at least one instance of $R^{D1}$ is substituted or unsubstituted heteroaryl. In certain embodiments, at least one instance of $R^{D1}$ is heteroaryl, wherein one, two, three, or four atoms of the heteroaryl ring system are independently selected from the group consisting of nitrogen, oxygen, and sulfur. In certain embodiments, at least one instance of $R^{D1}$ is monocyclic heteroaryl. In certain embodiments, at least one instance of $R^{D1}$ is 5- or 6-membered, monocyclic heteroaryl. In certain embodiments, at least one instance of $R^{D1}$ is bicyclic heteroaryl, wherein the point of attachment may be on any atom of the bicyclic heteroaryl ring system, as valency permits. In certain embodiments, at least one instance of $R^{D1}$ is a nitrogen protecting group when attached to a nitrogen atom. In certain embodiments, at least one instance of $R^{D1}$ is Bn, Boc, Cbz, Fmoc, trifluoroacetyl, triphenylmethyl, acetyl, or Ts when attached to a nitrogen atom. In certain embodiments, $R^{D1}$ is an oxygen protecting group when attached to an oxygen atom. In certain embodiments, $R^{D1}$ is silyl, TBDPS, TBDMS, TIPS, TES, TMS, MOM, THP, t-Bu, Bn, allyl, acetyl, pivaloyl, or benzoyl when attached to an oxygen atom.

In certain embodiments, $R^{D1}$ is a sulfur protecting group when attached to a sulfur atom. In certain embodiments, $R^{D1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{D1}$ are joined to form a substituted or unsubstituted heterocyclic ring. In certain embodiments, two instances of $R^{D1}$ are joined to form a saturated or unsaturated heterocyclic ring. In certain embodiments, two instances of $R^{D1}$ are joined to form a heterocyclic ring, wherein one, two, or three atoms of the heterocyclic ring system are independently selected from the group consisting of nitrogen, oxygen, and sulfur. In certain embodiments, two instances of $R^{D1}$ are joined to form a 3- to 7-membered, monocyclic heterocyclic ring. In certain embodiments, two instances of $R^{D1}$ are joined to form a substituted or unsubstituted heteroaryl ring. In certain embodiments, two instances of $R^{D1}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

In certain embodiments, m is 0. In certain embodiments, m is 1. In certain embodiments, m is 2.

Formula (I) includes substituent $R^E$ on a nitrogen atom. In certain embodiments, $R^E$ is H. In certain embodiments, $R^E$ is substituted acyl. In certain embodiments, $R^E$ is unsubstituted acyl. In certain embodiments, $R^E$ is acetyl. In certain embodiments, $R^E$ is unsubstituted $C_{1-6}$ alkyl. In certain embodiments, $R^E$ is substituted $C_{1-6}$ alkyl. In certain embodiments, $R^E$ is $C_{1-6}$ alkyl substituted with at least one halogen. In certain embodiments, $R^E$ is unsubstituted methyl. In certain embodiments, $R^E$ is substituted methyl. In certain embodiments, $R^E$ is —$CH_2F$. In certain embodiments, $R^E$ is —$CHF_2$. In certain embodiments, $R^E$ is —$CF_3$. In certain embodiments, $R^E$ is ethyl. In certain embodiments, $R^E$ is propyl. In certain embodiments, $R^E$ is butyl. In certain embodiments, $R^E$ is pentyl. In certain embodiments, $R^E$ is hexyl. In certain embodiments, $R^E$ is a nitrogen protecting group. In certain embodiments, $R^E$ is Bn, Boc, Cbz, Fmoc, trifluoroacetyl, triphenylmethyl, acetyl, or Ts.

In certain embodiments, each of $R^C$ and $R^E$ is H.

Formula (I) includes as Ring C a phenyl ring that is unsubstituted (e.g., when n is 0) or substituted with one or more substituents RF (e.g., when n is 1, 2, 3, 4, or 5). In certain embodiments, Ring C is of the formula:

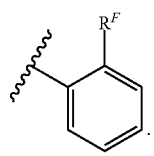

In certain embodiments, Ring C is of the formula:

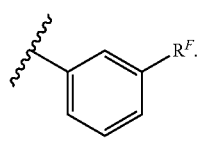

In certain embodiments, Ring C is of the formula:

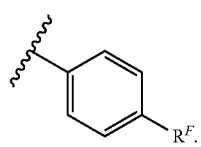

In certain embodiments, Ring C is of the formula:

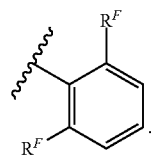

In certain embodiments, Ring C is of the formula:

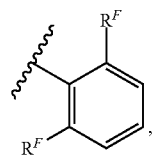

wherein each instance of $R^F$ is independently halogen or substituted or unsubstituted $C_{1-6}$ alkyl. In certain embodiments, Ring C is of the formula:

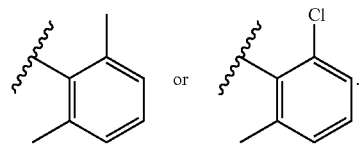

In certain embodiments, Ring C is of the formula:

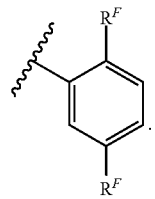

In certain embodiments, Ring C is of the formula:

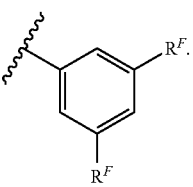

In certain embodiments, Ring C is of the formula:

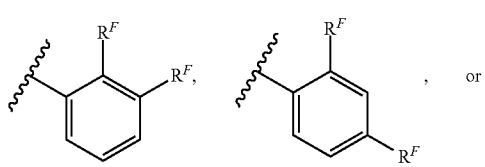

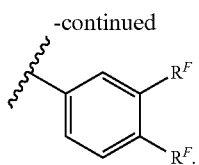

In certain embodiments, at least two instances of $R^F$ are different. In certain embodiments, all instances of $R^F$ are the same. In certain embodiments, at least one instance of $R^F$ is halogen. In certain embodiments, at least one instance of $R^F$ is F. In certain embodiments, at least one instance of $R^F$ is Cl. In certain embodiments, at least one instance of $R^F$ is Br. In certain embodiments, at least one instance of $R^F$ is I (iodine). In certain embodiments, at least one instance of $R^F$ is substituted alkyl. In certain embodiments, at least one instance of $R^F$ is unsubstituted alkyl. In certain embodiments, at least one instance of $R^F$ is unsubstituted $C_{1-6}$ alkyl. In certain embodiments, all instances of $R^F$ are unsubstituted $C_{1-6}$ alkyl. In certain embodiments, at least one instance of $R^F$ is substituted $C_{1-6}$ alkyl. In certain embodiments, at least one instance of $R^F$ is $C_{1-6}$ alkyl substituted with at least one halogen. In certain embodiments, at least one instance of $R^F$ is —$CH_3$. In certain embodiments, all instances of $R^F$ are —$CH_3$. In certain embodiments, at least one instance of $R^F$ is substituted methyl. In certain embodiments, at least one instance of $R^F$ is —$CH_2F$. In certain embodiments, at least one instance of $R^F$ is —$CHF_2$. In certain embodiments, at least one instance of $R^F$ is —$CF_3$. In certain embodiments, at least one instance of $R^F$ is ethyl. In certain embodiments, at least one instance of $R^F$ is propyl. In certain embodiments, at least one instance of $R^F$ is butyl. In certain embodiments, at least one instance of $R^F$ is pentyl. In certain embodiments, at least one instance of $R^F$ is hexyl. In certain embodiments, at least one instance of $R^F$ is substituted alkenyl. In certain embodiments, at least one instance of $R^F$ is unsubstituted alkenyl. In certain embodiments, at least one instance of $R^F$ is substituted alkynyl. In certain embodiments, at least one instance of $R^F$ is unsubstituted alkynyl. In certain embodiments, at least one instance of $R^F$ is substituted carbocyclyl. In certain embodiments, at least one instance of $R^F$ is unsubstituted carbocyclyl. In certain embodiments, at least one instance of $R^F$ is saturated carbocyclyl. In certain embodiments, at least one instance of $R^F$ is unsaturated carbocyclyl. In certain embodiments, at least one instance of $R^F$ is monocyclic carbocyclyl. In certain embodiments, at least one instance of $R^F$ is 3- to 7-membered, monocyclic carbocyclyl. In certain embodiments, at least one instance of $R^F$ is substituted heterocyclyl. In certain embodiments, at least one instance of $R^F$ is unsubstituted heterocyclyl. In certain embodiments, at least one instance of $R^F$ is saturated heterocyclyl. In certain embodiments, at least one instance of $R^F$ is unsaturated heterocyclyl. In certain embodiments, at least one instance of $R^F$ is heterocyclyl, wherein one, two, or three atoms of the heterocyclic ring system are independently selected from the group consisting of nitrogen, oxygen, and sulfur. In certain embodiments, at least one instance of $R^F$ is monocyclic heterocyclyl. In certain embodiments, at least one instance of $R^F$ is 3- to 7-membered, monocyclic heterocyclyl. In certain embodiments, at least one instance of $R^F$ is substituted aryl. In certain embodiments, at least one instance of $R^F$ is unsubstituted aryl. In certain embodiments, at least one instance of $R^F$ is 6- to 10-membered aryl. In certain embodiments, at least one instance of $R^F$ is substituted phenyl. In certain embodiments, at least one instance of $R^F$ is unsubstituted phenyl. In certain embodiments, at least one instance of $R^F$ is substituted heteroaryl. In certain embodiments, at least one instance of $R^F$ is unsubstituted heteroaryl. In certain embodiments, at least one instance of $R^F$ is heteroaryl, wherein one, two, three, or four atoms of the heteroaryl ring system are independently selected from the group consisting of nitrogen, oxygen, and sulfur. In certain embodiments, at least one instance of $R^F$ is monocyclic heteroaryl. In certain embodiments, at least one instance of $R^F$ is 5-membered, monocyclic heteroaryl. In certain embodiments, at least one instance of $R^F$ is 6-membered, monocyclic heteroaryl. In certain embodiments, at least one instance of $R^F$ is bicyclic heteroaryl, wherein the point of attachment may be on any atom of the bicyclic heteroaryl ring system, as valency permits. In certain embodiments, at least one instance of $R^F$ is 9- or 10-membered, bicyclic heteroaryl. In certain embodiments, at least one instance of $R^F$ is —$OR^{F1}$. In certain embodiments, at least one instance of $R^F$ is —OH. In certain embodiments, at least one instance of $R^F$ is —O(substituted or unsubstituted $C_{1-6}$ alkyl). In certain embodiments, at least one instance of $R^F$ is —OMe. In certain embodiments, at least one instance of $R^F$ is —OEt. In certain embodiments, at least one instance of $R^F$ is —OPr. In certain embodiments, at least one instance of $R^F$ is —OBu. In certain embodiments, at least one instance of $R^F$ is —OBn. In certain embodiments, at least one instance of $R^F$ is —OPh. In certain embodiments, at least one instance of $R^F$ is —$SR^{F1}$. In certain embodiments, at least one instance of $R^F$ is —SH. In certain embodiments, at least one instance of $R^F$ is —SMe. In certain embodiments, at least one instance of $R^F$ is —$N(R^{F1})_2$. In certain embodiments, at least one instance of $R^F$ is —$NH_2$. In certain embodiments, at least one instance of $R^F$ is —NHMe. In certain embodiments, at least one instance of $R^F$ is —$NMe_2$. In certain embodiments, at least one instance of $R^F$ is —CN. In certain embodiments, at least one instance of $R^F$ is —SCN. In certain embodiments, at least one instance of $R^F$ is —$C(=NR^{F1})R^{F1}$, —$C(=NR^{F1})OR^{F1}$, or —$C(=NR^{F1})N(R^{F1})_2$. In certain embodiments, at least one instance of $R^F$ is —$C(=O)R^{F1}$ or —$C(=O)OR^{F1}$. In certain embodiments, at least one instance of $R^F$ is —$C(=O)N(R^{F1})_2$.

In certain embodiments, at least one instance of $R^F$ is —$C(=O)N(R^{F1})_2$, wherein each instance of $R^{F1}$ is independently hydrogen, substituted or unsubstituted $C_{1-6}$ alkyl, substituted or unsubstituted phenyl, or a nitrogen protecting group. In certain embodiments, at least one instance of $R^F$ is —$C(=O)NHR^{F1}$, wherein $R^{F1}$ is substituted or unsubstituted phenyl. In certain embodiments, at least one instance of $R^F$ is —$C(=O)NHR^{F1}$, wherein $R^{F1}$ is phenyl substituted with one, two, three, four, or five substituents independently selected from the group consisting of halogen and substituted or unsubstituted $C_{1-6}$ alkyl. In certain embodiments, at least one instance of $R^F$ is —$C(=O)NMeR^{F1}$, wherein $R^{F1}$ is substituted or unsubstituted phenyl. In certain embodiments, at least one instance of $R^F$ is —$C(=O)NMeR^{F1}$, wherein $R^{F1}$ is phenyl substituted with one, two, three, four, or five substituents independently selected from the group consisting of halogen and substituted or unsubstituted $C_{1-6}$ alkyl. In certain embodiments, at least one instance of $R^F$ is —$C(=O)NMe_2$, —$C(=O)NHMe$, or —$C(=O)NH_2$. In certain embodiments, at least one instance of $R^F$ is —$NO_2$. In certain embodiments, at least one instance of $R^F$ is —$NR^{F1}C(=O)R^{F1}$, —$NR^{F1}C(=O)OR^{F1}$, or —$NR^{F1}C(=O)N(R^{F1})_2$. In certain embodiments, at least one instance of $R^F$ is —$OC(=O)R^{F1}$, —$OC(=O)OR^{F1}$, or —$OC(=O)N(R^{F1})_2$.

In certain embodiments, at least one instance of $R^F$ is halogen, substituted or unsubstituted $C_{1-6}$ alkyl, or —$OR^{F1}$. In certain embodiments, at least one instance of $R^F$ is halogen, substituted or unsubstituted $C_{1-6}$ alkyl, or —$OR^{F1}$, wherein $R^{F1}$ is hydrogen, substituted or unsubstituted $C_{1-6}$ alkyl, or an oxygen protecting group. In certain embodiments, at least one instance of $R^F$ is halogen, unsubstituted $C_{1-6}$ alkyl, or —$OR^{F1}$, wherein $R^{F1}$ is unsubstituted $C_{1-6}$ alkyl. In certain embodiments, at least one instance of $R^F$ is —$CH_3$ or Cl.

In certain embodiments, at least one instance of $R^{F1}$ is H. In certain embodiments, at least one instance of $R^{F1}$ is substituted acyl. In certain embodiments, at least one instance of $R^{F1}$ is unsubstituted acyl. In certain embodiments, at least one instance of $R^{F1}$ is acetyl. In certain embodiments, at least one instance of $R^{F1}$ is substituted alkyl. In certain embodiments, at least one instance of $R^{F1}$ is unsubstituted alkyl. In certain embodiments, at least one instance of $R^{F1}$ is unsubstituted $C_{1-6}$ alkyl. In certain embodiments, at least one instance of $R^{F1}$ is methyl. In certain embodiments, at least one instance of $R^{F1}$ is ethyl. In certain embodiments, at least one instance of $R^{F1}$ is propyl. In certain embodiments, at least one instance of $R^{F1}$ is butyl. In certain embodiments, at least one instance of $R^{F1}$ is pentyl. In certain embodiments, at least one instance of $R^{F1}$ is hexyl. In certain embodiments, at least one instance of $R^{F1}$ is substituted alkenyl. In certain embodiments, at least one instance of $R^{F1}$ is unsubstituted alkenyl. In certain embodiments, at least one instance of $R^{F1}$ is substituted alkynyl. In certain embodiments, at least one instance of $R^{F1}$ is unsubstituted alkynyl. In certain embodiments, at least one instance of $R^{F1}$ is substituted or unsubstituted carbocyclyl. In certain embodiments, at least one instance of $R^{F1}$ is saturated carbocyclyl. In certain embodiments, at least one instance of $R^{F1}$ is unsaturated carbocyclyl. In certain embodiments, at least one instance of $R^{F1}$ is 3- to 7-membered, monocyclic carbocyclyl. In certain embodiments, at least one instance of $R^{F1}$ is substituted or unsubstituted heterocyclyl. In certain embodiments, at least one instance of $R^{F1}$ is saturated heterocyclyl. In certain embodiments, at least one instance of $R^{F1}$ is unsaturated heterocyclyl. In certain embodiments, at least one instance of $R^{F1}$ is heterocyclyl, wherein one, two, or three atoms of the heterocyclic ring system are independently selected from the group consisting of nitrogen, oxygen, and sulfur. In certain embodiments, at least one instance of $R^{F1}$ is 3- to 7-membered, monocyclic heterocyclyl. In certain embodiments, at least one instance of $R^{F1}$ is substituted or unsubstituted aryl. In certain embodiments, at least one instance of $R^{F1}$ is 6- to 10-membered aryl. In certain embodiments, at least one instance of $R^{F1}$ is monocyclic aryl. In certain embodiments, at least one instance of $R^{F1}$ is substituted phenyl. In certain embodiments, at least one instance of $R^{F1}$ is unsubstituted phenyl. In certain embodiments, at least one instance of $R^{F1}$ is bicyclic aryl. In certain embodiments, at least one instance of $R^{F1}$ is substituted or unsubstituted heteroaryl. In certain embodiments, at least one instance of $R^{F1}$ is heteroaryl, wherein one, two, three, or four atoms of the heteroaryl ring system are independently selected from the group consisting of nitrogen, oxygen, and sulfur. In certain embodiments, at least one instance of $R^{F1}$ is monocyclic heteroaryl. In certain embodiments, at least one instance of $R^{F1}$ is 5- or 6-membered, monocyclic heteroaryl. In certain embodiments, at least one instance of $R^{F1}$ is bicyclic heteroaryl, wherein the point of attachment may be on any atom of the bicyclic heteroaryl ring system, as valency permits. In certain embodiments, at least one instance of $R^{F1}$ is a nitrogen protecting group when attached to a nitrogen atom. In certain embodiments, at least one instance of $R^{F1}$ is Bn, Boc, Cbz, Fmoc, trifluoroacetyl, triphenylmethyl, acetyl, or Ts when attached to a nitrogen atom. In certain embodiments, $R^{F1}$ is an oxygen protecting group when attached to an oxygen atom. In certain embodiments, $R^{F1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{F1}$ is a sulfur protecting group when attached to a sulfur atom. In certain embodiments, $R^{F1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{F1}$ are joined to form a substituted or unsubstituted heterocyclic ring. In certain embodiments, two instances of $R^{F1}$ are joined to form a saturated or unsaturated heterocyclic ring. In certain embodiments, two instances of $R^{F1}$ are joined to form a heterocyclic ring, wherein one, two, or three atoms of the heterocyclic ring system are independently selected from the group consisting of nitrogen, oxygen, and sulfur. In certain embodiments, two instances of $R^{F1}$ are joined to form a 3- to 7-membered, monocyclic heterocyclic ring. In certain embodiments, two instances of $R^{F1}$ are joined to form a substituted or unsubstituted heteroaryl ring. In certain embodiments, two instances of $R^{F1}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

In certain embodiments, n is 0. In certain embodiments, n is 1. In certain embodiments, n is 2. In certain embodiments, n is 3. In certain embodiments, n is 4. In certain embodiments, n is 5.

In certain embodiments, n is 1; and $R^F$ is —C(=O)N($R^{F1}$)$_2$. In certain embodiments, n is 1; and $R^F$ is —C(=O)N($R^{F1}$)$_2$, wherein each instance of $R^{F1}$ is independently hydrogen, substituted or unsubstituted $C_{1-6}$ alkyl, substituted or unsubstituted phenyl, or a nitrogen protecting group. In certain embodiments, n is 2; and each instance of $R^F$ is independently halogen or substituted or unsubstituted $C_{1-6}$ alkyl. In certain embodiments, n is 2; and each instance of $R^F$ is independently halogen or unsubstituted $C_{1-6}$ alkyl (e.g., —$CH_3$). In certain embodiments, n is 2; and each instance of $R^F$ is independently halogen, substituted or unsubstituted $C_{1-6}$ alkyl, —$OR^{F1}$, or —C(=O)N($R^{F1}$)$_2$. In certain embodiments, n is 2; and each instance of $R^F$ is independently halogen, substituted or unsubstituted $C_{1-6}$ alkyl, —$OR^{F1}$, or —C(=O)N($R^{F1}$)$_2$, wherein each instance of $R^{F1}$ is independently hydrogen, substituted or unsubstituted $C_{1-6}$ alkyl, substituted or unsubstituted phenyl, an oxygen protecting group when attached to an oxygen atom, or a nitrogen protecting group when attached to a nitrogen atom.

In certain embodiments, the compound of Formula (I) is of Formula (I-A):

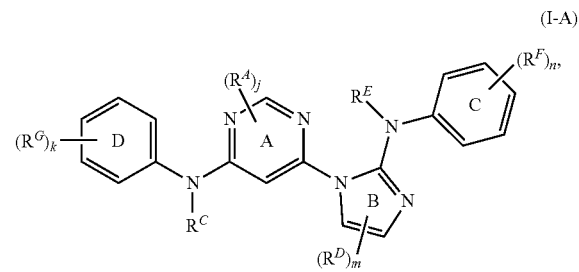

(I-A)

or a pharmaceutically acceptable salt, solvate, hydrate, polymorph, co-crystal, tautomer, stereoisomer, isotopically labeled derivative, or prodrug thereof, wherein:

each instance of $R^G$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{G1}$, —$N(R^{G1})_2$, —$SR^{G1}$, —CN, —SCN, —$C(=NR^{G1})R^{G1}$, —$C(=NR^{G1})OR^{G1}$, —$C(=NR^{G1})N(R^{G1})_2$, —$C(=O)R^{G1}$, —$C(=O)OR^{G1}$, —$C(=O)N(R^{G1})_2$, —$NO_2$, —$NR^{G1}C(=O)R^{G1}$, —$NR^{G1}C(=O)OR^{G1}$, —$NR^{G1}C(=O)N(R^{G1})_2$, —$OC(=O)R^{G1}$, —$OC(=O)OR^{G1}$, or —$OC(=O)N(R^{G1})_2$, wherein each instance of $R^{G1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{G1}$ are joined to form a substituted or unsubstituted heterocyclic or substituted or unsubstituted heteroaryl ring; and k is 0, 1, 2, 3, 4, or 5.

Formula (I-A) includes as Ring D a phenyl ring that is unsubstituted (e.g., when k is 0) or substituted with one or more substituents $R^G$ (e.g., when k is 1, 2, 3, 4, or 5). In certain embodiments, Ring D is of the formula:

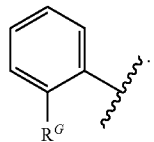

In certain embodiments, Ring D is of the formula:

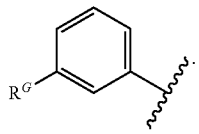

In certain embodiments, Ring D is of the formula:

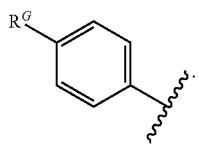

In certain embodiments, Ring D is of the formula:

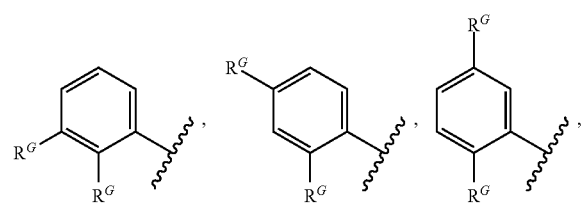

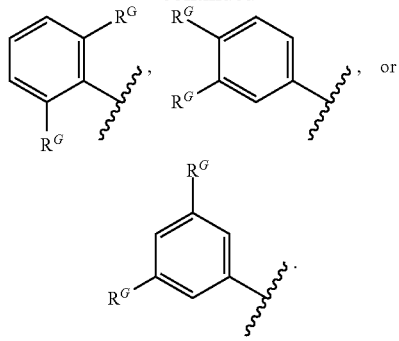

In certain embodiments, at least two instances of $R^G$ are different. In certain embodiments, all instances of $R^G$ are the same. In certain embodiments, at least one instance of $R^G$ is halogen. In certain embodiments, at least one instance of $R^G$ is F. In certain embodiments, at least one instance of $R^G$ is Cl. In certain embodiments, at least one instance of $R^G$ is Br. In certain embodiments, at least one instance of $R^G$ is I (iodine). In certain embodiments, at least one instance of $R^G$ is substituted alkyl. In certain embodiments, at least one instance of $R^G$ is unsubstituted alkyl. In certain embodiments, at least one instance of $R^G$ is unsubstituted $C_{1-6}$ alkyl. In certain embodiments, all instances of $R^G$ are unsubstituted $C_{1-6}$ alkyl. In certain embodiments, at least one instance of $R^G$ is substituted $C_{1-6}$ alkyl. In certain embodiments, at least one instance of $R^G$ is $C_{1-6}$ alkyl substituted with at least one halogen. In certain embodiments, at least one instance of $R^G$ is —$CH_3$. In certain embodiments, all instances of $R^G$ are —$CH_3$. In certain embodiments, at least one instance of $R^G$ is substituted methyl. In certain embodiments, at least one instance of $R^G$ is —$CH_2F$. In certain embodiments, at least one instance of $R^G$ is —$CHF_2$. In certain embodiments, at least one instance of $R^G$ is —$CF_3$. In certain embodiments, at least one instance of $R^G$ is ethyl. In certain embodiments, at least one instance of $R^G$ is propyl. In certain embodiments, at least one instance of $R^G$ is butyl. In certain embodiments, at least one instance of $R^G$ is pentyl. In certain embodiments, at least one instance of $R^G$ is hexyl. In certain embodiments, at least one instance of $R^G$ is substituted alkenyl. In certain embodiments, at least one instance of $R^G$ is unsubstituted alkenyl. In certain embodiments, at least one instance of $R^G$ is substituted alkynyl. In certain embodiments, at least one instance of $R^G$ is unsubstituted alkynyl. In certain embodiments, at least one instance of $R^G$ is substituted carbocyclyl. In certain embodiments, at least one instance of $R^G$ is unsubstituted carbocyclyl. In certain embodiments, at least one instance of $R^G$ is saturated carbocyclyl. In certain embodiments, at least one instance of $R^G$ is unsaturated carbocyclyl. In certain embodiments, at least one instance of $R^G$ is monocyclic carbocyclyl. In certain embodiments, at least one instance of $R^G$ is 3- to 7-membered, monocyclic carbocyclyl. In certain embodiments, at least one instance of $R^G$ is substituted heterocyclyl. In certain embodiments, at least one instance of $R^G$ is unsubstituted heterocyclyl. In certain embodiments, at least one instance of $R^G$ is saturated heterocyclyl. In certain embodiments, at least one instance of $R^G$ is unsaturated heterocyclyl. In certain embodiments, at least one instance of $R^G$ is heterocyclyl, wherein one, two, or three atoms of the heterocyclic ring system are independently selected from the group consisting of nitrogen, oxygen, and sulfur. In certain embodiments, at least one instance of $R^G$ is monocyclic heterocyclyl. In certain embodiments, at least one instance of $R^G$ is 3- to 7-membered, monocyclic heterocyclyl. In certain embodiments, at least one instance of $R^G$ is substituted or unsubstituted piperazinyl. In certain embodiments, at least one instance of $R^G$ is of the formula:

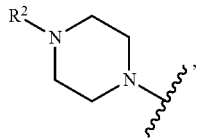

wherein $R^2$ is H, substituted or unsubstituted $C_{1-6}$ alkyl, or a nitrogen protecting group. In certain embodiments, at least one instance of $R^G$ is of the formula:

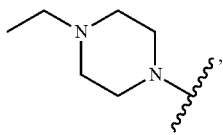 [SMILES: *N1CCN(CC)CC1]

In certain embodiments, at least one instance of $R^G$ is substituted aryl. In certain embodiments, at least one instance of $R^G$ is unsubstituted aryl. In certain embodiments, at least one instance of $R^G$ is 6- to 10-membered aryl. In certain embodiments, at least one instance of $R^G$ is substituted phenyl. In certain embodiments, at least one instance of $R^G$ is unsubstituted phenyl. In certain embodiments, at least one instance of $R^G$ is substituted heteroaryl. In certain embodiments, at least one instance of $R^G$ is unsubstituted heteroaryl. In certain embodiments, at least one instance of $R^G$ is heteroaryl, wherein one, two, three, or four atoms of the heteroaryl ring system are independently selected from the group consisting of nitrogen, oxygen, and sulfur. In certain embodiments, at least one instance of $R^G$ is monocyclic heteroaryl. In certain embodiments, at least one instance of $R^G$ is 5-membered, monocyclic heteroaryl. In certain embodiments, at least one instance of $R^G$ is 6-membered, monocyclic heteroaryl. In certain embodiments, at least one instance of $R^G$ is bicyclic heteroaryl, wherein the point of attachment may be on any atom of the bicyclic heteroaryl ring system, as valency permits. In certain embodiments, at least one instance of $R^G$ is 9- or 10-membered, bicyclic heteroaryl. In certain embodiments, at least one instance of $R^G$ is —$OR^{G1}$. In certain embodiments, at least one instance of $R^G$ is —OH. In certain embodiments, at least one instance of $R^G$ is —O(substituted or unsubstituted $C_{1-6}$ alkyl). In certain embodiments, at least one instance of $R^G$ is —O—$(CH_2)_{2-4}$—O-(substituted or unsubstituted $C_{1-6}$ alkyl). In certain embodiments, at least one instance of $R^G$ is —O—$(CH_2)_2$—OMe. In certain embodiments, at least one instance of $R^G$ is —OMe. In certain embodiments, at least one instance of $R^G$ is —OEt. In certain embodiments, at least one instance of $R^G$ is —OPr. In certain embodiments, at least one instance of $R^G$ is —OBu. In certain embodiments, at least one instance of $R^G$ is —OBn. In certain embodiments, at least one instance of $R^G$ is —OPh. In certain embodiments, at least one instance of $R^G$ is —$SR^{G1}$. In certain embodiments, at least one instance of $R^G$ is —SH. In certain embodiments, at least one instance of $R^G$ is —SMe. In certain embodiments, at least one instance of $R^G$ is —$N(R^{G1})_2$. In certain embodiments, at least one instance of $R^G$ is —$N(R^{G1})_2$, wherein each instance of $R^{G1}$ is independently hydrogen, substituted or unsubstituted $C_{1-6}$ alkyl, or a nitrogen protecting group, or two instances of $R^{G1}$ are joined to form a substituted or unsubstituted, 3- to 7-membered, monocyclic heterocyclic ring. In certain embodiments, at least one instance of $R^G$ is —$NH_2$. In certain embodiments, at least one instance of $R^G$ is —NHMe. In certain embodiments, at least one instance of $R^G$ is —$NMe_2$. In certain embodiments, at least one instance of $R^G$ is —CN. In certain embodiments, at least one instance of $R^G$ is —SCN. In certain embodiments, at least one instance of $R^G$ is —$C(=NR^{G1})R^{G1}$, —$C(=NR^{G1})OR^{G1}$, or —$C(=NR^{G1})N(R^{G1})_2$. In certain embodiments, at least one instance of $R^G$ is —$C(=O)R^{G1}$ or —$C(=O)OR^{G1}$. In certain embodiments, at least one instance of $R^G$ is —$C(=O)N(R^{G1})_2$. In certain embodiments, at least one instance of $R^G$ is —$C(=O)NMe_2$, —$C(=O)NHMe$, or —$C(=O)NH_2$. In certain embodiments, at least one instance of $R^G$ is —$NO_2$. In certain embodiments, at least one instance of $R^G$ is —$NR^{G1}C(=O)R^{G1}$, —$NR^{G1}C(=O)OR^{G1}$, or —$NR^{G1}C(=O)N(R^{G1})_2$. In certain embodiments, at least one instance of $R^G$ is —$OC(=O)R^{G1}$, —$OC(=O)OR^{G1}$, or —$OC(=O)N(R^{G1})_2$.

In certain embodiments, at least one instance of $R^G$ is —$OR^{G1}$, —$N(R^{G1})_2$, or substituted or unsubstituted, 3- to 7-membered, monocyclic heterocyclyl, wherein one, two, or three atoms of the heterocyclic ring system are independently nitrogen, oxygen, or sulfur.

In certain embodiments, at least one instance of $R^{G1}$ is H. In certain embodiments, at least one instance of $R^{G1}$ is substituted acyl. In certain embodiments, at least one instance of $R^{G1}$ is unsubstituted acyl. In certain embodiments, at least one instance of $R^{G1}$ is acetyl. In certain embodiments, at least one instance of $R^{G1}$ is substituted alkyl. In certain embodiments, at least one instance of $R^{G1}$ is unsubstituted alkyl. In certain embodiments, at least one instance of $R^{G1}$ is unsubstituted $C_{1-6}$ alkyl. In certain embodiments, at least one instance of $R^{G1}$ is methyl. In certain embodiments, at least one instance of $R^{G1}$ is ethyl. In certain embodiments, at least one instance of $R^{G1}$ is propyl. In certain embodiments, at least one instance of $R^{G1}$ is butyl. In certain embodiments, at least one instance of $R^{G1}$ is pentyl. In certain embodiments, at least one instance of $R^{G1}$ is hexyl. In certain embodiments, at least one instance of $R^{G1}$ is substituted alkenyl. In certain embodiments, at least one instance of $R^{G1}$ is unsubstituted alkenyl. In certain embodiments, at least one instance of $R^{G1}$ is substituted alkynyl. In certain embodiments, at least one instance of $R^{G1}$ is unsubstituted alkynyl. In certain embodiments, at least one instance of $R^{G1}$ is substituted or unsubstituted carbocyclyl. In certain embodiments, at least one instance of $R^{G1}$ is saturated carbocyclyl. In certain embodiments, at least one instance of $R^{G1}$ is unsaturated carbocyclyl. In certain embodiments, at least one instance of $R^{G1}$ is 3- to 7-membered, monocyclic carbocyclyl. In certain embodiments, at least one instance of $R^{G1}$ is substituted or unsubstituted heterocyclyl. In certain embodiments, at least one instance of $R^{G1}$ is saturated heterocyclyl. In certain embodiments, at least one instance of $R^{G1}$ is unsaturated heterocyclyl. In certain embodiments, at least one instance of $R^{G1}$ is heterocyclyl, wherein one, two, or three atoms of the heterocyclic ring system are independently selected from the group consisting of nitrogen, oxygen, and sulfur. In certain embodiments, at least one instance of $R^{G1}$ is 3- to 7-membered, monocyclic heterocyclyl. In certain embodiments, at least one instance of $R^{G1}$ is substituted or unsubstituted aryl. In certain embodiments, at least one instance of $R^{G1}$ is 6- to 10-membered aryl. In certain embodiments, at least one instance of $R^{G1}$ is monocyclic aryl. In certain embodiments, at least one instance of $R^{G1}$ is substituted phenyl. In certain embodiments, at least one instance of $R^{G1}$ is unsubstituted phenyl. In certain embodiments, at least one instance of $R^{G1}$ is bicyclic aryl. In certain embodiments, at least one instance of $R^{G1}$ is substituted or unsubstituted heteroaryl. In certain embodiments, at least one instance of $R^{G1}$ is heteroaryl, wherein one, two, three, or four atoms of the heteroaryl ring system are independently selected from the group consisting of nitrogen, oxygen, and sulfur. In certain embodiments, at least one instance of $R^{G1}$ is monocyclic heteroaryl. In certain embodiments, at least one instance of $R^{G1}$ is 5- or 6-membered, monocyclic heteroaryl. In certain embodiments, at least one instance of $R^{G1}$ is bicyclic heteroaryl, wherein the point of attachment may be on any atom of the bicyclic heteroaryl ring system, as valency permits. In certain embodiments, at least one instance of $R^{G1}$ is a nitrogen protecting group when attached to a nitrogen atom. In certain embodiments, at least one instance of $R^{G1}$ is Bn, Boc, Cbz, Fmoc, trifluoroacetyl, triphenylmethyl, acetyl, or Ts when attached to a nitrogen atom. In certain embodiments, $R^{G1}$ is an oxygen protecting group when attached to an oxygen atom. In certain embodiments, $R^{G1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{G1}$ is a sulfur protecting group when attached to a sulfur atom. In certain embodiments, $R^{G1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{G1}$ are joined to form a substituted or unsubstituted heterocyclic ring. In certain embodiments, two instances of $R^{G1}$ are joined to form a saturated or unsaturated heterocyclic ring. In certain embodiments, two instances of $R^{G1}$ are joined to form a heterocyclic ring, wherein one, two, or three atoms of the heterocyclic ring system are independently selected from the group consisting of nitrogen, oxygen, and sulfur. In certain embodiments, two instances of $R^{G1}$ are joined to form a 3- to 7-membered, monocyclic heterocyclic ring. In certain embodiments, two instances of $R^{G1}$ are joined to form a substituted or unsubstituted heteroaryl ring. In certain embodiments, two instances of $R^{G1}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

In certain embodiments, k is 0. In certain embodiments, k is 1. In certain embodiments, k is 2. In certain embodiments, k is 3. In certain embodiments, k is 4. In certain embodiments, k is 5.

In certain embodiments, k is 1; and $R^G$ is —$OR^{G1}$, —$N(R^{G1})_2$, or substituted or unsubstituted, 3- to 7-membered, monocyclic heterocyclyl, wherein one, two, or three atoms of the heterocyclic ring system are independently nitrogen, oxygen, or sulfur. In certain embodiments, k is 1; and $R^G$ is —$OR^{G1}$, —$N(R^{G1})_2$, or substituted or unsubstituted, 3- to 7-membered, monocyclic heterocyclyl, wherein one, two, or three atoms of the heterocyclic ring system are independently nitrogen, oxygen, or sulfur; and each instance of $R^{G1}$ is independently H, substituted or unsubstituted $C_{1-6}$ alkyl, an oxygen protecting group when attached to an oxygen atom, or a nitrogen protecting group when attached to a nitrogen group.

In certain embodiments, the compound of Formula (I) is of the formula:

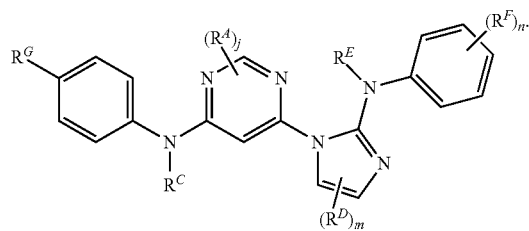

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

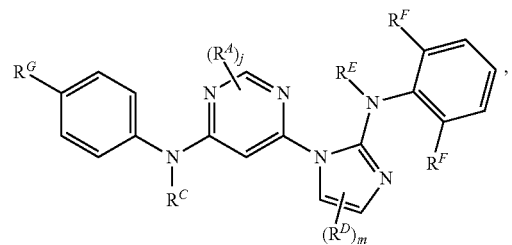

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

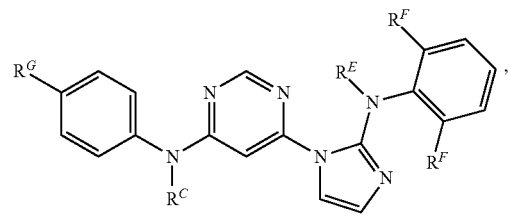

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

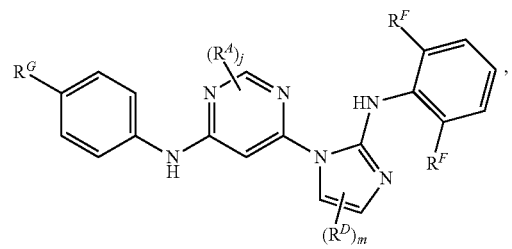

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

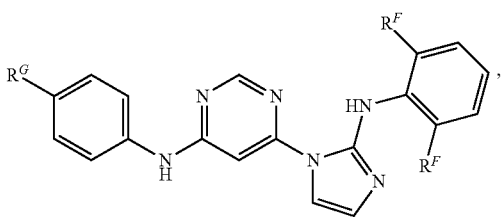

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (I-B):

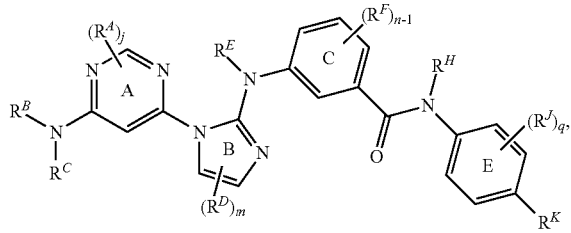

(I-B)

or a pharmaceutically acceptable salt, solvate, hydrate, polymorph, co-crystal, tautomer, stereoisomer, isotopically labeled derivative, or prodrug thereof, wherein:

$R^H$ is hydrogen, substituted or unsubstituted acyl, substituted or unsubstituted $C_{1-6}$ alkyl, or a nitrogen protecting group;

each instance of $R^J$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{J1}$, —$N(R^{J1})_2$, —$SR^{J1}$, —CN, —SCN, —C(=$NR^{J1}$)$R^{J1}$, —C(=$NR^{J1}$)$OR^{J1}$, —C(=$NR^{J1}$)$N(R^{J1})_2$, —C(=O)$R^{J1}$, —C(=O)$OR^{J1}$, —C(=O)$N(R^{J1})_2$, —NO$_2$, —$NR^{J1}$C(=O)$R^{J1}$, —$NR^{J1}$C(=O)$OR^{J1}$, —$NR^{J1}$C(=O)$N(R^{J1})_2$, —OC(=O)$R^J$, —OC(=O)$OR^J$, or —OC(=O)$N(R^{J1})_2$, wherein each instance of $R^{J1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{J1}$ are joined to form a substituted or unsubstituted heterocyclic or substituted or unsubstituted heteroaryl ring;

q is 0, 1, 2, 3, or 4; and $R^K$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{K1}$, —$N(R^{K1})_2$, —$SR^{K1}$, —CN, —SCN, —C(=$NR^{K1}$)$R^{K1}$, —C(=$NR^{K1}$)$OR^{K1}$, —C(=$NR^{K1}$)$N(R^{K1})_2$, —C(=O)$R^{K1}$, —C(=O)$OR^{K1}$, —C(=O)$N(R^{K1})_2$, —NO$_2$, —$NR^{K1}$C(=O)$R^{K1}$, —$NR^{K1}$C(=O)$OR^{K1}$, —$NR^{K1}$C(=O)$N(R^{K1})_2$, —OC(=O)$R^{K1}$, —OC(=O)$OR^{K1}$, or —OC(=O)$N(R^{K1})_2$, wherein each instance of $R^{K1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{K1}$ are joined to form a substituted or unsubstituted heterocyclic or substituted or unsubstituted heteroaryl ring.

In certain embodiments, a compound of Formula (I) is of Formula (I-B), wherein when $R^C$ is hydrogen, $R^B$ is not unsubstituted cyclopropyl or

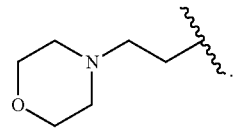 [SMILES: *CCN1CCOCC1]

Formula (I-B) includes substituent $R^H$ on a nitrogen atom. In certain embodiments, $R^H$ is H. In certain embodiments, $R^H$ is not H. In certain embodiments, $R^H$ is substituted acyl. In certain embodiments, $R^H$ is unsubstituted acyl. In certain embodiments, $R^H$ is acetyl. In certain embodiments, $R^H$ is unsubstituted $C_{1-6}$ alkyl. In certain embodiments, $R^H$ is substituted $C_{1-6}$ alkyl. In certain embodiments, $R^H$ is $C_{1-6}$ alkyl substituted with at least one halogen. In certain embodiments, $R^H$ is unsubstituted methyl. In certain embodiments, $R^H$ is substituted methyl. In certain embodiments, $R^H$ is —$CH_2F$. In certain embodiments, $R^H$ is —$CHF_2$. In certain embodiments, $R^H$ is —$CF_3$. In certain embodiments, $R^H$ is ethyl. In certain embodiments, $R^H$ is propyl. In certain embodiments, $R^H$ is butyl. In certain embodiments, $R^H$ is pentyl. In certain embodiments, $R^H$ is hexyl. In certain embodiments, $R^H$ is a nitrogen protecting group. In certain embodiments, $R^H$ is Bn, Boc, Cbz, Fmoc, trifluoroacetyl, triphenylmethyl, acetyl, or Ts. In certain embodiments, $R^H$ is hydrogen or unsubstituted $C_{1-6}$ alkyl.

Formula (I-B) includes as Ring E a phenyl ring that is substituted with $R^K$ and optionally one or more substituents $R^J$. In certain embodiments, Ring E is of the formula:

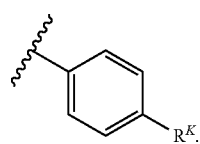

In certain embodiments, Ring E is of the formula:

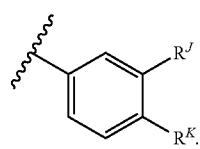

In certain embodiments, Ring E is of the formula:

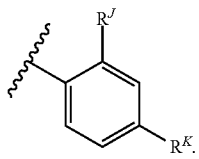

In certain embodiments, Ring E is of the formula:

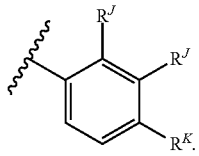

In certain embodiments, Ring E is of the formula:

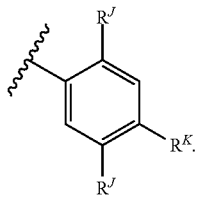

In certain embodiments, Ring E is of formula:

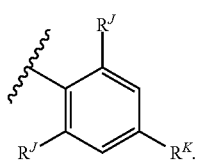

In certain embodiments, Ring E is of the formula:

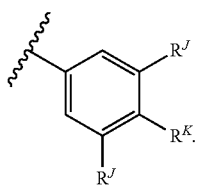

In certain embodiments, $R^K$ is H. In certain embodiments, $R^K$ is halogen. In certain embodiments, $R^K$ is F. In certain embodiments, $R^K$ is Cl. In certain embodiments, $R^K$ is Br. In certain embodiments, $R^K$ is I (iodine). In certain embodiments, $R^K$ is substituted alkyl. In certain embodiments, $R^K$ is unsubstituted alkyl. In certain embodiments, $R^K$ is unsubstituted $C_{1-6}$ alkyl. In certain embodiments, $R^K$ is substituted $C_{1-6}$ alkyl. In certain embodiments, $R^K$ is $C_{1-6}$ alkyl substituted with at least one halogen. In certain embodiments, $R^K$ is —$CH_3$. In certain embodiments, $R^K$ is substituted methyl. In certain embodiments, $R^K$ is —$CH_2F$. In certain embodiments, $R^K$ is —$CHF_2$. In certain embodiments, $R^K$ is —$CF_3$. In certain embodiments, $R^K$ is ethyl. In certain embodiments, $R^K$ is propyl. In certain embodiments, $R^K$ is butyl. In certain embodiments, $R^K$ is pentyl. In certain embodiments, $R^K$ is hexyl. In certain embodiments, $R^K$ is substituted alkenyl. In certain embodiments, $R^K$ is unsubstituted alkenyl. In certain embodiments, $R^K$ is substituted alkynyl. In certain embodiments, $R^K$ is unsubstituted alkynyl. In certain embodiments, $R^K$ is substituted carbocyclyl. In certain embodiments, $R^K$ is unsubstituted carbocyclyl. In certain embodiments, $R^K$ is saturated carbocyclyl. In certain embodiments, $R^K$ is unsaturated carbocyclyl. In certain embodiments, $R^K$ is monocyclic carbocyclyl. In certain embodiments, $R^K$ is 3- to 7-membered, monocyclic carbocyclyl. In certain embodiments, $R^K$ is substituted heterocyclyl. In certain embodiments, $R^K$ is unsubstituted heterocyclyl. In certain embodiments, $R^K$ is saturated heterocyclyl. In certain embodiments, $R^K$ is unsaturated heterocyclyl. In certain embodiments, $R^K$ is heterocyclyl, wherein one, two, or three atoms of the heterocyclic ring system are independently selected from the group consisting of nitrogen, oxygen, and sulfur. In certain embodiments, $R^K$ is monocyclic heterocyclyl. In certain embodiments, $R^K$ is 3- to 7-membered, monocyclic heterocyclyl. In certain embodiments, $R^K$ is substituted aryl. In certain embodiments, $R^K$ is unsubstituted aryl. In certain embodiments, $R^K$ is 6- to 10-membered aryl. In certain embodiments, $R^K$ is substituted phenyl. In certain embodiments, $R^K$ is unsubstituted phenyl. In certain embodiments, $R^K$ is substituted heteroaryl. In certain embodiments, $R^K$ is unsubstituted heteroaryl. In certain embodiments, $R^K$ is heteroaryl, wherein one, two, three, or four atoms of the heteroaryl ring system are independently selected from the group consisting of nitrogen, oxygen, and sulfur. In certain embodiments, $R^K$ is monocyclic heteroaryl. In certain embodiments, $R^K$ is 5-membered, monocyclic heteroaryl. In certain embodiments, $R^K$ is not substituted imidazolyl. In certain embodiments, $R^K$ is 6-membered, monocyclic heteroaryl. In certain embodiments, $R^K$ is bicyclic heteroaryl, wherein the point of attachment may be on any atom of the bicyclic heteroaryl ring system, as valency permits. In certain embodiments, $R^K$ is 9- or 10-membered, bicyclic heteroaryl. In certain embodiments, $R^K$ is —$OR^{K1}$. In certain embodiments, $R^K$ is —OH. In certain embodiments, $R^K$ is —O(substituted or unsubstituted $C_{1-6}$ alkyl). In certain embodiments, $R^K$ is —OMe. In certain embodiments, $R^K$ is —OEt. In certain embodiments, $R^K$ is —OPr. In certain embodiments, $R^K$ is —OBu. In certain embodiments, $R^K$ is —OBn. In certain embodiments, $R^K$ is —OPh. In certain embodiments, $R^K$ is —$SR^{K1}$. In certain embodiments, $R^K$ is —SH. In certain embodiments, $R^K$ is —SMe. In certain embodiments, $R^K$ is —$N(R^{K1})_2$. In certain embodiments, $R^K$ is —$NH_2$. In certain embodiments, $R^K$ is —NHMe. In certain embodiments, $R^K$ is —$NMe_2$. In certain embodiments, $R^K$ is —CN. In certain embodiments, $R^K$ is —SCN. In certain embodiments, $R^K$ is —$C(=NR^{K1})R^{K1}$, —$C(=NR^{K1})OR^{K1}$, or —$C(=NR^{K1})N(R^{K1})_2$. In certain embodiments, $R^K$ is —$C(=O)R^{K1}$ or —$C(=O)OR^{K1}$. In certain embodiments, $R^K$ is —$C(=O)N(R^{K1})_2$. In certain embodiments, $R^K$ is —$C(=O)NMe_2$, —$C(=O)NHMe$, or —$C(=O)NH_2$. In certain embodiments, $R^K$ is —$NO_2$. In certain embodiments, $R^K$ is —$NR^{K1}C(=O)R^{K1}$, —$NR^{K1}C(=O)OR^{K1}$, or —$NR^{K1}C(=O)N(R^{K1})_2$. In certain embodiments, $R^K$ is —$OC(=O)R^{K1}$, —$OC(=O)OR^{K1}$, or —$OC(=O)N(R^{K1})_2$.

In certain embodiments, $R^K$ is —$(CH_2)_{1-3}$-(Ring G), wherein Ring G is a substituted or unsubstituted, 3- to 7-membered, monocyclic heterocyclic ring. In certain embodiments, $R^K$ is —(CH$_2$)$_{1-3}$-(substituted or unsubstituted piperazinyl). In certain embodiments, $R^K$ is of the formula:

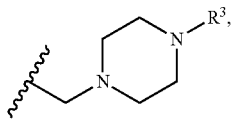

wherein $R^3$ is H, substituted or unsubstituted C$_{2-6}$ alkyl, substituted methyl, or a nitrogen protecting group. In certain embodiments, $R^K$ is of the formula:

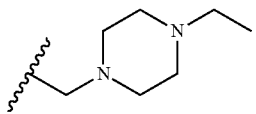

In certain embodiments, $R^K$ is not of the formula:

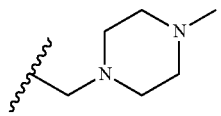

In certain embodiments, $R^K$ is —(CH$_2$)$_{1-3}$-(Ring G), wherein Ring G is a substituted or unsubstituted oxetanyl, substituted or unsubstituted azetidinyl, substituted or unsubstituted tetrahydrofuranyl, substituted or unsubstituted pyrrolidinyl, substituted or unsubstituted tetrahydropyranyl, substituted or unsubstituted piperidinyl, or substituted or unsubstituted morpholinyl ring.

In certain embodiments, $R^{K1}$ is H. In certain embodiments, $R^{K1}$ is substituted acyl. In certain embodiments, $R^{K1}$ is unsubstituted acyl. In certain embodiments, $R^{K1}$ is acetyl. In certain embodiments, $R^{K1}$ is substituted alkyl. In certain embodiments, $R^{K1}$ is unsubstituted alkyl. In certain embodiments, $R^{K1}$ is unsubstituted C$_{1-6}$ alkyl. In certain embodiments, $R^{K1}$ is methyl. In certain embodiments, $R^{K1}$ is ethyl. In certain embodiments, $R^{K1}$ is propyl. In certain embodiments, $R^{K1}$ is butyl. In certain embodiments, $R^{K1}$ is pentyl. In certain embodiments, $R^{K1}$ is hexyl. In certain embodiments, $R^{K1}$ is substituted alkenyl. In certain embodiments, $R^{K1}$ is unsubstituted alkenyl. In certain embodiments, $R^{K1}$ is substituted alkynyl. In certain embodiments, $R^{K1}$ is unsubstituted alkynyl. In certain embodiments, $R^{K1}$ is substituted or unsubstituted carbocyclyl. In certain embodiments, $R^{K1}$ is saturated carbocyclyl. In certain embodiments, $R^{K1}$ is unsaturated carbocyclyl. In certain embodiments, $R^{K1}$ is 3- to 7-membered, monocyclic carbocyclyl. In certain embodiments, $R^{K1}$ is substituted or unsubstituted heterocyclyl. In certain embodiments, $R^{K1}$ is saturated heterocyclyl. In certain embodiments, $R^{K1}$ is unsaturated heterocyclyl. In certain embodiments, $R^{K1}$ is heterocyclyl, wherein one, two, or three atoms of the heterocyclic ring system are independently selected from the group consisting of nitrogen, oxygen, and sulfur. In certain embodiments, $R^{K1}$ is 3- to 7-membered, monocyclic heterocyclyl. In certain embodiments, $R^{K1}$ is substituted or unsubstituted aryl. In certain embodiments, $R^{K1}$ is 6- to 10-membered aryl. In certain embodiments, $R^{K1}$ is monocyclic aryl. In certain embodiments, $R^{K1}$ is substituted phenyl. In certain embodiments, $R^{K1}$ is unsubstituted phenyl. In certain embodiments, $R^{K1}$ is bicyclic aryl. In certain embodiments, $R^{K1}$ is substituted or unsubstituted heteroaryl. In certain embodiments, $R^{K1}$ is heteroaryl, wherein one, two, three, or four atoms of the heteroaryl ring system are independently selected from the group consisting of nitrogen, oxygen, and sulfur. In certain embodiments, $R^{K1}$ is monocyclic heteroaryl. In certain embodiments, $R^{K1}$ is 5- or 6-membered, monocyclic heteroaryl. In certain embodiments, $R^{K1}$ is bicyclic heteroaryl, wherein the point of attachment may be on any atom of the bicyclic heteroaryl ring system, as valency permits. In certain embodiments, $R^{K1}$ is a nitrogen protecting group when attached to a nitrogen atom. In certain embodiments, $R^{K1}$ is Bn, Boc, Cbz, Fmoc, trifluoroacetyl, triphenylmethyl, acetyl, or Ts when attached to a nitrogen atom. In certain embodiments, $R^{K1}$ is an oxygen protecting group when attached to an oxygen atom. In certain embodiments, $R^{K1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{K1}$ is a sulfur protecting group when attached to a sulfur atom. In certain embodiments, $R^{K1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{K1}$ are joined to form a substituted or unsubstituted heterocyclic ring. In certain embodiments, two instances of $R^{K1}$ are joined to form a saturated or unsaturated heterocyclic ring. In certain embodiments, two instances of $R^{K1}$ are joined to form a heterocyclic ring, wherein one, two, or three atoms of the heterocyclic ring system are independently selected from the group consisting of nitrogen, oxygen, and sulfur. In certain embodiments, two instances of $R^{K1}$ are joined to form a 3- to 7-membered, monocyclic heterocyclic ring. In certain embodiments, two instances of $R^{K1}$ are joined to form a substituted or unsubstituted heteroaryl ring. In certain embodiments, two instances of $R^{K1}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

Ring E of Formula (I-B) may include one or more substituents $R^J$. In certain embodiments, at least two instances of $R^J$ are different. In certain embodiments, all instances of $R^J$ are the same. In certain embodiments, at least one instance of $R^J$ is halogen. In certain embodiments, at least one instance of $R^J$ is F. In certain embodiments, at least one instance of $R^J$ is Cl. In certain embodiments, at least one instance of $R^J$ is Br. In certain embodiments, at least one instance of $R^J$ is I (iodine). In certain embodiments, at least one instance of $R^J$ is substituted alkyl. In certain embodiments, at least one instance of $R^J$ is unsubstituted alkyl. In certain embodiments, at least one instance of $R^J$ is unsubstituted C$_{1-6}$ alkyl. In certain embodiments, all instances of $R^J$ are unsubstituted C$_{1-6}$ alkyl. In certain embodiments, at least one instance of $R^J$ is substituted C$_{1-6}$ alkyl. In certain embodiments, at least one instance of $R^J$ is C$_{1-6}$ alkyl substituted with at least one halogen. In certain embodiments, at least one instance of $R^J$ is —CH$_3$. In certain embodiments, all instances of $R^J$ are —CH$_3$. In certain embodiments, at least one instance of $R^J$ is substituted methyl. In certain embodiments, at least one instance of $R^J$ is —CH$_2$F. In certain embodiments, at least one instance of $R^J$ is —CHF$_2$. In certain embodiments, at least one instance of $R^J$ is —CF$_3$. In certain embodiments, at least one instance of $R^J$ is ethyl. In certain embodiments, at least one instance of $R^J$ is propyl. In certain embodiments, at least one instance of $R^J$ is butyl. In certain embodiments, at least one instance of $R^J$ is pentyl. In certain embodiments, at least one instance of $R^J$ is hexyl. In certain embodiments, at least one instance of $R^J$ is halogen or substituted or unsubstituted $C_{1-6}$ alkyl. In certain embodiments, at least one instance of $R^J$ is substituted alkenyl. In certain embodiments, at least one instance of $R^J$ is unsubstituted alkenyl. In certain embodiments, at least one instance of $R^J$ is substituted alkynyl. In certain embodiments, at least one instance of $R^J$ is unsubstituted alkynyl. In certain embodiments, at least one instance of $R^J$ is substituted carbocyclyl. In certain embodiments, at least one instance of $R^J$ is unsubstituted carbocyclyl. In certain embodiments, at least one instance of $R^J$ is saturated carbocyclyl. In certain embodiments, at least one instance of $R^J$ is unsaturated carbocyclyl. In certain embodiments, at least one instance of $R^J$ is monocyclic carbocyclyl. In certain embodiments, at least one instance of $R^J$ is 3- to 7-membered, monocyclic carbocyclyl. In certain embodiments, at least one instance of $R^J$ is substituted heterocyclyl. In certain embodiments, at least one instance of $R^J$ is unsubstituted heterocyclyl. In certain embodiments, at least one instance of $R^J$ is saturated heterocyclyl. In certain embodiments, at least one instance of $R^J$ is unsaturated heterocyclyl. In certain embodiments, at least one instance of $R^J$ is heterocyclyl, wherein one, two, or three atoms of the heterocyclic ring system are independently selected from the group consisting of nitrogen, oxygen, and sulfur. In certain embodiments, at least one instance of $R^J$ is monocyclic heterocyclyl. In certain embodiments, at least one instance of $R^J$ is 3- to 7-membered, monocyclic heterocyclyl. In certain embodiments, at least one instance of $R^J$ is substituted aryl. In certain embodiments, at least one instance of $R^J$ is unsubstituted aryl. In certain embodiments, at least one instance of $R^J$ is 6- to 10-membered aryl. In certain embodiments, at least one instance of $R^J$ is substituted phenyl. In certain embodiments, at least one instance of $R^J$ is unsubstituted phenyl. In certain embodiments, at least one instance of $R^J$ is substituted heteroaryl. In certain embodiments, at least one instance of $R^J$ is unsubstituted heteroaryl. In certain embodiments, at least one instance of $R^J$ is heteroaryl, wherein one, two, three, or four atoms of the heteroaryl ring system are independently selected from the group consisting of nitrogen, oxygen, and sulfur. In certain embodiments, at least one instance of $R^J$ is monocyclic heteroaryl. In certain embodiments, at least one instance of $R^J$ is 5-membered, monocyclic heteroaryl. In certain embodiments, no instance of $R^J$ is substituted imidazolyl. In certain embodiments, at least one instance of $R^J$ is 6-membered, monocyclic heteroaryl. In certain embodiments, at least one instance of $R^J$ is bicyclic heteroaryl, wherein the point of attachment may be on any atom of the bicyclic heteroaryl ring system, as valency permits. In certain embodiments, at least one instance of $R^J$ is 9- or 10-membered, bicyclic heteroaryl. In certain embodiments, at least one instance of $R^J$ is —$OR^J$. In certain embodiments, at least one instance of $R^J$ is —OH. In certain embodiments, at least one instance of $R^J$ is —O(substituted or unsubstituted $C_{1-6}$ alkyl). In certain embodiments, at least one instance of $R^J$ is —OMe. In certain embodiments, at least one instance of $R^J$ is —OEt. In certain embodiments, at least one instance of $R^J$ is —OPr. In certain embodiments, at least one instance of $R^J$ is —OBu. In certain embodiments, at least one instance of $R^J$ is —OBn. In certain embodiments, at least one instance of $R^J$ is —OPh. In certain embodiments, at least one instance of $R^J$ is —$SR^{J1}$. In certain embodiments, at least one instance of $R^J$ is —SH. In certain embodiments, at least one instance of $R^J$ is —SMe. In certain embodiments, at least one instance of $R^J$ is —$N(R^{J1})_2$. In certain embodiments, at least one instance of $R^J$ is —$NH_2$. In certain embodiments, at least one instance of $R^J$ is —NHMe. In certain embodiments, at least one instance of $R^J$ is —$NMe_2$. In certain embodiments, at least one instance of $R^J$ is —CN. In certain embodiments, at least one instance of $R^J$ is —SCN. In certain embodiments, at least one instance of $R^J$ is —$C(=NR^{J1})R^{J1}$, —$C(=NR^{J1})OR^{J1}$, or —$C(=NR^{J1})N(R^{J1})_2$. In certain embodiments, at least one instance of $R^J$ is —$C(=O)R^{J1}$ or —$C(=O)OR^{J1}$. In certain embodiments, at least one instance of $R^J$ is —$C(=O)N(R^{J1})_2$. In certain embodiments, at least one instance of $R^J$ is —$C(=O)NMe_2$, —$C(=O)NHMe$, or —$C(=O)NH_2$. In certain embodiments, at least one instance of $R^J$ is —$NO_2$. In certain embodiments, at least one instance of $R^J$ is —$NR^{J1}C(=O)R^{J1}$, —$NR^{J1}C(=O)OR^{J1}$, or —$NR^{J1}C(=O)N(R^{J1})_2$. In certain embodiments, at least one instance of $R^J$ is —$OC(=O)R^{J1}$, —$OC(=O)OR^{J1}$, or —$OC(=O)N(R^{J1})_2$.

In certain embodiments, at least one instance of $R^J$ is halogen or substituted or unsubstituted $C_{1-6}$ alkyl. In certain embodiments, at least one instance of $R^J$ is halogen, unsubstituted $C_{1-6}$ alkyl, or $C_{1-6}$ alkyl substituted with at least one halogen.

In certain embodiments, at least one instance of $R^{J1}$ is H. In certain embodiments, at least one instance of $R^{J1}$ is substituted acyl. In certain embodiments, at least one instance of $R^{J1}$ is unsubstituted acyl. In certain embodiments, at least one instance of $R^{J1}$ is acetyl. In certain embodiments, at least one instance of $R^{J1}$ is substituted alkyl. In certain embodiments, at least one instance of $R^{J1}$ is unsubstituted alkyl. In certain embodiments, at least one instance of $R^{J1}$ is unsubstituted $C_{1-6}$ alkyl. In certain embodiments, at least one instance of $R^{J1}$ is methyl. In certain embodiments, at least one instance of $R^{J1}$ is ethyl. In certain embodiments, at least one instance of $R^{J1}$ is propyl. In certain embodiments, at least one instance of $R^{J1}$ is butyl. In certain embodiments, at least one instance of $R^{J1}$ is pentyl. In certain embodiments, at least one instance of $R^{J1}$ is hexyl. In certain embodiments, at least one instance of $R^{J1}$ is substituted alkenyl. In certain embodiments, at least one instance of $R^{J1}$ is unsubstituted alkenyl. In certain embodiments, at least one instance of $R^{J1}$ is substituted alkynyl. In certain embodiments, at least one instance of $R^{J1}$ is unsubstituted alkynyl. In certain embodiments, at least one instance of $R^{J1}$ is substituted or unsubstituted carbocyclyl. In certain embodiments, at least one instance of $R^{J1}$ is saturated carbocyclyl. In certain embodiments, at least one instance of $R^{J1}$ is unsaturated carbocyclyl. In certain embodiments, at least one instance of $R^{J1}$ is 3- to 7-membered, monocyclic carbocyclyl. In certain embodiments, at least one instance of $R^{J1}$ is substituted or unsubstituted heterocyclyl. In certain embodiments, at least one instance of $R^{J1}$ is saturated heterocyclyl. In certain embodiments, at least one instance of $R^{J1}$ is unsaturated heterocyclyl. In certain embodiments, at least one instance of $R^{J1}$ is heterocyclyl, wherein one, two, or three atoms of the heterocyclic ring system are independently selected from the group consisting of nitrogen, oxygen, and sulfur. In certain embodiments, at least one instance of $R^{J1}$ is 3- to 7-membered, monocyclic heterocyclyl. In certain embodiments, at least one instance of $R^{J1}$ is substituted or unsubstituted aryl. In certain embodiments, at least one instance of $R^{J1}$ is 6- to 10-membered aryl. In certain embodiments, at least one instance of $R^{J1}$ is monocyclic aryl. In certain embodiments, at least one instance of $R^{J1}$ is substituted phenyl. In certain embodiments, at least one instance of $R^{J1}$ is unsubstituted phenyl. In certain embodiments, at least one instance of $R^{J1}$ is bicyclic aryl. In certain embodiments, at least one instance of $R^{J1}$ is substituted or unsubstituted heteroaryl. In certain embodiments, at least one instance of $R^{J1}$ is heteroaryl, wherein one, two, three, or four atoms of the heteroaryl ring system are independently selected from the group consisting of nitrogen, oxygen, and sulfur. In certain embodiments, at least one instance of $R^{J1}$ is monocyclic heteroaryl. In certain embodiments, at least one instance of $R^{J1}$ is 5- or 6-membered, monocyclic heteroaryl. In certain embodiments, at least one instance of $R^{J1}$ is bicyclic heteroaryl, wherein the point of attachment may be on any atom of the bicyclic heteroaryl ring system, as valency permits. In certain embodiments, at least one instance of $R^{J1}$ is a nitrogen protecting group when attached to a nitrogen atom. In certain embodiments, at least one instance of $R^{J1}$ is Bn, Boc, Cbz, Fmoc, trifluoroacetyl, triphenylmethyl, acetyl, or Ts when attached to a nitrogen atom. In certain embodiments, $R^{J1}$ is an oxygen protecting group when attached to an oxygen atom. In certain embodiments, $R^{J1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{J1}$ is a sulfur protecting group when attached to a sulfur atom. In certain embodiments, $R^{J1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{J1}$ are joined to form a substituted or unsubstituted heterocyclic ring. In certain embodiments, two instances of $R^{J1}$ are joined to form a saturated or unsaturated heterocyclic ring. In certain embodiments, two instances of $R^{J1}$ are joined to form a heterocyclic ring, wherein one, two, or three atoms of the heterocyclic ring system are independently selected from the group consisting of nitrogen, oxygen, and sulfur. In certain embodiments, two instances of $R^{J1}$ are joined to form a 3- to 7-membered, monocyclic heterocyclic ring. In certain embodiments, two instances of $R^{J1}$ are joined to form a substituted or unsubstituted heteroaryl ring. In certain embodiments, two instances of $R^{J1}$ are joined to form a substituted or unsubstituted, 5- to 6-membered, monocyclic heteroaryl ring, wherein one, two, three, or four atoms of the heteroaryl ring system are independently nitrogen, oxygen, or sulfur.

In certain embodiments, q is 0. In certain embodiments, q is 1. In certain embodiments, q is 2. In certain embodiments, q is 3. In certain embodiments, q is 4.

In certain embodiments, no instance of $R^J$ and $R^K$ is substituted or unsubstituted heteroaryl. In certain embodiments, no instance of $R^J$ and $R^K$ is substituted or unsubstituted imidazolyl. In certain embodiments, no instance of $R^J$ and $R^K$ is substituted imidazolyl.

In certain embodiments, the compound of Formula (I) is of the formula:

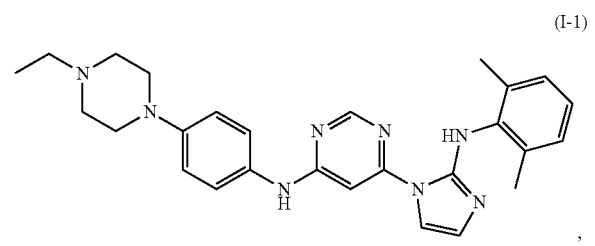

(I-1)

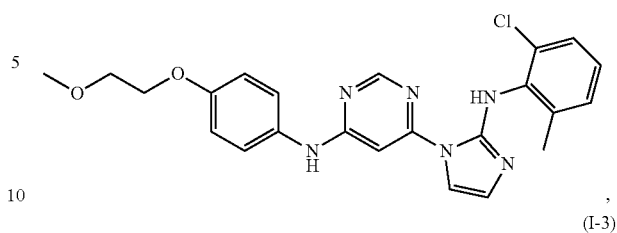

(I-2)

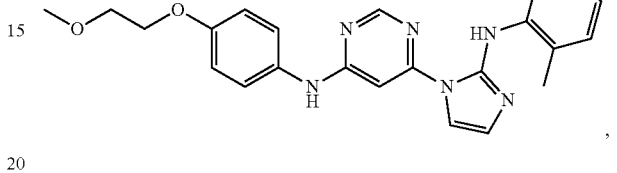

(I-3)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

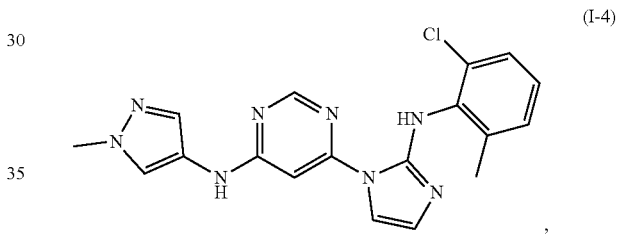

(I-4)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

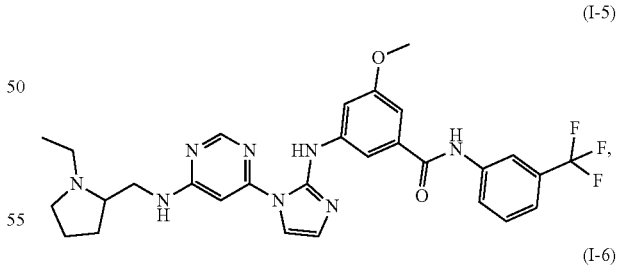

(I-5)

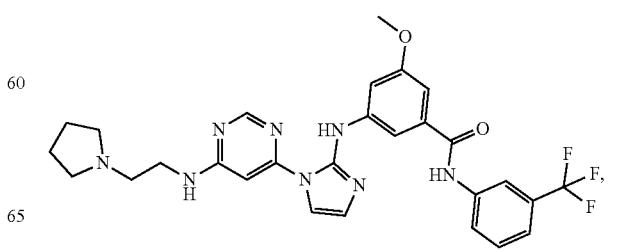

(I-6)

(I-7)
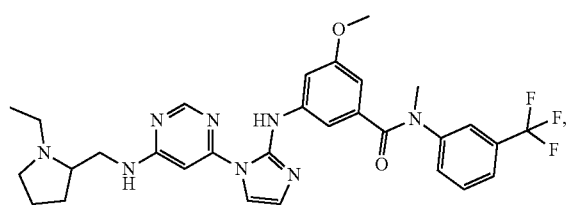
(I-8)
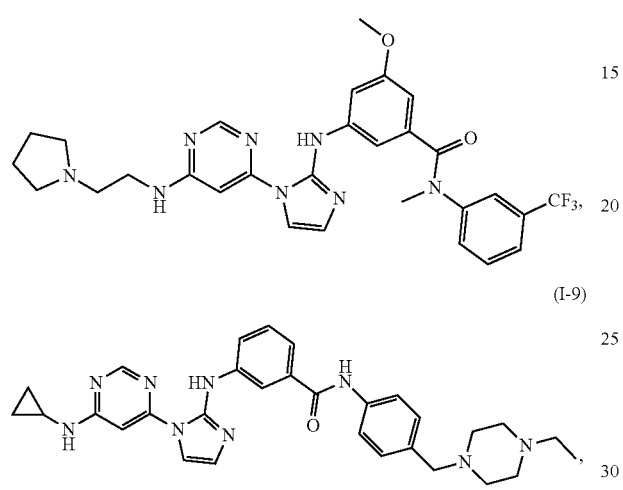
(I-9)
(I-10)
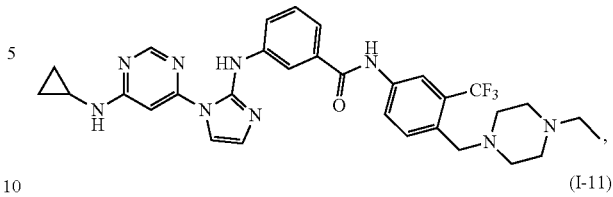
(I-11)
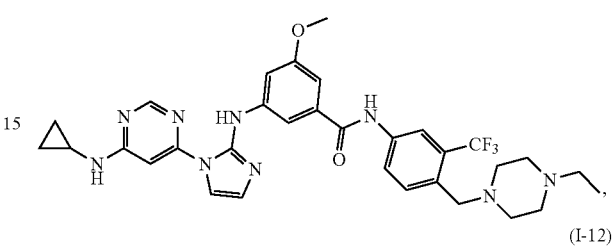
(I-12)
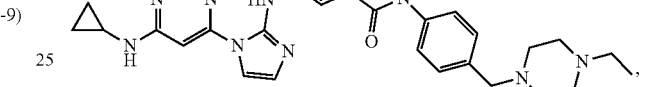
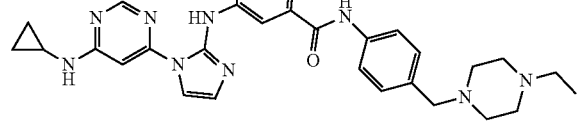
or a pharmaceutically acceptable salt, solvate, hydrate, polymorph, co-crystal, tautomer, stereoisomer, isotopically labeled derivative, or prodrug thereof.
In certain embodiments, a compound of Formula (I) is not of the formula:
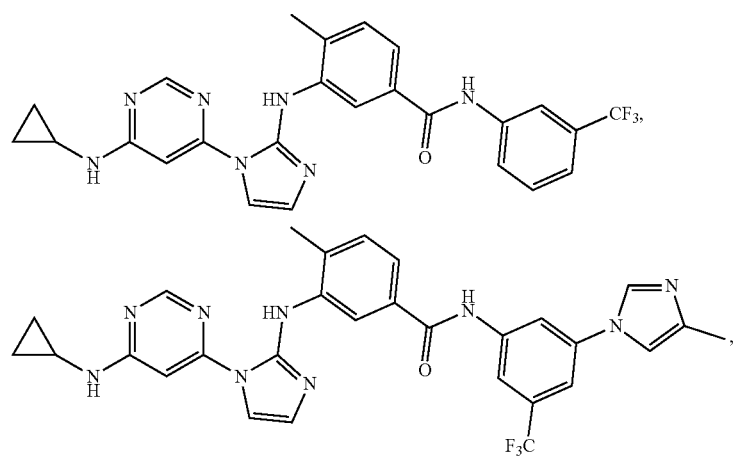
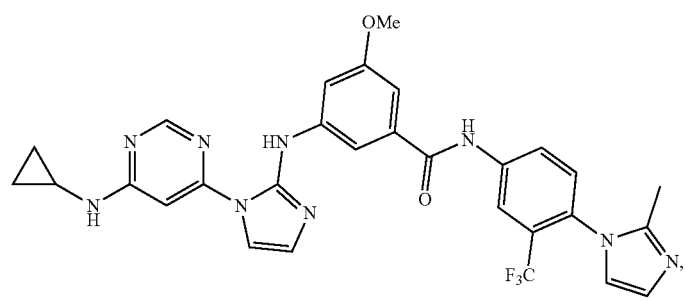

-continued

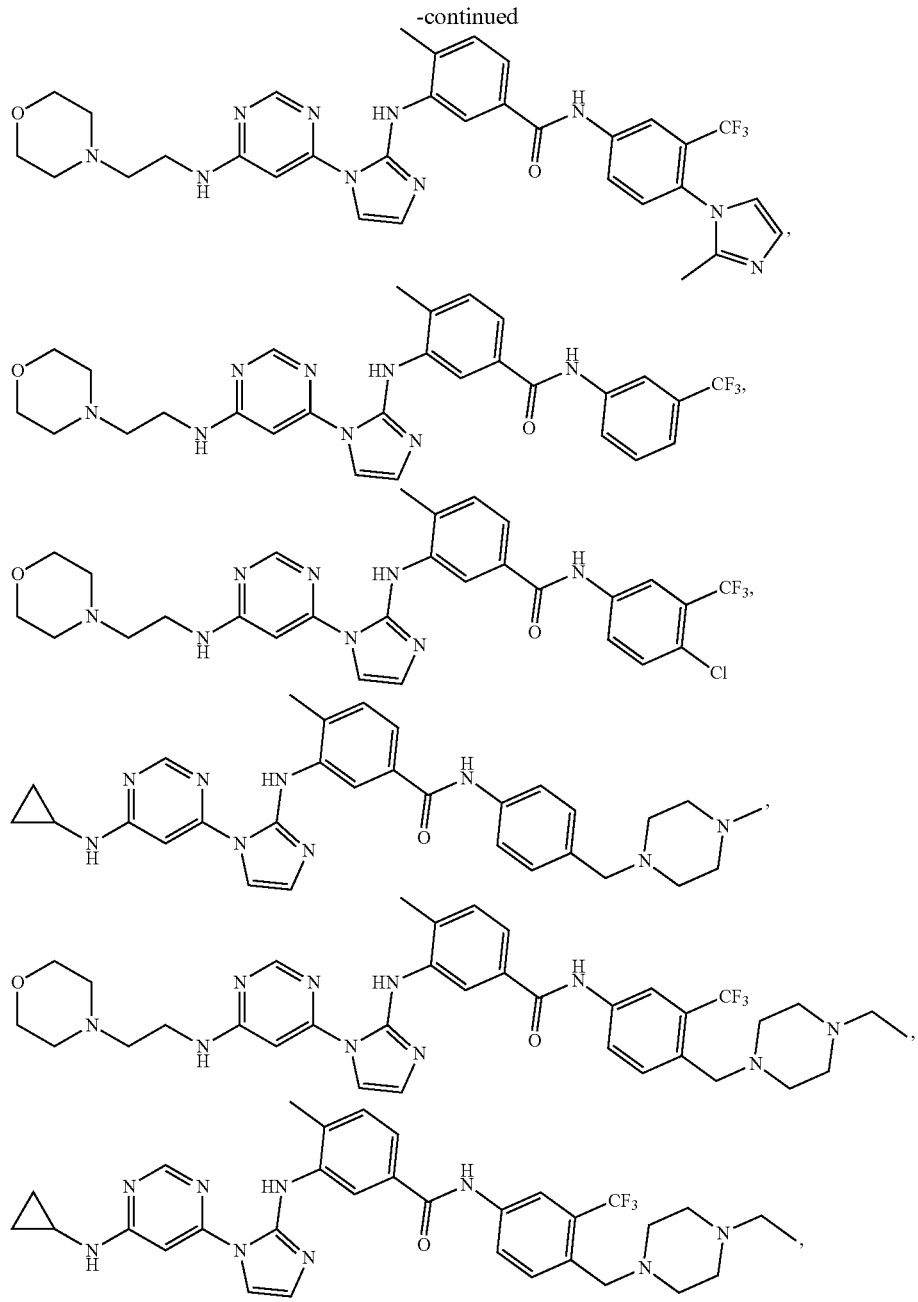

or a pharmaceutically acceptable salt, solvate, hydrate, polymorph, co-crystal, or tautomer thereof.

In certain embodiments, a compound described herein is a compound of Formula (I), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I), or a pharmaceutically acceptable salt thereof.

Certain compounds described herein bind protein kinases. In certain embodiments, the compounds described herein non-covalently bind to the protein kinase. In certain embodiments, the compounds described herein reversibly bind to the protein kinase. In certain embodiments, the compounds described herein non-reversibly bind to the protein kinase.

In certain embodiments, the compounds described herein modulate the activity of the protein kinase. In certain embodiments, the compounds described herein inhibit the activity of the protein kinase. In certain embodiments, the compounds described herein increase the activity of the protein kinase.

The binding affinity of a compound described herein to a protein kinase may be measured by the dissociation constant ($K_d$) value of an adduct of the compound and the protein kinase using methods known in the art (e.g., isothermal titration calorimetry (ITC)). In certain embodiments, the adduct comprises the compound and the protein kinase, which are bound (e.g., non-covalently) to each other. In certain embodiments, the $K_d$ value of the adduct is not more than about 100 μM, not more than about 10 μM, not more than about 1 μM, not more than about 100 nM, not more than about 10 nM, or not more than about 1 nM.

In certain embodiments, the activity of a protein kinase is inhibited by a compound described herein. The inhibition of the activity of a protein kinase by a compound described herein may be measured by the half maximal inhibitory concentration ($IC_{50}$) value of the compound when the compound, or a pharmaceutical composition thereof, is contacted, directly or indirectly, with the protein kinase. The $IC_{50}$ values may be obtained using methods known in the art (e.g., by a competition binding assay). In certain embodiments, the $IC_{50}$ value of a compound described herein is not more than about 1 mM, not more than about 100 μM, not more than about 10 μM, not more than about 1 μM, not more than about 100 nM, not more than about 10 nM, or not more than about 1 nM.

The compounds described herein may selectively modulate the activity of a protein kinase. In certain embodiments, the compounds selectively inhibit the activity of a protein kinase. In certain embodiments, the compounds selectively increase the activity of a protein kinase. In certain embodiments, the compounds inhibit the activity of two or more protein kinases to the same extent. In certain embodiments, the compounds increase the activity of two or more protein kinases to the same extent.

The selectivity of a compound described herein in inhibiting the activity of a first protein kinase over a second protein kinase may be measured by the quotient of the $IC_{50}$ value of the compound in inhibiting the activity of the second protein kinase over the $IC_{50}$ value of the compound in inhibiting the activity of the first protein kinase. The selectivity of a compound described herein in modulating the activity of a first protein kinase over a second protein kinase may also be measured by the quotient of the $K_d$ value of an adduct of the compound and the second protein kinase over the $K_d$ value of an adduct of the compound and the first protein kinase. In certain embodiments, the selectivity is at least about 2-fold, at least about 3-fold, at least about 5-fold, at least about 10-fold, at least about 30-fold, at least about 50-fold, at least about 100-fold, at least about 300-fold, at least about 500-fold, at least about 1,000-fold, at least about 3,000-fold, at least about 5,000-fold, at least about 10,000-fold, at least about 30,000-fold, or at least about 100,000-fold.

It is expected that the compounds described herein may be useful in treating and/or preventing diseases associated with aberrant activity (e.g., increased activity or decreased activity) of a protein kinase. It is known in the art that protein kinases are implicated in a wide range of diseases, such as proliferative diseases, genetic diseases, hematological diseases, neurological diseases, painful conditions, psychiatric disorders, and metabolic disorders. Therefore, the compounds described herein are expected to be useful in treating and/or preventing proliferative diseases, genetic diseases, hematological diseases, neurological diseases, painful conditions, psychiatric disorders, and/or metabolic disorders.

Methods of Preparing the Compounds

Imidazolyl compounds of Formula (I) may be prepared using amination reactions (e.g., displacement reactions between an amine and a leaving group). In another aspect, the present disclosure provides methods of preparing a compound described herein, the methods including aminating a compound of Formula (A), or a salt thereof, with an amine of Formula (B), or a salt thereof:

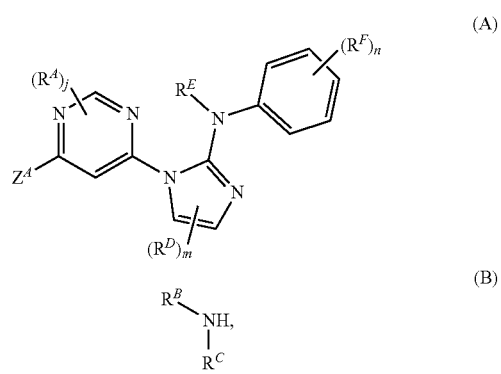

wherein $Z^A$ is a leaving group.

In certain embodiments, $Z^A$ is halogen. In certain embodiments, $Z^A$ is F. In certain embodiments, $Z^A$ is Cl. In certain embodiments, $Z^A$ is Br. In certain embodiments, $Z^A$ is I (iodine). In certain embodiments, $Z^A$ is —OS(=O)$R^{Z1}$, wherein $R^{Z1}$ is substituted or unsubstituted $C_{1-6}$ alkyl or substituted or unsubstituted phenyl. In certain embodiments, $Z^A$ is —OS(=O)$_2R^{Z1}$, wherein $R^{Z1}$ is substituted or unsubstituted $C_{1-6}$ alkyl or substituted or unsubstituted phenyl. In certain embodiments, $Z^A$ is —OMs. In certain embodiments, $Z^A$ is —OTf. In certain embodiments, $Z^A$ is —OTs. In certain embodiments, $Z^A$ is —OBs. In certain embodiments, $Z^A$ is 2-nitrobenzenesulfonyloxy.

In certain embodiments, a method of preparing a compound described herein further includes aminating a pyrimidine derivative of Formula (C), or a salt thereof, with an imidazole derivative of Formula (D), or a salt thereof, to provide the compound of Formula (A), or salt thereof:

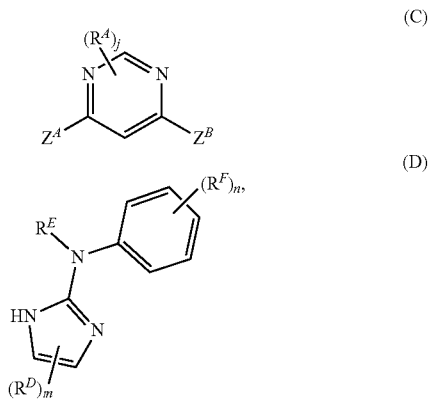

wherein $Z^B$ is a leaving group.

In certain embodiments, $Z^B$ is halogen. In certain embodiments, $Z^B$ is F. In certain embodiments, $Z^B$ is Cl. In certain embodiments, $Z^B$ is Br. In certain embodiments, $Z^B$ is I (iodine). In certain embodiments, $Z^B$ is —OS(=O)$R^{Z2}$, wherein $R^{Z2}$ is substituted or unsubstituted $C_{1-6}$ alkyl or substituted or unsubstituted phenyl. In certain embodiments, $Z^B$ is —OS(=O)$_2R^{Z2}$, wherein $R^{Z2}$ is substituted or unsubstituted $C_{1-6}$ alkyl or substituted or unsubstituted phenyl. In certain embodiments, $Z^B$ is —OMs. In certain embodiments, $Z^B$ is —OTf. In certain embodiments, $Z^B$ is —OTs. In certain embodiments, $Z^B$ is —OBs. In certain embodiments, $Z^B$ is 2-nitrobenzenesulfonyloxy.

In certain embodiments, $Z^A$ and $Z^B$ are the same. In certain embodiments, $Z^A$ and $Z^B$ are different. In certain embodiments, each of $Z^A$ and $Z^B$ is independently halogen. In certain embodiments, each of $Z^A$ and $Z^B$ is Cl.

Pharmaceutical Compositions, Kits, and Administration

The present disclosure provides pharmaceutical compositions comprising a compound of Formula (I), or a pharmaceutically acceptable salt thereof, and optionally a pharmaceutically acceptable excipient. In certain embodiments, the pharmaceutical composition described herein comprises a compound of Formula (I), or a pharmaceutically acceptable salt thereof, and a pharmaceutically acceptable excipient.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for treating a hematological disease in a subject in need thereof. In certain embodiments, the effective amount is an amount effective for preventing a hematological disease in a subject in need thereof. In certain embodiments, the effective amount is an amount effective for treating a neurological disease in a subject in need thereof. In certain embodiments, the effective amount is an amount effective for preventing a neurological disease in a subject in need thereof. In certain embodiments, the effective amount is an amount effective for treating a in a painful condition subject in need thereof. In certain embodiments, the effective amount is an amount effective for preventing a painful condition in a subject in need thereof. In certain embodiments, the effective amount is an amount effective for treating a psychiatric disorder in a subject in need thereof. In certain embodiments, the effective amount is an amount effective for preventing a psychiatric disorder in a subject in need thereof. In certain embodiments, the effective amount is an amount effective for treating a metabolic disorder in a subject in need thereof. In certain embodiments, the effective amount is an amount effective for preventing a metabolic disorder in a subject in need thereof. In certain embodiments, the effective amount is an amount effective for inhibiting the activity (e.g., aberrant activity, such as increased activity) of a protein kinase in a subject or cell. The cell may be in vitro or in vivo.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

In certain embodiments, the effective amount is an amount effective for inhibiting the activity of a protein kinase by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of a protein kinase by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the activity of a protein kinase by a range between a percentage described in this paragraph and another percentage described in this paragraph, inclusive.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, and/or in inhibiting the activity of a protein kinase in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which are different from the compound or composition and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, genetic disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is an binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, genetic disease, hematological disease, neurological disease, painful condition, psychiatric disorder, or metabolic disorder) in a subject in need thereof. In certain embodiments, the kits are useful for preventing a disease (e.g., proliferative disease, genetic disease, hematological disease, neurological disease, painful condition, psychiatric disorder, or metabolic disorder) in a subject in need thereof. In certain embodiments, the kits are useful for inhibiting the activity (e.g., aberrant activity, such as increased activity) of a protein kinase in a subject or cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, genetic disease, hematological disease, neurological disease, painful condition, psychiatric disorder, or metabolic disorder) in a subject in need thereof. In certain embodiments, the kits and instructions provide for preventing a disease (e.g., proliferative disease, genetic disease, hematological disease, neurological disease, painful condition, psychiatric disorder, or metabolic disorder) in a subject in need thereof. In certain embodiments, the kits and instructions provide for modulating (e.g., inhibiting) the activity (e.g., aberrant activity, such as increased activity) of a protein kinase in a subject or cell. A kit described herein may include one or more additional pharmaceutical agents described herein as a separate composition.

Methods of Treatment

The present disclosure provides methods of modulating (e.g., inhibiting or increasing) the activity (e.g., aberrant activity, such as increased or decreased activity) of a protein kinase in a subject or cell. The present disclosure also provides methods for the treatment of a wide range of diseases, such as diseases associated with aberrant activity (e.g., increased or decreased activity) of a protein kinase, proliferative diseases, genetic diseases, hematological diseases, neurological diseases, painful conditions, psychiatric disorders, and metabolic disorders in a subject in need thereof.

In another aspect, the present disclosure provides methods of modulating the activity of a protein kinase in a subject or cell. In certain embodiments, provided are methods of inhibiting the activity of a protein kinase in a subject. In certain embodiments, provided are methods of inhibiting the activity of a protein kinase in a cell. In certain embodiments, provided are methods of increasing the activity of a protein kinase in a subject. In certain embodiments, provided are methods of increasing the activity of a protein kinase in a cell. In certain embodiments, the activity of a protein kinase in a subject or cell is inhibited by a method described herein by at least about 1%, at least about 3%, at least about 10%, at least about 20%, at least about 30%, at least about 40%, at least about 50%, at least about 60%, at least about 70%, at least about 80%, or at least about 90%. In certain embodiments, the activity of a protein kinase in a subject or cell is increased by a method described herein by at least about 1%, at least about 3%, at least about 10%, at least about 20%, at least about 30%, at least about 40%, at least about 50%, at least about 60%, at least about 70%, at least about 80%, or at least about 90%. In some embodiments, the activity of a protein kinase in a subject or cell is selectively inhibited by the method. In some embodiments, the activity of a protein kinase in a subject or cell is selectively increased by the method.

Another aspect of the present disclosure relates to methods of treating a disease in a subject in need thereof.

In certain embodiments, the disease is a disease associated with a protein kinase. In certain embodiments, the disease is a disease associated with the activity of a protein kinase. In certain embodiments, the disease is a disease associated with the aberrant activity of a protein kinase. In certain embodiments, the disease is a disease associated with the increased activity of a protein kinase. In certain embodiments, the disease is a disease associated with the decreased activity of a protein kinase.

In certain embodiments, the disease is a proliferative disease. In certain embodiments, the disease is cancer. In certain embodiments, the disease is a benign neoplasm. In certain embodiments, the disease is or is associated with pathological angiogenesis. In certain embodiments, the disease is an inflammatory disease. In certain embodiments, the disease is an autoimmune disease. In certain embodiments, the disease is a genetic disease. In certain embodiments, the disease is a hematological disease. In certain embodiments, the disease is a neurological disease. In certain embodiments, the disease is a painful condition. In certain embodiments, the disease is a psychiatric disorder. In certain embodiments, the disease is a metabolic disorder.

In still another aspect, the present disclosure provides methods of preventing a disease described herein in a subject.

In certain embodiments, the methods of the disclosure include administering to a subject in need thereof an effective amount of a compound or pharmaceutical composition described herein. In certain embodiments, the methods of the disclosure include administering to a subject in need thereof a therapeutically effective amount of a compound or pharmaceutical composition described herein. In certain embodiments, the methods of the disclosure include administering to a subject in need thereof a prophylactically effective amount of a compound or pharmaceutical composition described herein. In certain embodiments, the methods of the disclosure include contacting a cell with an effective amount of a compound or pharmaceutical composition described herein.

Methods of Screening a Library of Compounds

Another aspect of the disclosure relates to methods of screening a library of compounds, and pharmaceutical acceptable salts thereof, to identify a compound, or a pharmaceutical acceptable salt thereof, that is useful in a method described herein. In certain embodiments, the methods of screening a library include obtaining at least two different compounds described herein; and performing at least one assay using the different compounds described herein. In certain embodiments, at least one assay is useful in identifying a compound that is useful in a method described herein.

Typically, the methods of screening a library of compounds involve at least one assay. In certain embodiments, the assay is performed to detect one or more characteristics associated with the treatment and/or prevention of a disease described herein or with the modulation (e.g., inhibition) of the activity of a protein kinase. The characteristics may be desired characteristics (e.g., a disease having been treated, a disease having been prevented, or the activity of a protein kinase having been modulated). The characteristics may be undesired characteristics (e.g., a disease having not been treated, a disease having not been prevented, or the activity of a protein kinase having not been modulated). The assay may be an immunoassay, such as a sandwich-type assay, competitive binding assay, one-step direct test, two-step test, or blot assay. The step of performing at least one assay may be performed robotically or manually.

In certain embodiments, the assay comprises (a) contacting a library of compounds with a protein kinase; and (b) detecting the binding of the library of compounds to the protein kinase. In certain embodiments, the assay comprises detecting the specific binding of the library of compounds to the protein kinase. In certain embodiments, the detected binding of the library of compounds to the protein kinase is useful in identifying the compound that is useful in a method described herein. In certain embodiments, the step of detecting the binding comprises using differential scanning fluorimetry (DSF), isothermal titration calorimetry (ITC), and/or an amplified luminescence proximity homogeneous assay (ALPHA). The step of performing at least one assay may be performed in a cell in vitro or in vivo.

Uses

In another aspect, the present disclosure provides the compounds described herein for use in a method described herein (e.g., a method of inhibiting a protein kinase, a method of treating a disease (e.g., a proliferative disease), a method of preventing a disease (e.g., a proliferative disease), or a method of screening a library of compounds).

In still another aspect, the present disclosure provides the pharmaceutical compositions described herein for use in a method described herein (e.g., a method of inhibiting a protein kinase, a method of treating a disease (e.g., a proliferative disease), a method of preventing a disease (e.g., a proliferative disease), or a method of screening a library of compounds).

EXAMPLES

In order that the disclosure may be more fully understood, the following examples are set forth. The synthetic and biological examples described in this application are offered to illustrate the compounds, pharmaceutical compositions, and methods provided herein and are not to be construed in any way as limiting their scope.

Example 1. Preparation of Compounds

The compounds provided herein can be prepared from readily available starting materials using the following general methods and procedures (e.g., the method shown in Scheme 1). It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization.

Scheme 1. An exemplary preparation of the compounds described herein

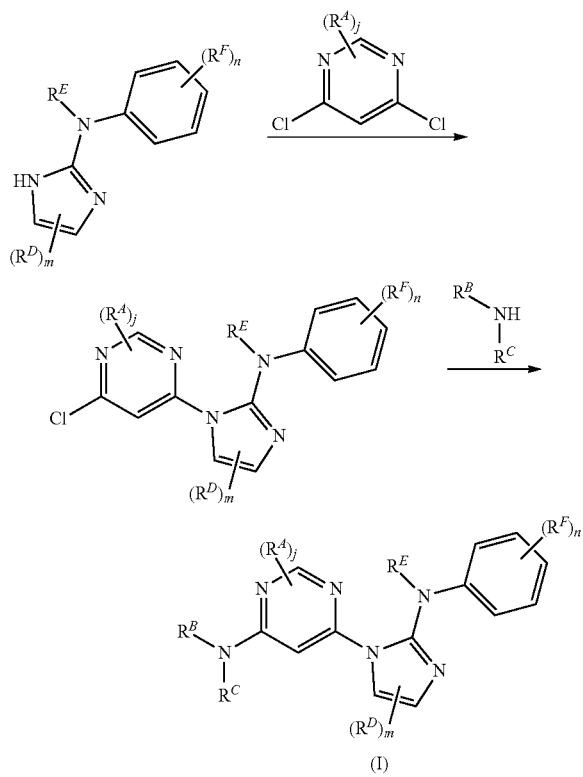

Example 1.1. Preparation of Compound I-1

In one set of experiments, compound I-1 was prepared according to the method shown in Scheme 1. All reactions were monitored by thin layer chromatography (TLC) with 0.25 mm E. Merck pre-coated silica gel plates (60 $F_{254}$) and Waters LCMS system (Waters 2489 UV/Visible Detector, Waters 3100 Mass, Waters 515 HPLC pump, Waters 2545 Binary Gradient Module, Waters Reagent Manager, Waters 2767 Sample Manager) using SUNFIRE $C_{18}$ column (4.6× 50 mm, 5 µM particle size): solvent gradient=97% A at 0 min, 1% A at 5 min; solvent A=0.035% TFA in water; solvent B=0.035% TFA in acetonitrile; flow rate=2.5 mL/min. Retention time (Rt) was determined using the above Waters LC/MS system. Purification of reaction products was carried out by flash chromatography using COMBIFLASH Rf with Teledyne Isco REDISEP Rf High Performance Gold or Silicycle SILIASEP High Performance columns (4 g, 12 g, 24 g, 40 g, or 80 g). The purity of all compounds was over 95% and was analyzed with Waters LCMS system. $^1$H NMR and $^{13}$C NMR spectra were obtained using a Varian Inova-600 (600 MHz for $^1$H, and 125 MHz for $^{13}$C) spectrometer. Chemical shifts are reported relative to chloroform (δ=7.24 ppm) or dimethyl sulfoxide (δ=2.50 ppm) for $^1$H NMR and relative to dimethyl sulfoxide (δ=39.51 ppm) for $^{13}$C NMR. Data are reported as: br=broad, s=singlet, d=doublet, t=triplet, q=quartet, m=multiplet.

N-(2,6-dimethylphenyl)-1H-imidazol-2-amine

To a solution of cyanogen bromide (25 g, 236.03 mmol) in hexane (80 mL) was added a solution of the aminoacetaldehyde diethyl acetal (34.3 mL, 236.03 mmol) in diethyl ether (80 mL) at room temperature. The resulting mixture was stirred overnight. A white solid was formed and was removed by filtration and washed with diethyl ether. The filtrate was concentrated and purified by flash chromatography on silica gel (eluted with 0/100 to 5/95 methanol/dichloromethane) to afford N-(2,2-diethyloxyethyl)carbodiimide (27 g, 72% yield) as a bright yellow oil. Rt (retention time)=1.82 min; MS m/z: 159.20 [M+1].

To a solution of 2,6-dimethylaniline (5.0 g, 41.29 mmol) and N-(2,2-diethyloxyethyl)carbodiimide (7.8 g, 49.55 mmol) in ethanol (100 mL) was added methanesulfonic acid (3.2 mL, 49.55 mL). The resulting mixture was refluxed for 20 h, concentrated, and dissolved in a 6.0 N HCl solution (30 mL). After stirring for 8 h, the resulting mixture was neutralized with a 10 N NaOH solution at 0° C. to pH 6. A saturated sodium carbonate solution was added so that the pH of the resulting mixture was about 13. A solid was produced and was filtered and dried to afford N-(2,6-dimethylphenyl)-1H-imidazol-2-amine (3.8 g, 49% yield). Rt=1.57 min; $^1$H NMR (600 MHz; DMSO-d$_6$) δ 10.25 (s, 1H), 7.28 (s, 1H), 6.97 (m, 2H), 6.92 (m, 1H), 6.49 (s, 1H), 6.36 (s, 1H), 2.07 (s, 6H) ppm; MS m/z: 188.23 [M+1].

1-(6-Chloropyrimidin-4-yl)-N-(2,6-dimethylphenyl)-1H-imidazol-2-amine

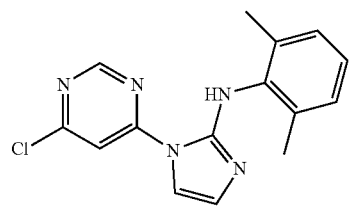 [SMILES: Cc1cccc(C)c1Nc1nccn1-c1cc(Cl)ncn1]

To a solution of N-(2,6-dimethylphenyl)-1H-imidazol-2-amine (1.0 g, 5.34 mmol) and N,N-diisopropylethylamine (1.8 mL, 10.69 mmol) in 2-butanol (10 mL) was added 4,6-dichloropyrimidine (1.2 g, 8.02 mmol). The resulting mixture was heated at 120° C. overnight, cooled, and partitioned between a saturated aqueous potassium carbonate solution and a mixed solvents of CHCl$_3$/2-propanol (4/1). The organic phase was separated, dried over anhydrous sodium sulfate, filtered through a pad of CELITE, and concentrated. The residue was purified by flash chromatography on silica gel (eluted with 1/99 to 5/95 ammonia (7.0 N in methanol) in methanol/dichloromethane) to afford 1-(6-chloropyrimidin-4-yl)-N-(2,6-dimethylphenyl)-1H-imidazol-2-amine (1.3 g, 81% yield) as an off-white solid.

Rt=1.97 min, $^1$H NMR (600 MHz; DMSO-$d_6$) δ 9.46 (s, 1H), 9.01 (d, J=4.2 Hz, 1H), 8.15 (d, J=4.2 Hz, 1H), 7.71 (m, 1H), 7.16 (m, 3H), 6.70 (s, 1H), 2.25 (m, 6H) ppm; MS m/z: 300.19 [M+1].

6-(2-((2,6-Dimethylphenyl)amino)-1H-imidazol-1-yl)-N-(4-(4-ethylpiperazin-1-yl)phenyl)pyrimidin-4-amine (I-1)

To a solution of 1-(6-chloropyrimidin-4-yl)-N-(2,6-dimethylphenyl)-1H-imidazol-2-amine (100 mg, 0.33 mmol) and 4-(4-ethylpiperazin-1-yl)aniline (68 mg, 0.33 mmol) in 2-butanol (1 mL) was added trifluoroacetic acid (TFA, 0.1 mL). The resulting mixture was stirred at 120° C. for 4 h, concentrated, and diluted with dimethyl sulfoxide (6 mL). The resulting mixture was purified with preparative HPLC to afford 6-(2-((2,6-dimethylphenyl)amino)-1H-imidazol-1-yl)-N-(4-(4-ethylpiperazin-1-yl)phenyl)pyrimidin-4-amine TFA salt (78 mg, 41% yield) as an off-white solid. Rt=1.93 min; $^1$H NMR (600 MHz; DMSO-$d_6$) δ 10.71 (br, 1H), 10.02 (s, 1H), 9.97 (br, 1H), 8.54 (s, 1H), 7.65 (s, 1H), 7.48 (d, J=6.6 Hz, 2H), 7.20 (m, 4H), 7.10 (s, 1H), 7.01 (d, J=9.0 Hz, 2H), 6.95 (s, 1H), 3.78 (m, 2H), 3.56 (m, 2H), 3.17 (m, 2H), 3.09 (m, 2H), 2.94 (m, 2H), 2.18 (s, 6H), 1.23 (m, 3H) ppm; MS m/z: 469.46 [M+1].

Example 1.2. Preparation of Compounds I-2 to I-12

In another set of experiments, compounds I-2 to I-12 were prepared using methods similar to the ones of Example 1.1. Exemplary analytical data of these compounds are shown in Table 1.

TABLE 1

Exemplary analytical data of compounds I-2 to I-12

| Compound | LC/MS retention time (min) | MS m/z, [M + 1]$^+$ |
| --- | --- | --- |
| I-2 | 3.05 | 451.31 |
| I-3 | 3.02 | 431.40 |
| I-4 | 2.73 | 381.31 |
| I-5 |  | 581.7 |
| I-6 |  | 567.7 |
| I-7 |  | 594.7 |
| I-8 |  | 581.6 |
| I-9 |  | 537.7 |
| I-10 |  | 606.7 |
| I-11 |  | 636.6 |
| I-12 |  | 552.7 |

Example 2. Protein Kinase Assays of the Compounds

In another set of experiments, the activities of the compounds described herein against various protein kinases were determined according to the methods reported in Hastie et al., *Nature Protocols*, 2006, 1, 968-971.

Materials

Enzyme Dilution Buffer.

This buffer consisted of 50 mM Tris-HCl, pH 7.5, 0.1 mM EGTA, 1 mg ml$^{-1}$ bovine serum albumin and 0.1% (vol/vol) 2-mercaptoethanol.

10× Concentrated Assay Buffer.

An assay buffer of 500 mM Tris-HCl, pH 7.5, 1 mM EGTA, and 100 mM magnesium acetate was used for assay of a wide variety of protein kinases. In some experiments, other cofactors were included (e.g., calcium ions and calmodulin were included for assay of calcium-calmodulin-dependent protein kinases). In some cases, the pH of the buffer was changed (e.g., phosphorylase kinase had an optimum pH of 8.6).

1 mM [γ-$^{32}$P] ATP.

The specific activity of the [γ-$^{32}$P] ATP solution was 1×10$^5$ to 1×10$^6$ c.p.m. per nmol depending on what was needed to produce an optimal signal/noise ratio. Stocks of nonradioactive ("cold") ATP were dissolved in 10 mM HEPES, and the pH of the resulting stock solutions was adjusted to 7.4. To measure the concentration of ATP, a sample of such a stock solution was diluted to 20 μM, and the absorbance of the diluted sample was measured at 259 nm. The absorbance of a 20-μM stock solution of ATP at 259 nm was about 0.31. The 1-mM solution of cold ATP was "spiked" with [γ-$^{32}$P] ATP to produce a radioactivity of 1×10$^5$ to 1×10$^6$ c.p.m. per nmol.

Procedure

1) The number of assay samples needed was determined based on, e.g., the following considerations: (i) each condition was assayed in duplicate; (ii) two controls containing peptide or protein substrate and ATP but no protein kinase were included to assess contamination by any free ATP not incorporated into substrate, alongside two controls lacking a peptide or protein substrate but containing ATP and protein kinase to correct for any incorporation of phosphate into the kinase itself (e.g., autophosphorylation); and (iii) a maximum of 40 samples were assayed manually at one time by a single person. Microcentrifuge tubes were label distinctly and were placed on ice.

2) Suspend a wire mesh basket in a beaker containing a magnetic stir bar and not less than 5 ml of 75 mM phosphoric acid per assay sample or a minimum volume of 100 ml. Place this on a magnetic stirrer behind a plexiglass shield.

3) Label 2 cm×2 cm squares of phosphocellulose paper corresponding to the samples to be pipetted into each microcentrifuge tube. Label the phosphocellulose paper using pencil, which was not affected by the solvents used to wash the papers at the end of the assay.

4) Dilute the protein kinase in enzyme dilution buffer and place on ice.

5) Pipette 5 μl of 10× concentrated assay buffer, 5 μl peptide or protein substrate (the two "no-substrate" control tubes had 5 μl water added instead of peptide or protein substrate), and 30 μl distilled water into each tube. Keep the tubes on ice.

6) Add 5 μl diluted protein kinase to each tube, except for the two "no-enzyme" control tubes, which had 5 μl enzyme dilution buffer added, and still keeping the tubes on ice. In some cases, premixed "cocktails" of assay components were prepared containing peptide or protein substrate, assay buffer, and distilled water to limit the number of additions to each assay tube.

Each of steps 7 to 14 was done behind a plexiglass shield.

7) Insert each tube into the water bath at intervals of 15 s to allow the assay mixture to reach 30° C. Begin the protein kinase reactions by adding 5 μl of 1 mM [γ-$^{32}$P] ATP to each tube at intervals of 15 s. Close each tube, vortex for 1 s to mix the contents and immediately replace in a rack in the water bath. Incubate for 10 min at 30° C.

8) At 10 min after the addition of ATP, remove each tube from the water bath at intervals of 15 s.

9) "Spot" 40 μl of each reaction mixture onto the center of a 2-cm square of P81 phosphocellulose paper using forceps to handle the paper squares. Immediately immerse the paper into the 75 mM phosphoric acid contained in the wire mesh basket suspended in the beaker that is being stirred continuously with a magnetic stirrer. This was be done within 1 to 2 s, as this step terminated the reaction.

10) After 5 min, remove the wire mesh basket from the beaker, and discard the phosphoric acid in the beaker and replace it with fresh phosphoric acid. Replace the wire mesh basket in the beaker and repeat this washing procedure three times (with 5 min between each wash). This step removes the [γ-$^{32}$P] ATP that has not been incorporated into the peptide or protein substrate.

11) After the final wash in phosphoric acid, rinse the papers briefly with acetone to remove the phosphoric acid and either air-dry or dry with a hair dryer.

12) Transfer each paper to a new, distinctly labeled, 1.5-ml microcentrifuge tube.

13) Measure radioactivity in the samples by Cerenkov counting (e.g., without liquid scintillation fluid) in a liquid scintillation counter using a "$^{32}$P program". Also measure the radioactivity of 1-μl aliquots of the stock of 1 mM [γ-$^{32}$P] ATP in triplicate to determine the specific radioactivity of the ATP in terms of c.p.m. per nanomol ATP (1 μl of 1 mM ATP corresponds to 1 nmol ATP).

14) Calculate the activity of the protein kinase. One unit (U) of protein kinase activity is that amount that catalyzes the incorporation of 1 nmol phosphate into the standard peptide or protein substrate in 1 min. In the assay described herein, the activity of the undiluted protein kinase solution in U ml$^{-1}$ is [(r−b/sa)×d×1.25×200]/10, where r is the c.p.m. incorporated into the substrate in the protein kinase reaction, b is the average c.p.m. associated with the phosphocellulose paper in the reaction "blanks", sa is the specific radioactivity of the ATP (c.p.m. nmol$^{-1}$), d is the "fold dilution" of the protein kinase before assay, 1.25 is a correction for transfer of only 80% of the reaction to the phosphocellulose paper (40 μl of a 50-μl assay volume), 200 corrects for the addition of only 5 μl of diluted protein kinase to each assay, and 10 is the incubation time in min. In some cases, if the protein concentration of the assay was known, the activity was converted from U ml$^{-1}$ to U mg$^{-1}$ of protein.

In some experiments of determining the inhibitory activities of a compound described herein against select protein kinases (e.g, experiments yielding the data in Table 2), DMSO was used as a control. The activity of a protein kinase when treated with DMSO, but not with a compound described herein, was set to 100%. Compounds resulting in less than 100% activity of a protein kinase are deemed to be inhibitors of the protein kinase.

In some experiments, inhibitory activities of the compounds described herein against select protein kinases were determined as IC$_{50}$ values (e.g., IC$_{50}$ values in Table 3) using methods known in the art (e.g., the method developed by Invitrogen Technology).

Results

Exemplary results of the protein kinase assays of the compounds described herein are shown in Tables 2 and 3.

TABLE 2

Exemplary inhibitory activities of compound I-1 (1 μM or 0.1 μM) against select protein kinases as compared to control (DMSO)

| Protein kinase | Activity of the protein kinase when treated with compound I-1 (% control) | |
| --- | --- | --- |
| | 1 μM of compound I-1 | 0.1 μM of compound I-1 |
| ABL | 48 | 84 |
| BRK | 16 | 74 |
| BTK | 30 | 85 |
| CSK | 67 | 94 |
| DDR2 | 12 | 46 |
| EPH-A2 | 59 | 99 |
| EPH-B1 | 16 | 86 |
| FGF-R1 | 30 | 67 |
| HER4 | 76 | 97 |
| Lck | 13 | 24 |
| p38a MAPK | 28 | 87 |
| Src | 13 | 43 |
| TIE2 | 85 | 82 |
| VEG-FR | 31 | 81 |
| YES1 | 8 | 41 |
| ABL | 48 | 84 |
| BRK | 16 | 74 |
| BTK | 30 | 85 |
| CSK | 67 | 94 |
| DDR2 | 12 | 46 |
| EPH-A2 | 59 | 99 |
| EPH-B1 | 16 | 86 |
| FGF-R1 | 30 | 67 |
| HER4 | 76 | 97 |
| Lck | 13 | 24 |
| p38a MAPK | 28 | 87 |
| Src | 13 | 43 |
| TIE2 | 85 | 82 |
| VEG-FR | 31 | 81 |
| YES1 | 8 | 41 |

TABLE 3

Exemplary inhibitory activities of compounds I-1 to I-4 against select protein kinases

| Compound | Kinase | Concentration of ATP (μM) | IC$_{50}$ (nM) |
| --- | --- | --- | --- |
| I-1 | BTK | K$_m$ for ATP | 338 |
| I-1 | HCK | K$_m$ for ATP | 111 |
| I-2 | BTK | K$_m$ for ATP | 1860 |
| I-2 | HCK | K$_m$ for ATP | 307 |
| I-3 | BTK | K$_m$ for ATP | 9980 |
| I-3 | HCK | K$_m$ for ATP | 2420 |
| I-4 | BTK | K$_m$ for ATP | >10000 |
| I-4 | HCK | K$_m$ for ATP | 3000 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

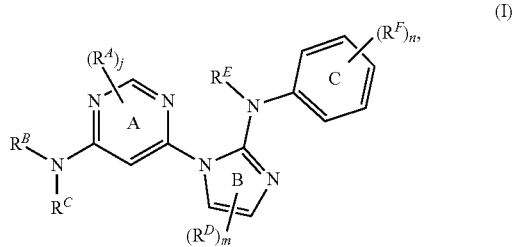

(I)

or a pharmaceutically acceptable salt thereof, wherein:

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —CN, —SCN, —$C(=NR^{A1})R^{A1}$, —$C(=NR^{A1})OR^{A1}$, —$C(=NR^{A1})N(R^{A1})_2$, —$C(=O)R^{A1}$, —$C(=O)OR^{A1}$, —$C(=O)N(R^{A1})_2$, —$NO_2$, —$NR^{A1}C(=O)R^{A1}$, —$NR^{A1}C(=O)OR^{A1}$, —$NR^{A1}C(=O)N(R^{A1})_2$, —$OC(=O)R^{A1}$, —$OC(=O)OR^{A1}$, or —$OC(=O)N(R^{A1})_2$, wherein each instance of $R^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1}$ are joined to form a substituted or unsubstituted heterocyclic or substituted or unsubstituted heteroaryl ring;

j is 0, 1, or 2;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted aryl, or substituted or unsubstituted heteroaryl;

$R^C$ is hydrogen, substituted or unsubstituted acyl, or substituted or unsubstituted $C_{1-6}$ alkyl;

each instance of $R^D$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{D1}$, —$N(R^{D1})_2$, —$SR^{D1}$, —CN, —SCN, —$C(=NR^{D1})R^{D1}$, —$C(=NR^{D1})OR^{D1}$, —$C(=NR^{D1})N(R^{D1})_2$, —$C(=O)R^{D1}$, —$C(=O)OR^{D1}$, —$C(=O)N(R^{D1})_2$, —$NO_2$, —$NR^{D1}C(=O)R^{D1}$, —$NR^{D1}C(=O)OR^{D1}$, —$NR^{D1}C(=O)N(R^{D1})_2$, —$OC(=O)R^{D1}$, —$OC(=O)OR^{D1}$, or —$OC(=O)N(R^{D1})_2$, wherein each instance of $R^{D1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{D1}$ are joined to form a substituted or unsubstituted heterocyclic or substituted or unsubstituted heteroaryl ring;

m is 0, 1, or 2;

$R^E$ is hydrogen, substituted or unsubstituted acyl, substituted or unsubstituted $C_{1-6}$ alkyl, or a nitrogen protecting group;

the first instance of $R^F$ is —$C(=O)N(R^{F1})_2$;

each remaining instance of $R^F$, if present, is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{F1}$, —N(R$^{F1}$)$_2$, —SR$^{F1}$, —CN, —SCN, —C(=NR$^{F1}$)R$^{F1}$, —C(=NR$^{F1}$)OR$^{F1}$, —C(=NR$^{F1}$)N(R$^{F1}$)$_2$, —C(=O)R$^{F1}$, —C(=O)OR$^{F1}$, —C(=O)N(R$^{F1}$)$_2$, —NO$_2$, —NR$^{F1}$C(=O)R$^{F1}$, —NR$^{F1}$C(=O)OR$^{F1}$, —NR$^{F1}$C(=O)N(R$^{F1}$)$_2$, —OC(=O)R$^{F1}$, —OC(=O)OR$^{F1}$, or —OC(=O)N(R$^{F1}$)$_2$, wherein each instance of R$^{F1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, an oxygen protecting group when attached to an oxygen atom, or a sulfur protecting group when attached to a sulfur atom, or two instances of R$^{F1}$ are joined to form a substituted or unsubstituted heterocyclic or substituted or unsubstituted heteroaryl ring; and n is 1, 2, 3, 4, or 5;

provided that the compound is not of the formula:

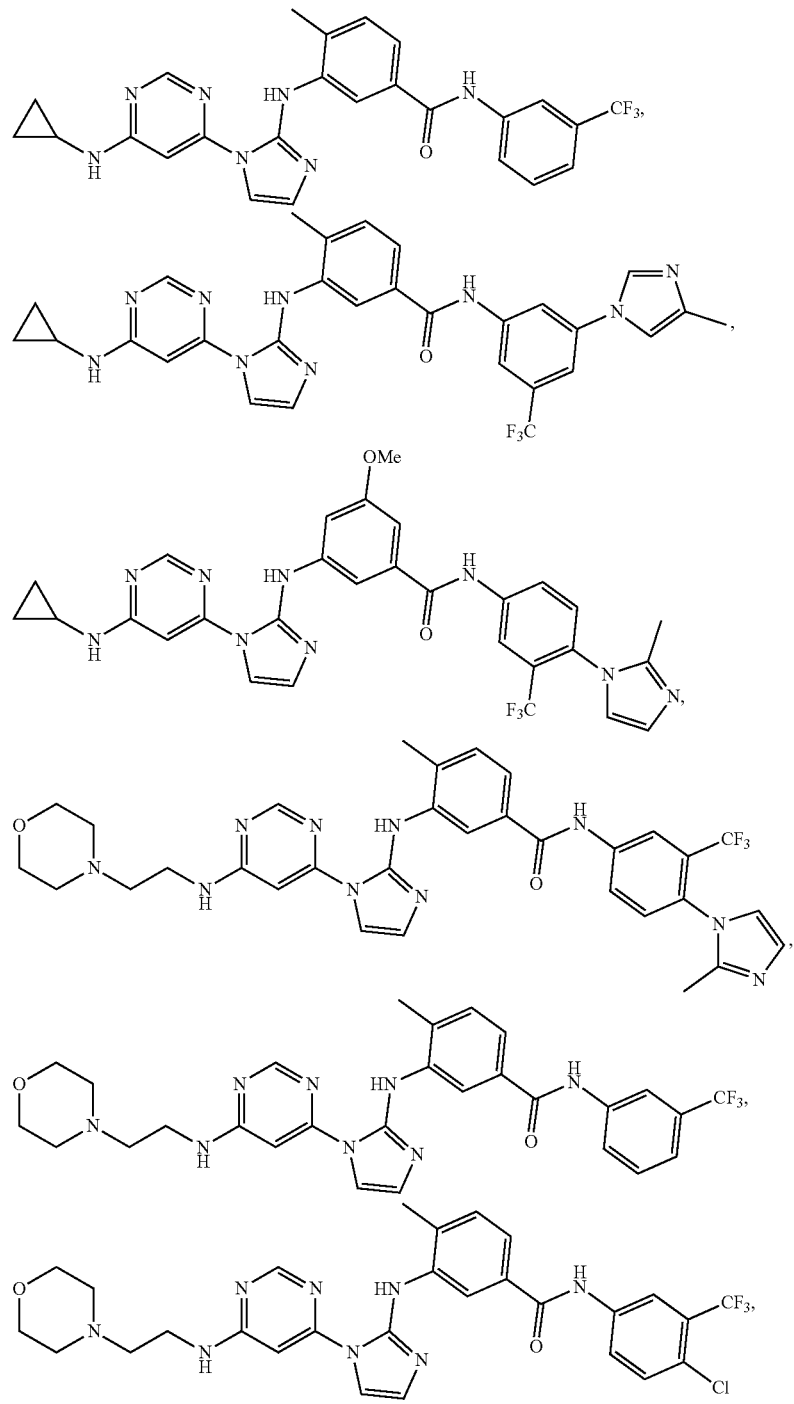

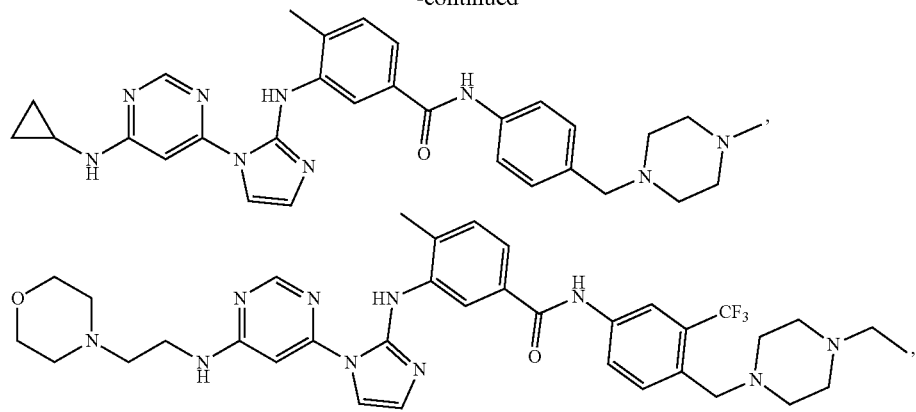

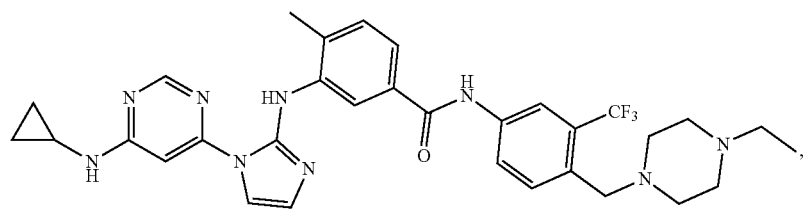

or

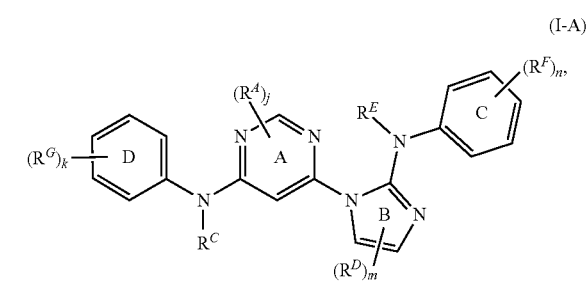

or a pharmaceutically acceptable salt thereof.

2. The compound of claim 1, wherein the compound is of Formula (I-A):

(I-A)

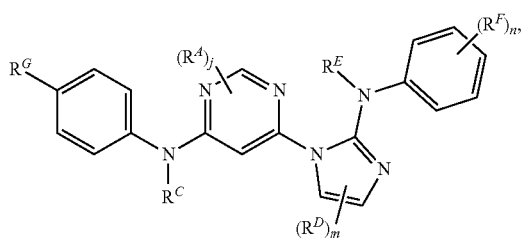

or a pharmaceutically acceptable salt thereof, wherein:
each instance of $R^G$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{G1}$, —$N(R^{G1})_2$, —$SR^{G1}$, —CN, —SCN, —C($=NR^{G1}$)$R^{G1}$, —C($=NR^{G1}$)$OR^{G1}$, —C($=NR^{G1}$)$N(R^{G1})_2$, —C($=O$)$R^{G1}$, —C($=O$)$OR^{G1}$, —C($=O$)$N(R^{G1})_2$, —$NO_2$, —$NR^{G1}$C($=O$)$R^{G1}$, —$NR^{G1}$C($=O$)$OR^{G1}$, —$NR^{G1}$C($=O$)$N(R^{G1})_2$, —OC($=O$)$R^{G1}$, —OC($=O$)$OR^{G1}$, or —OC($=O$)$N(R^{G1})_2$, wherein each instance of $R^{G1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{G1}$ are joined to form a substituted or unsubstituted heterocyclic or substituted or unsubstituted heteroaryl ring; and k is 0, 1, 2, 3, 4, or 5.

3. The compound of claim 2, wherein the compound is of the formula:

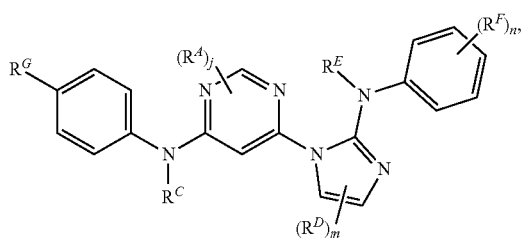

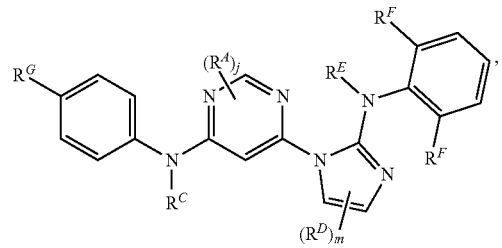

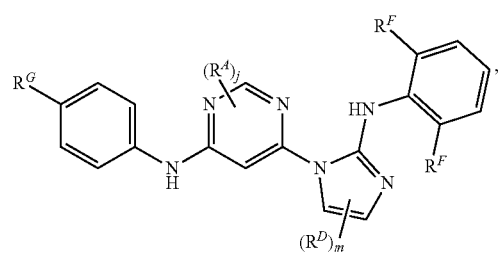

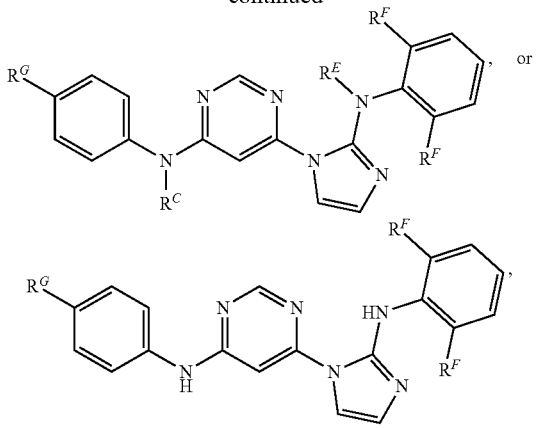

or a pharmaceutically acceptable salt thereof.

4. The compound of claim 2, or a pharmaceutically acceptable salt thereof, wherein at least one instance of $R^G$ is $-OR^{G1}$, $-N(R^{G1})_2$, or substituted or unsubstituted, 3- to 7-membered, monocyclic heterocyclyl, wherein one, two, or three atoms of the heterocyclic ring system are independently nitrogen, oxygen, or sulfur.

5. The compound of claim 1, wherein the compound is of Formula (I-B):

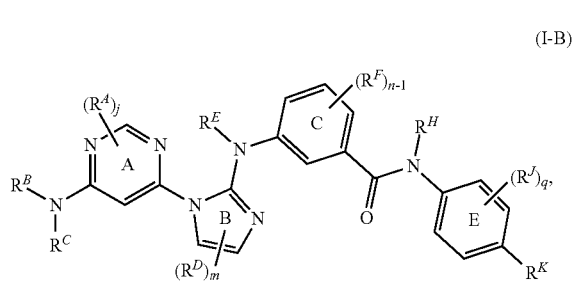

(I-B)

or a pharmaceutically acceptable salt thereof, wherein:
$R^H$ is hydrogen, substituted or unsubstituted acyl, or substituted or unsubstituted $C_{1-6}$ alkyl;
each instance of $R^J$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{J1}$, $-N(R^{J1})_2$, $-SR^{J1}$, $-CN$, $-SCN$, $-C(=NR^{J1})R^{J1}$, $-C(=NR^{J1})OR^{J1}$, $-C(=NR^{J1})N(R^{J1})_2$, $-C(=O)R^{J1}$, $-C(=O)OR^{J1}$, $-C(=O)N(R^{J1})_2$, $-NO_2$, $-NR^{J1}C(=O)R^{J1}$, $-NR^{J1}C(=O)OR^{J1}$, $-NR^{J1}C(=O)N(R^{J1})_2$, $-OC(=O)R^{J1}$, $-OC(=O)OR^{J1}$, or $-OC(=O)N(R^{J1})_2$, wherein each instance of $R^{J1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{J1}$ are joined to form a substituted or unsubstituted heterocyclic or substituted or unsubstituted heteroaryl ring;

q is 0, 1, 2, 3, or 4; and
$R^K$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{K1}$, $-N(R^{K1})_2$, $-SR^{K1}$, $-CN$, $-SCN$, $-C(=NR^{K1})R^{K1}$, $-C(=NR^{K1})OR^{K1}$, $-C(=NR^{K1})N(R^{K1})_2$, $-C(=O)R^{K1}$, $-C(=O)OR^{K1}$, $-C(=O)N(R^{K1})_2$, $-NO_2$, $-NR^{K1}C(=O)R^{K1}$, $-NR^{K1}C(=O)OR^{K1}$, $-NR^{K1}C(=O)N(R^{K1})_2$, $-OC(=O)R^{K1}$, $-OC(=O)OR^{K1}$, or $-OC(=O)N(R^{K1})_2$, wherein each instance of $R^{K1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{K1}$ are joined to form a substituted or unsubstituted heterocyclic or substituted or unsubstituted heteroaryl ring.

6. The compound of claim 1, or a pharmaceutically acceptable salt thereof, wherein $R^B$ is substituted or unsubstituted alkyl.

7. The compound of claim 1, or a pharmaceutically acceptable salt thereof, wherein $R^B$ is substituted or unsubstituted, 3- to 7-membered, monocyclic carbocyclyl.

8. The compound of claim 1, or a pharmaceutically acceptable salt thereof, wherein $R^B$ is substituted or unsubstituted, 5- to 6-membered, monocyclic heteroaryl, wherein one, two, three, or four atoms of the heteroaryl ring system are independently nitrogen, oxygen, or sulfur.

9. The compound of claim 1, or a pharmaceutically acceptable salt thereof, wherein $R^C$ is hydrogen.

10. The compound of claim 1, or a pharmaceutically acceptable salt thereof, wherein $R^E$ is hydrogen.

11. The compound of claim 1, or a pharmaceutically acceptable salt thereof, wherein at least one remaining instance of $R^F$ is halogen, substituted or unsubstituted $C_{1-6}$ alkyl, or $-OR^{F1}$, wherein $R^{F1}$ is hydrogen, substituted or unsubstituted $C_{1-6}$ alkyl, or an oxygen protecting group.

12. The compound of claim 1, or a pharmaceutically acceptable salt thereof, wherein each instance of $R^{F1}$ is independently hydrogen, substituted or unsubstituted $C_{1-6}$ alkyl, or substituted or unsubstituted phenyl.

13. The compound of claim 1, wherein the compound is of the formula:

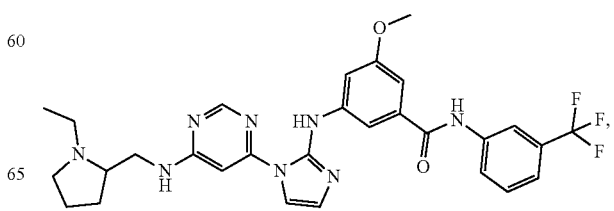

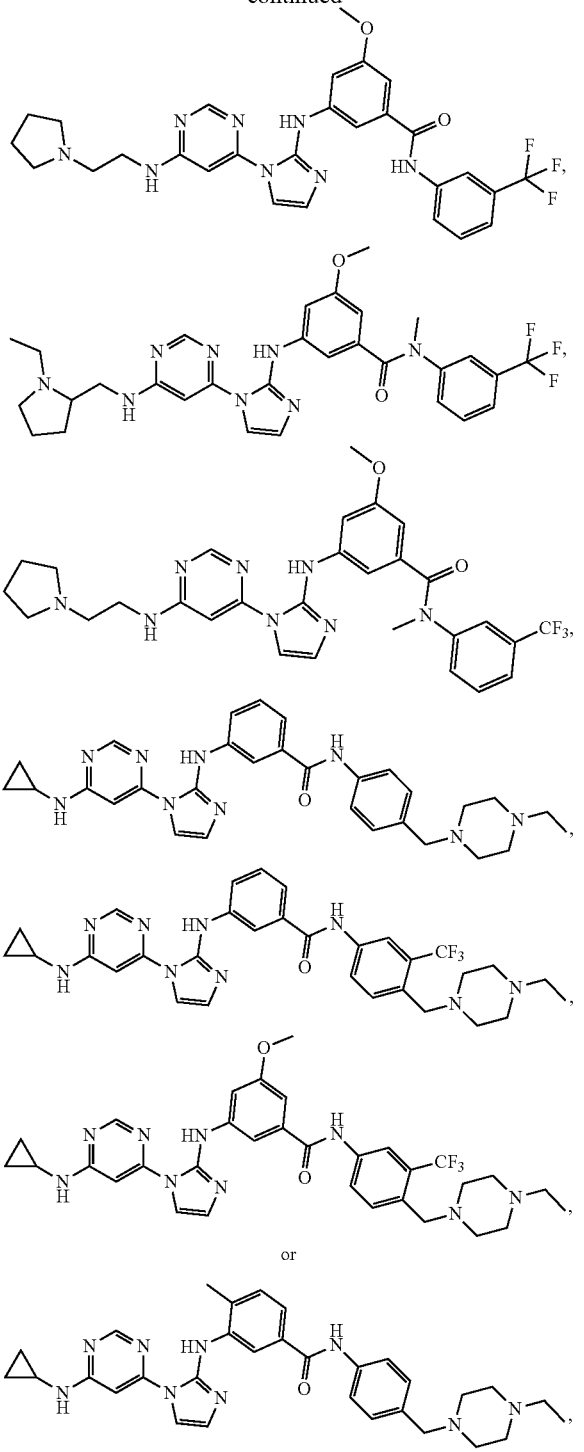

or a pharmaceutically acceptable salt thereof.

14. A pharmaceutical composition comprising a compound of claim 1, or a pharmaceutically acceptable salt thereof, and optionally a pharmaceutically acceptable excipient.

15. A method of preparing a compound of claim 1, or a pharmaceutically acceptable salt thereof, the method comprising aminating a compound of Formula (A), or a salt thereof, with an amine of Formula (B), or a salt thereof:

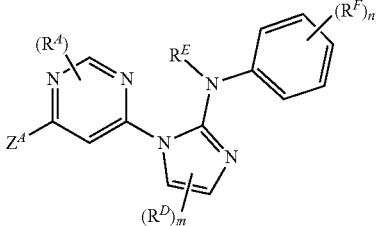

wherein $Z^A$ is a leaving group.

16. A method of treating a disease in a subject in need thereof, the method comprising administering to the subject a therapeutically effective amount of a compound of claim 1, or a pharmaceutically acceptable salt thereof, wherein the disease is a genetic disease, a proliferative disease, pathological angiogenesis, an inflammatory disease, an autoimmune disease, a hematological disease, a neurological disease, a painful condition, a psychiatric disorder, or a metabolic disorder.

17. A kit comprising:
   a compound of claim 1, or a pharmaceutically acceptable salt thereof; and
   instructions for using the compound or pharmaceutically acceptable salt.

18. A method of modulating the activity of a protein kinase in a subject or cell, the method comprising administering to the subject or contacting a cell with an effective amount of a compound of claim 1, or a pharmaceutically acceptable salt thereof.

19. A method of screening a library of compounds, the method comprising:
   obtaining at least two different compounds of claim 1, or pharmaceutically acceptable salts thereof; and
   performing at least one assay using the different compounds or pharmaceutically acceptable salts.

20. The compound of claim 1, or a pharmaceutically acceptable salt thereof, wherein $R^B$ is —(CH$_2$)$_{1-4}$-(Ring F), wherein Ring F is a substituted or unsubstituted, 3- to 7-membered, monocyclic heterocyclic ring.

21. The compound of claim 1, or a pharmaceutically acceptable salt thereof, wherein $R^B$ is substituted or unsubstituted cyclopropyl.

22. The compound of claim 1, or a pharmaceutically acceptable salt thereof, wherein j is 0.

23. The compound of claim 1, or a pharmaceutically acceptable salt thereof, wherein m is 0.

24. The compound of claim 1, or a pharmaceutically acceptable salt thereof, wherein

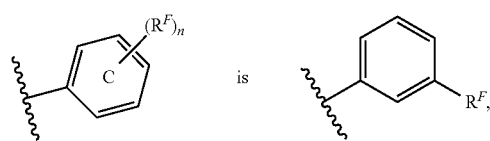

-continued

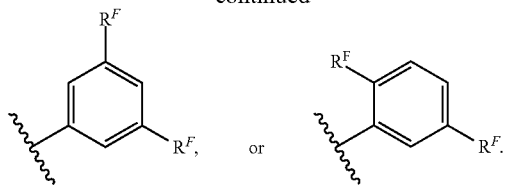

25. The compound of claim 1, or a pharmaceutically acceptable salt thereof, wherein the first instance of $R^F$ is —C(=O)NH—$R^{F1}$ or —C(=O)N(CH$_3$)—$R^{F1}$, wherein $R^{F1}$ is substituted or unsubstituted phenyl.

26. The method of claim 16, wherein the disease is an inflammatory disease.

27. The method of claim 16, wherein the disease is allergy, asthma, blepharitis, delayed-type hypersensitivity reaction, dermatomyositis, hay fever, immediate hypersensitivity reaction, inflammatory dermatosis, ocular inflammatory disease, pemphigoid, pemphigus, poison ivy dermatitis, psoriasis, scleroderma, systemic lupus erythematosus, uveitis, or vaginitis.

28. The method of claim 16, wherein the disease is inflammatory dermatosis.

29. The method of claim 16, wherein the disease is an ocular inflammatory disease.

30. The method of claim 16, wherein the disease is enterocolitis, rheumatoid arthritis, or systemic lupus erythematosis.

31. The method of claim 16, wherein the disease is cancer.

32. The method of claim 16, wherein the subject is a human.

* * * * *

UNITED STATES PATENT AND TRADEMARK OFFICE
CERTIFICATE OF CORRECTION

PATENT NO. : 10,975,058 B2  
APPLICATION NO. : 16/410371  
DATED : April 13, 2021  
INVENTOR(S) : Nathanael S. Gray et al.

Page 1 of 1

It is certified that error appears in the above-identified patent and that said Letters Patent is hereby corrected as shown below:

In the Claims

Claim 15, Column 108, Lines 1-17, the formula:

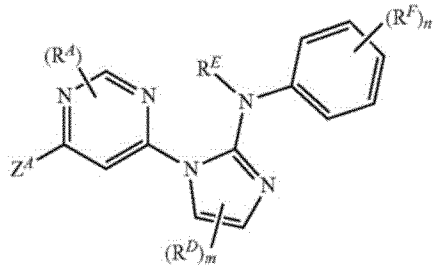

Should be replaced with the formula:

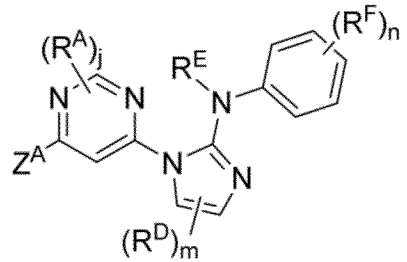

Signed and Sealed this  
Seventeenth Day of August, 2021

Drew Hirshfeld  
*Performing the Functions and Duties of the  
Under Secretary of Commerce for Intellectual Property and  
Director of the United States Patent and Trademark Office*